(12) United States Patent
Dub et al.

(10) Patent No.: US 10,487,100 B1
(45) Date of Patent: Nov. 26, 2019

(54) MACROCYCLIC LIGANDS AND THEIR COMPLEXES FOR BIFUNCTIONAL MOLECULAR CATALYSIS

(71) Applicant: Los Alamos National Security, LLC, Los Alamos, NM (US)

(72) Inventors: Pavel Dub, Los Alamos, NM (US); John C. Gordon, Los Alamos, NM (US); Jurgen G. Schmidt, Los Alamos, NM (US); Yury Minko, Los Alamos, NM (US); Robert F. Williams, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/944,503

(22) Filed: Apr. 3, 2018

Related U.S. Application Data

(60) Provisional application No. 62/481,427, filed on Apr. 4, 2017.

(51) Int. Cl.
| | |
|---|---|
| *C07D 487/22* | (2006.01) |
| *C07F 15/00* | (2006.01) |
| *C07F 9/6587* | (2006.01) |
| *C07F 9/659* | (2006.01) |
| *B01J 31/18* | (2006.01) |

(52) U.S. Cl.
CPC ......... *C07F 15/0053* (2013.01); *B01J 31/189* (2013.01); *B01J 31/1825* (2013.01); *C07D 487/22* (2013.01); *C07F 9/659* (2013.01); *C07F 9/6587* (2013.01); *B01J 2231/625* (2013.01); *B01J 2531/821* (2013.01)

(58) Field of Classification Search
CPC .. C07D 487/22; C07F 15/0053; C07F 9/6587; C07F 9/659
See application file for complete search history.

(56) References Cited

U.S. PATENT DOCUMENTS

| | | | |
|---|---|---|---|
| 4,895,840 | A | 1/1990 | Shanklin, Jr. et al. |
| 9,000,212 | B2 | 4/2015 | Touge et al. |
| 9,328,079 | B2 | 5/2016 | Ohkuma et al. |
| 10,196,414 | B2 | 2/2019 | Geisser et al. |
| 2007/0149575 | A1 | 6/2007 | Schnatterer et al. |
| 2013/0171067 | A1 | 7/2013 | Guminski et al. |
| 2014/0163257 | A1 | 6/2014 | Hori et al. |
| 2016/0326199 | A1 | 11/2016 | Geisser et al. |
| 2017/0088571 | A1 | 3/2017 | Dub et al. |

FOREIGN PATENT DOCUMENTS

| | | |
|---|---|---|
| WO | WO 01/83436 | 11/2001 |
| WO | WO 2011/048727 | 4/2011 |
| WO | WO 2012/026201 | 3/2012 |
| WO | WO 2012/048646 | 4/2012 |
| WO | WO 2012/137460 | 10/2012 |
| WO | WO 2012/144650 | 10/2012 |
| WO | WO 2013/065867 | 5/2013 |
| WO | WO 2015/163440 | 10/2015 |

OTHER PUBLICATIONS

Combariza et al., "The utility of ion-molecule reactions in a quadruple ion trap mass spectrometer for analyzing metal complex coordination structure," *Analytica Chimica Acta* 496(1-2):233-248, Oct. 31, 2003.
Final Office Action dated for U.S. Appl. No. 15/375,055 dated Aug. 29, 2018.
Huang et al., "Studies on tetranuclear copper (II) complexes of a macrocyclic ligand bearing 2-thiophenooethylamine pendant arms," *Journal of Molecular Structure*, 983(1-3): 186-193, Nov. 1, 2010.
International Search Report and Written Opinion issued for International Application No. PCT/US2015/034793 dated Sep. 2, 2015.
Kuriyama et al., "Catalytic hydrogenation of esters. Development of an efficient catalyst and processes for synthesizing (R)-1,2-propanediol and 2-(1-methoxy)ethanol," *Org. Process Res. Dev.*, 16(1): 166-171, Nov. 29, 2011.
Matsumura et al., "Chiral Ruthenbicyclic Complexes: Precatalysts for Rapid, Enantioselective, and Wide-Scope Hydrogenation of Ketones," *J. Am. Chem. Soc.*, 133(28): 10696-10699, Jun. 16, 2011.
Non-Final Office Action issued for U.S. Appl. No. 15/735,055 dated Feb. 15, 2018.
Rey et al., "Synthesis and Characterization of Mixed-Ligand Oxorhenium Complexes with SNN Type of Ligand. Isolation of a Novel ReO[SN][S][S] Complex," *Inorg. Chem.*, 39(19): 4211-4218, Aug. 25, 2000.
STN Registry No. 1002277-95-3, Feb. 8, 2008.
STN Registry No. 1342746-15-9, Nov. 8, 2011.
Touge et al., "Efficient Access to Chiral Benzhydrols via Asymmetric Transfer Hydrogenation of Unsymmetrical Benzophenones with Bifunctional Oxo-Tethered Ruthenium Catalysts," *J. Am. Chem. Soc.*, 138(32): 10084-10087, Jul. 27, 2016.
Touge et al., "Oxo-Tethered Ruthenium (II) Complex as a Bifunctional Catalyst for Asymmetric Transfer Hydrogenation and $H_2$ Hydrogenation," *J. Am. Chem. Soc.*, 133(38): 14960-14963, Aug. 26, 2011.

(Continued)

*Primary Examiner* — Shawquia Jackson
(74) *Attorney, Agent, or Firm* — Klarquist Sparkman, LLP

(57) ABSTRACT

Disclosed herein are embodiments of chiral and achiral macrocyclic polydentate ligands and methods of preparing the same. Disclosed herein are also embodiments of metal coordination complexes derived from these macrocyclic polydentate ligands and methods of preparing the same. The metal coordination complexes described herein, can be used for a variety of catalytic reactions, including hydrogenation and transfer hydrogenation of unsaturated organic compounds, dehydrogenation of alcohols and boranes, an asymmetric Michael-type addition reaction, or an aerobic oxidative kinetic resolution of an organic compound, dehydrogenative couplings and other catalytic transformations.

16 Claims, 4 Drawing Sheets

(56) References Cited

OTHER PUBLICATIONS

U.S. Appl. No. 15/375,055, filed Dec. 9, 2016.
Zhang et al., "Asymmetric transfer hydrogenation of aromatic ketones with chiral diaminothiophene/iridium catalyst systems," *Journal of Molecular Catalysis A*, 307(1-2): 149-153, Jul. 15, 2009.

MACROCYCLIC LIGANDS AND THEIR COMPLEXES FOR BIFUNCTIONAL MOLECULAR CATALYSIS

CROSS REFERENCE TO RELATED APPLICATION

This application claims the benefit of U.S. Provisional Patent Application No. 62/481,427, filed Apr. 4, 2017, which is incorporated herein by reference in its entirety.

ACKNOWLEDGMENT OF GOVERNMENT SUPPORT

This invention was made with government support under Contract No. DE-AC52-06NA25396 awarded by the U. S. Department of Energy. The government has certain rights in the invention.

FIELD

Disclosed herein are embodiments of polydentate macrocyclic ligands as well as embodiments of making, and using the same, for instance, as transition metal complexes.

BACKGROUND

Progress in homogeneous catalysis including homogeneous hydrogenation often involves the development of novel ligands and their transition-metal complexes that are active as pre-catalysts or catalysts. The vast majority of ligands used in homogeneous catalysis are based on P and/or N donor atoms and an enormous number of such bi-, tri- and tetradentate ligands have been designed and synthesized over the past half century.

As understood, polydentate chelating ligands bearing N—H functionalities play a crucial role in a conventional bifunctional metal-ligand (i.e., M/NH) molecular catalysis, in which the ligand facilitates the catalytic reaction via stabilization of rate-determining transition states, for example, through N—H . . . O hydrogen bonding interactions and/or an N—H bond cleavage/formation, respectively. The bifunctional molecular catalysis based on metal-ligand (M/NH) cooperation was originally developed for asymmetric hydrogenation chemistry (e.g. Noyori asymmetric hydrogenation) and transfer hydrogenation of ketones and imines, and is now applicable to a variety of chemical transformations with a wide scope and high practicality. For example, the chemical transformations include, but are not limited to, practical hydrogenation of carboxylic and carbonic acid derivatives, hydrogenation and electroreduction of $CO_2$, reductive transformation of $CO_2$ into methanol (for a methanol based economy), various acceptorless dehydrogenations, asymmetric Michael reactions of 1,3-dicarbonyl compounds with cyclic enones and nitroalkenes, stereoselective catalytic C—N and C—C bond-forming reactions, aerobic oxidative kinetic resolution of racemic secondary alcohols, asymmetric hydration of nitriles and others.

Given the utility of these catalysts (representative examples from Takasago Int. Corp. are: RUCY-XylBINAP: a) Hori et al., Published Patent WO/2012/137460A1 by Takasago International Corporation for "Novel Ruthenium Complex and Process for Producing Optically Active Alcohol Compound Using the Same as Catalyst"; (b) Matsumura et al., "Chiral Ruthenbicyclic Complexes: Precatalysts for Rapid, Enantioselective, and Wide-Scope Hydrogenation of Ketones" J. Am. Chem. Soc. 2011, 133, 10696; and (c) Ohkuma et al., U.S. Pat. No. 9,328,079 by Takasago International Corporation for "Process for Producing Optically Active Amine"; Ts-DENEB: (a) Tanaka et al., Published Patent WO/2013/065867A1 by Takasago International Corporation for "Method for Producing Optically Active Beta-Hydroxy-alpha-Aminocarboxylic Acid Ester"; (c) Touge et al. Published Patent WO/2012/144650A1 by Takasago International Corporation for "Method for Producing Compound with Carbonyl Group Using Ruthenium Carbonyl Complex having Tridentate Ligand as Dehydrogenation Oxidation Catalyst"; (d) Touge et al., "OxoOTehered Ruthenium (II) Complex as a Bifunctional Catalyst for Asymmetric Transfer Hydrogenation and $H_2$ Hydrogenation" J. Am. Chem. Soc. 2011, 133, 14960; (e) Touge, T.; Nara, H.; Fujiwhara, M.; Kayaki, Y.; Ikariya, T. J. Am. Chem. Soc. 2016, 138, 10084; and (f) Touge et al., Published Patent WO/2012/026201A1 by Takasago International Corporation, for "Ruthenium-Diamine Complexes and Method for Producing Optically Active Compounds"; Ru-MACHO: (a) Touge et al. U.S. Pat. No. 9,000,212B2 by Takasago International Corporation, for "Method for Producing Compound with Carbonyl Group using Ruthenium Carbonyl Complex having Tridentate Ligand as Dehydrogenation Oxidation Catalyst"; (b) Hori et al. for "Method for reducing halogenobenzoic acid ester using ruthenium carbonyl complex" by Takasago International Corporation, US Published Patent 20140163257A1 (c) Kuriyama et al. for "Preparation of ruthenium carbonyl complexes having tridentate aminodiphosphine ligand as reductive hydrogenation catalysts". Published Patent WO/2011/048727A1; (d) Kuriyama, W. et al. for "Catalytic hydrogenation of esters. Development of an efficient catalyst and processes for synthesizing (R)-1,2-propanediol and 2-(1-methoxy)ethanol." Org. Process Res. Dev. 16, 166-171, (2012); (e) Ogata et al. for "Atmospheric Hydrogenation of Esters Catalyzed by PNP-Ruthenium Complexes with an N-Heterocyclic Carbene Ligand." Org. Lett. 18, 3894-3897, (2016); and (f) Ogata et al. for "Preparation of ruthenium complexes having bis(phosphinoalkyl)amine and N-heterocyclic carbene ligands, organic reaction catalysts containing them, and their use". Published Patent WO/2015/163440A1 (2015)), there is interest in further ligand and catalyst design.

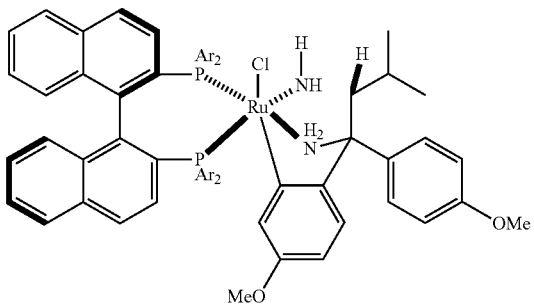

(R)-RUCY-XylBINAP
Takasago Int Corp
R0139 TCl

-continued

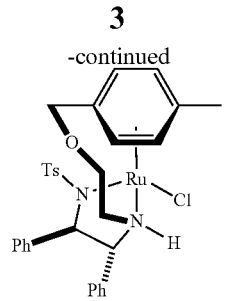

(R, R)-Ts-DENEB
Takasago Int Corp
T3078 TCI

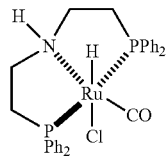

Ru-MACHO
Takasago Int Corp
739103 Aldrich

As such, there exists a continued need for developing novel ligand and catalyst design.

SUMMARY

Disclosed herein are embodiments of a macrocyclic ligand, having a structure satisfying Formula 1

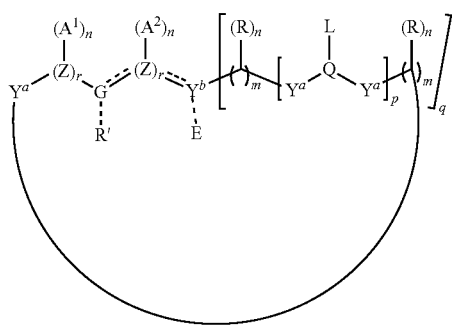

Formula 1 wherein each bond indicated with "===" is a single bond or a double bond as needed to satisfy valency requirements;

each m, p and q can independently be an integer selected from 0 to 10;

each n and r can independently be 0 or 1;

Z, when present, can be selected from carbon, or any heteroatom selected from O, N, S or P;

G can be selected from N, and R', when present, can be hydrogen;

each R, $A^1$ and $A^2$ can independently be selected from hydrogen, halogen, aliphatic, haloaliphatic, haloheteroaliphatic, heteroaliphatic, aromatic, aliphatic-aromatic, heteroaliphatic-aromatic or any combination thereof;

each $Y^a$ can independently selected from O, S, $C(J^1)_2$, $P(J^1)$ wherein each $J^1$ independently is hydrogen, halogen, aliphatic, haloaliphatic, haloheteroaliphatic, heteroaliphatic, aromatic or any combination thereof;

$Y^b$ can be selected from O, S, $C(J^2)_2$, $P(J^2)$ wherein each $J^2$ independently is hydrogen, halogen, aliphatic, haloaliphatic, haloheteroaliphatic, heteroaliphatic, aromatic or any combination thereof;

E can be selected from hydrogen, halogen, aliphatic, haloaliphatic, haloheteroaliphatic, heteroaliphatic, aromatic or any combination thereof;

each Q can independently be selected from one electron pair donor, such as P, S, N, O or carbene having a formula: $C(J^3)_2$ wherein each $J^3$ independently is hydrogen, halogen, aliphatic, haloaliphatic, haloheteroaliphatic, heteroaliphatic, aromatic or any combination thereof;

each L can independently be selected from electron lone pair, O, S, SO, $C(J^4)_2$, $B(J^4)_3$ wherein each $J^4$ independently is hydrogen, halogen, aliphatic, haloaliphatic, haloheteroaliphatic, heteroaliphatic, aromatic or any combination thereof; and wherein the macrocyclic ligand is not, or is other than, any one or more of the following ligands:

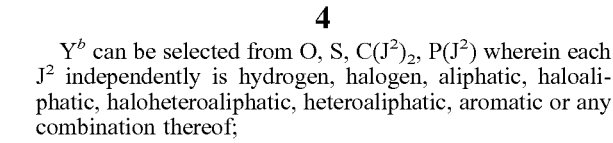

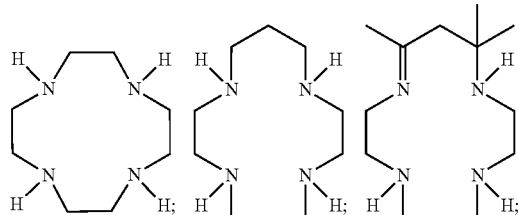

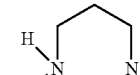

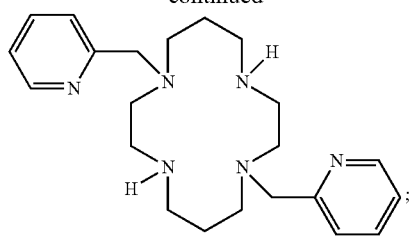
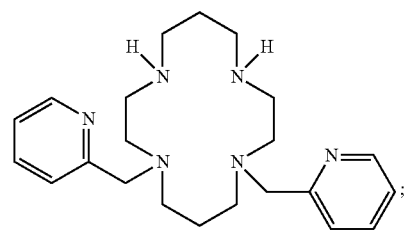
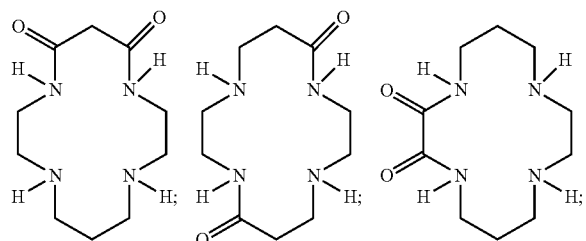
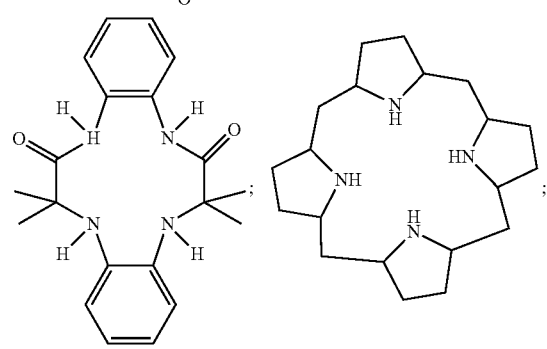
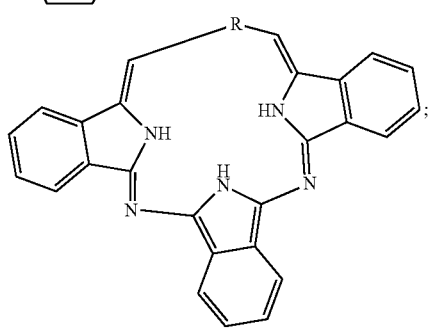
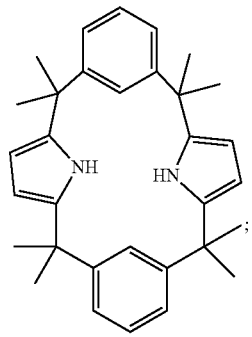
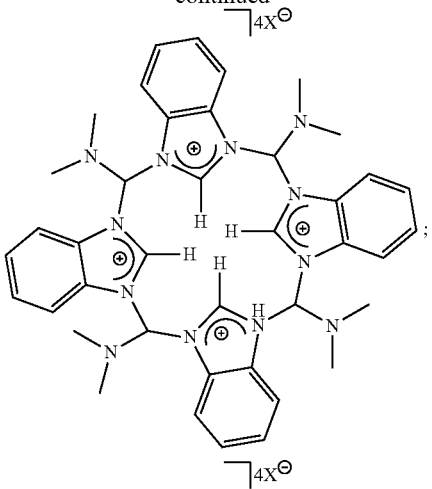
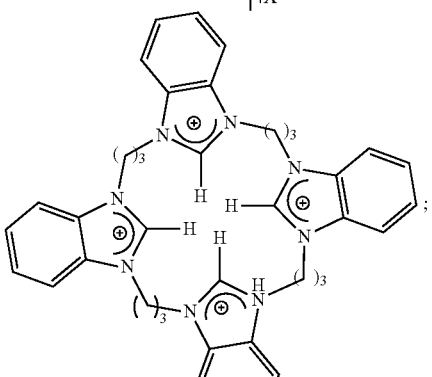
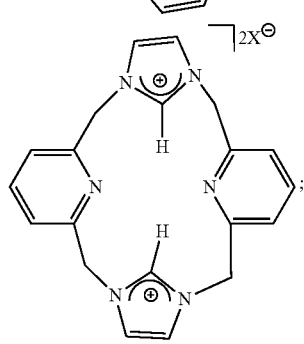
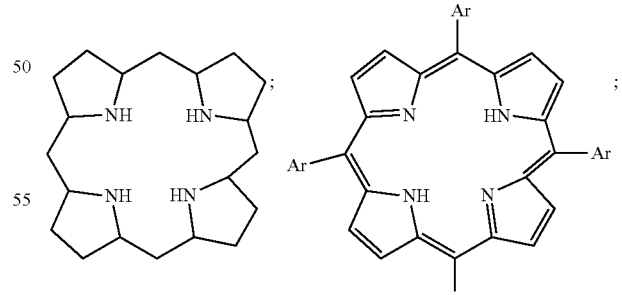
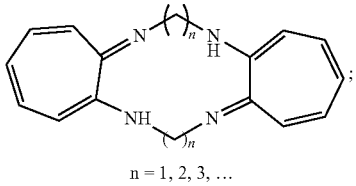
n = 1, 2, 3, …

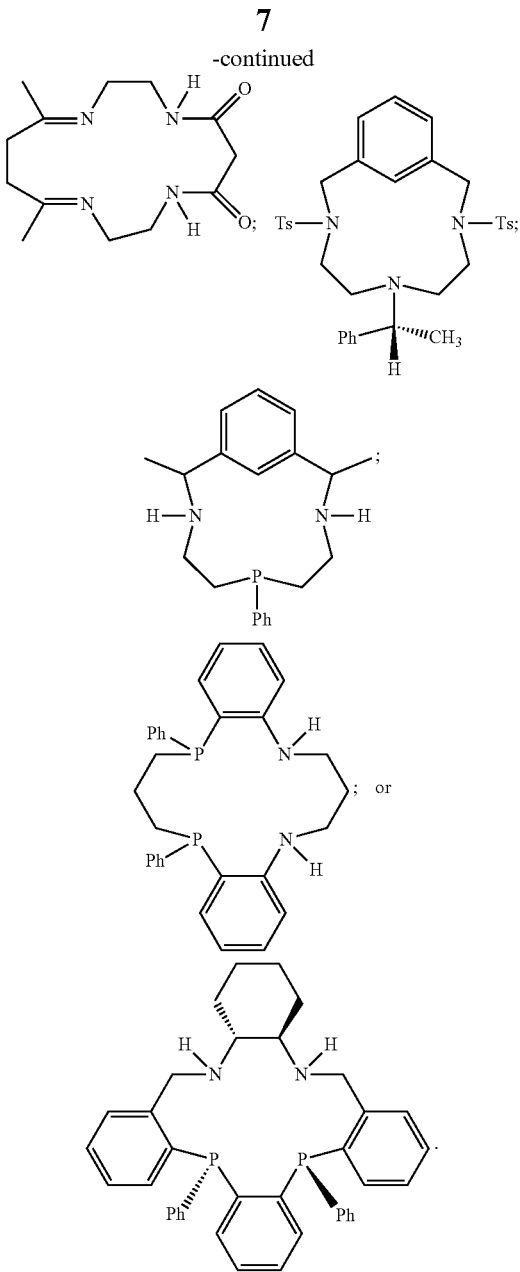

In some embodiments, the macrocyclic ligand of Formula 1 has a structure satisfying any one or more of Formulas 1A-1D:

Formula 1A

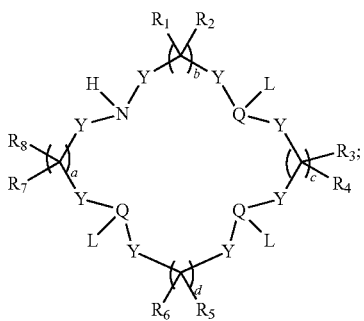

Formula 1B

Formula 1C

Formula 1D wherein:

Q is selected from one electron pair donor selected from phosphorus, sulfur, nitrogen, oxygen, or carbon (carbene);

L is selected from a lone pair (or its absence), oxygen, $BH_3$ and similar, or substituents from among a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

Y is selected from a functionality containing a heteroatom selected from NH, O, S, PR, or an optionally substituted $CH_2$ group or its absence, wherein R is selected from hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

a, b, c, and d can independently be an integer selected from 0, 1, 2, 3, 4, 5, 6, 7, 8, 9 or 10; and $R_1$, $R_2$, $R_3$, $R_4$, $R_5$, $R_6$, $R_7$, $R_8$ and $R_9$ are independently at each occurrence H, a substituted or unsubstituted $C_{1-6}$ alkyl, a substituted or unsubstituted $C_{3-6}$ cycloalkyl, a substituted or unsubstituted aryl, a substituted or unsubstituted heteroaryl, a substituted or unsubstituted arylalkyl, or a combination thereof.

Also disclosed herein are embodiments of methods for making the macrocyclic ligand having the Formula 1. In disclosed embodiments, a first heteroatom moiety is coupled with a second heteroatom moiety to promote a cyclization reaction to form the macrocyclic ligand. In particular disclosed embodiments, the coupling of the first heteroatom moiety and the second heteroatom moiety can be accomplished via a Michael-type addition reaction.

Also disclosed herein is an embodiment of metal coordination complex that has a structure satisfying Formula 2

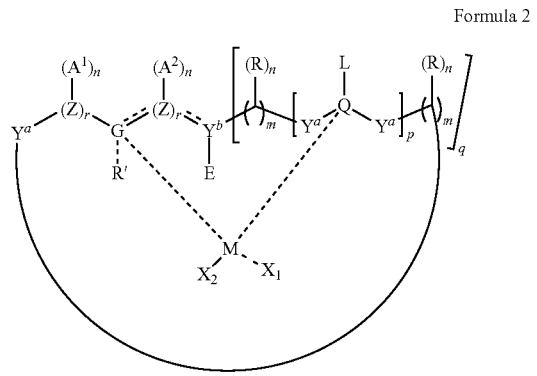

Formula 2 wherein
each bond indicated with "=═=" is a single bond or a double bond as needed to satisfy valency requirements;
each m, p and q can independently be an integer selected from 0 to 10;
each n and r can independently be 0 or 1;
Z, when present, can be selected from carbon or a heteroatom selected from O, N, S or P;
G can be selected from N, and R', when present, can be hydrogen;
each R, $A^1$ and $A^2$ can independently be selected from hydrogen, halogen, aliphatic, haloaliphatic, haloheteroaliphatic, heteroaliphatic, aromatic, aliphatic-aromatic, heteroaliphatic-aromatic or any combination thereof;
each $Y^a$ can independently selected from O, S, $C(J^1)_2$, $P(J^1)$ wherein each $J^1$ independently is hydrogen, halogen, aliphatic, haloaliphatic, haloheteroaliphatic, heteroaliphatic, aromatic or any combination thereof;
$Y^b$ can be selected from O, S, $C(J^2)_2$, $P(J^2)$ wherein each $J^2$ independently is hydrogen, halogen, aliphatic, haloaliphatic, haloheteroaliphatic, heteroaliphatic, aromatic or any combination thereof;
E can be selected from hydrogen, halogen, aliphatic, haloaliphatic, haloheteroaliphatic, heteroaliphatic, aromatic or any combination thereof;
each Q can independently be selected from one electron pair donor, such as P, S, N, O or carbene having a formula: $C(J^3)_2$ wherein each $J^3$ independently is hydrogen, halogen, aliphatic, haloaliphatic, haloheteroaliphatic, heteroaliphatic, aromatic or any combination thereof;
each L can independently be selected from electron lone pair, O, S, SO, $C(J^4)_2$, $B(J^4)_3$ wherein each $J^4$ independently is hydrogen, halogen, aliphatic, haloaliphatic, haloheteroaliphatic, heteroaliphatic, aromatic or any combination thereof;
M can be any transition metal selected from Group 3 to Group 12, including the lanthanides and actinides; and
each $X_1$ and $X_2$ independently can be selected from hydrogen, halogen, aliphatic, haloaliphatic, haloheteroaliphatic, heteroaliphatic, aromatic, aliphatic-aromatic, heteroaliphatic-aromatic, or any combination thereof.

In some embodiments, the metal coordination complex of Formula 2 has a structure satisfying any one or more of Formulas 2A-2I:

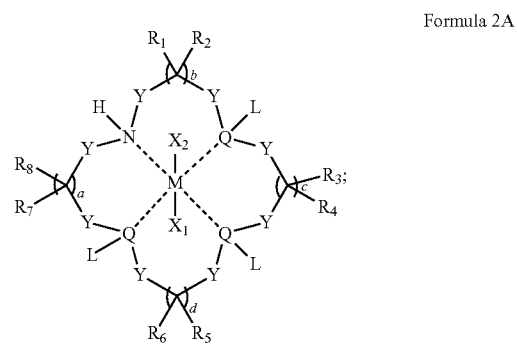

Formula 2A

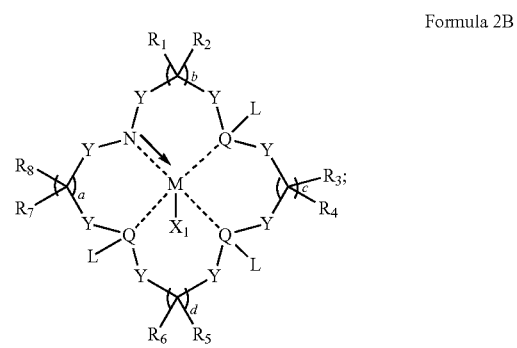

Formula 2B

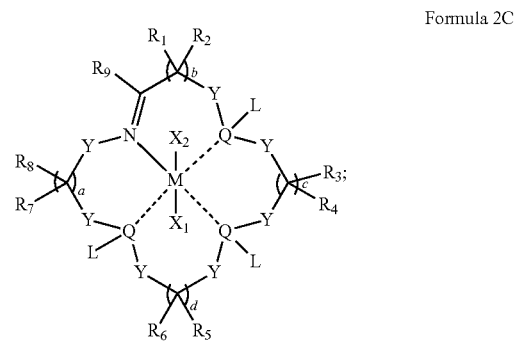

Formula 2C

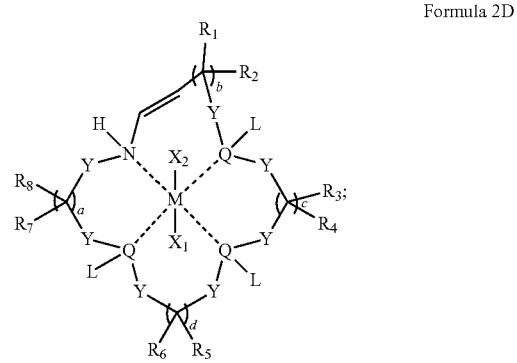

Formula 2D

Formula 2E

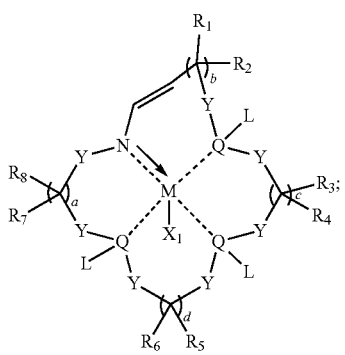

Formula 2F

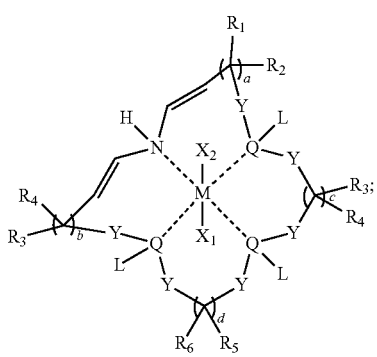

Formula 2G

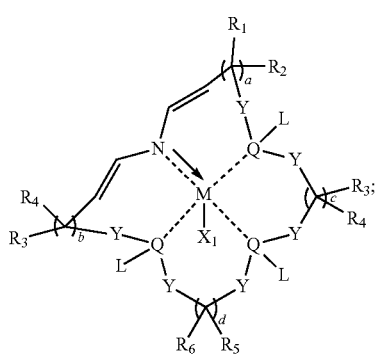

Formula 2H

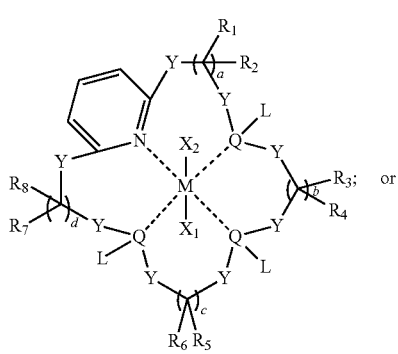

Formula 2I

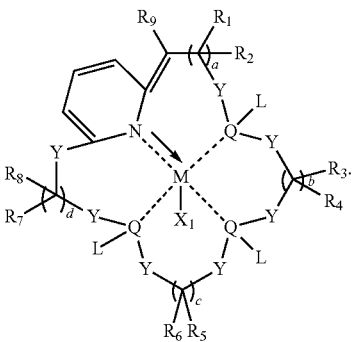

wherein:

Q is selected from one electron pair donor such as phosphorus, sulfur, nitrogen, oxygen, or carbon (carbene);

$X_1$ and $X_2$ independently are an anionic substituent selected from F, Cl, Br, I, H, OTf, OH, OR (R is an alkyl), $BH_4$ or $PF_6$;

L is selected from a lone pair (or its absence), oxygen, $BH_3$ and similar, or substituents from among a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

Y is selected from a functionality containing a heteroatom selected from NH, O, S, PR, an optionally substituted $CH_2$ group or its absence, wherein R is selected from hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

a, b, c, and d can independently be an integer selected from 0, 1, 2, 3, 4, 5, 6, 7, 8. 9 or 10;

M can be any transition metal selected from Group 3 to Group 12, including the lanthanides and actinides; and $R_1$, $R_2$, $R_3$, $R_4$, $R_5$, $R_6$, $R_7$, $R_8$, and $R_9$ are independently at each occurrence a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, a substituted or unsubstituted arylalkyl or a combination thereof.

In particular disclosed embodiment, M is a ruthenium metal, and the complex has a structure satisfying any one or more of Formulas 3A-3I:

Formula 3A

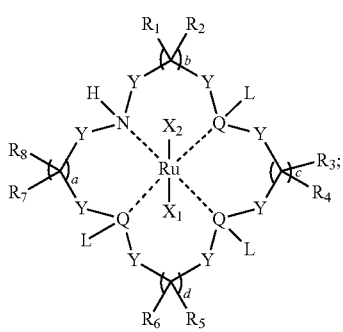

Formula 3B
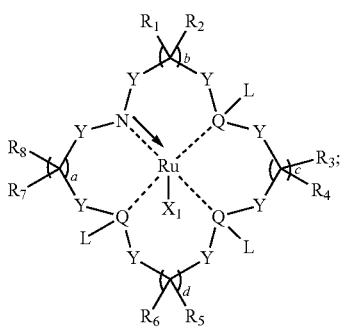

Formula 3C
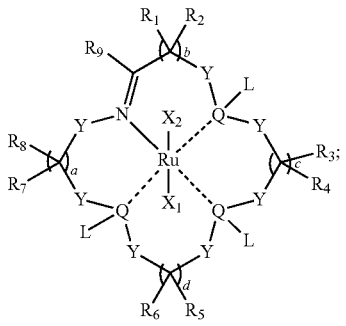

Formula 3D
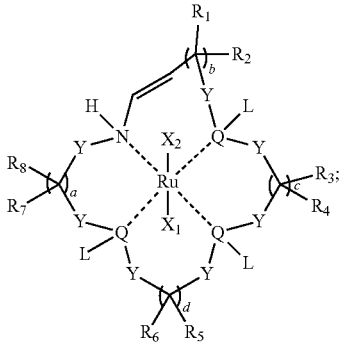

Formula 3E
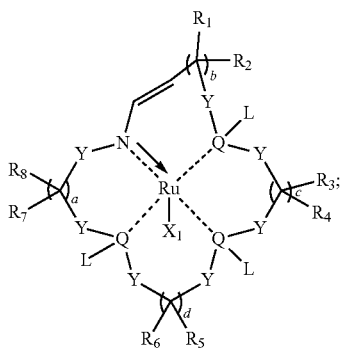

Formula 3F
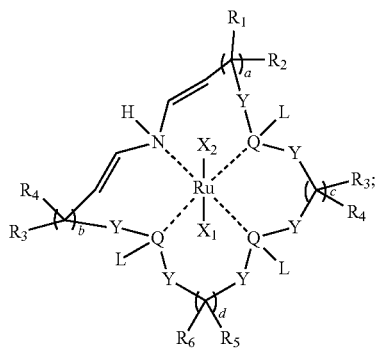

Formula 3G
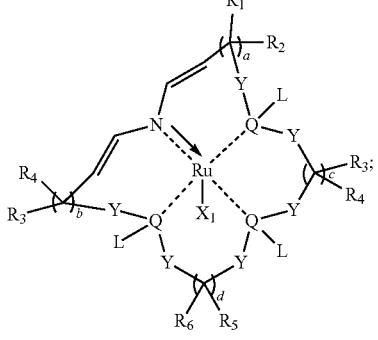

Formula 3H
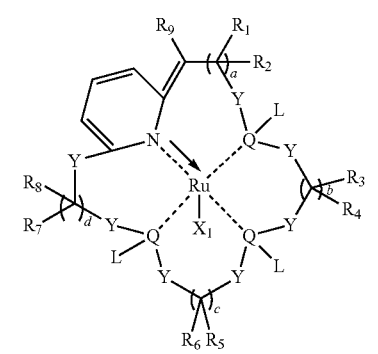

or

Formula 3I
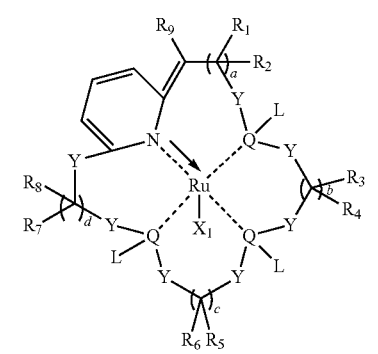

wherein:
Q is selected from one electron pair donor selected from phosphorus, sulfur, nitrogen, oxygen, or carbon (carbene);

$X_1$ and $X_2$ independently are an anionic substituent selected from F, Cl, Br, I, H, OTf, OH, OR (R is any alkyl), $BH_4$ or $PF_6$;

L is selected from a lone pair (or its absence), oxygen, $BH_3$ and similar, or substituents from among a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

Y is selected from a functionality containing a heteroatom selected from NH, O, S, PR, an optionally substituted $CH_2$ group or its absence, wherein R is selected from hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

a, b, c, and d can independently be an integer selected from 0, 1, 2, 3, 4, 5, 6, 7, 8, 9 or 10;

$R_1$, $R_2$, $R_3$, $R_4$, $R_5$, $R_6$, $R_7$, $R_8$, and $R_9$ are independently at each occurrence a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, a substituted or unsubstituted arylalkyl or a combination thereof.

Disclosed herein also is an embodiment of a method for making the metal coordination complex of Formula 2. In particular disclosed embodiment, the macrocyclic ligand is coupled with a metal-containing precursor in the presence of a solvent to promote coordinating the macrocyclic ligand with at least one transition metal.

The macrocyclic ligands and the metal coordination complexes described herein can be used in a variety of catalytic reactions, such as, hydrogenation and transfer hydrogenation of unsaturated organic compounds, dehydrogenation of alcohols and boranes, an asymmetric Michael-type addition reaction, or an aerobic oxidative kinetic resolution of an organic compound, dehydrogenative couplings and other catalytic transformations.

The foregoing will become more apparent from the following detailed description, which proceeds with reference to the accompanying figures.

DETAILED DESCRIPTION

I. Overview of Terms

Figure 1:
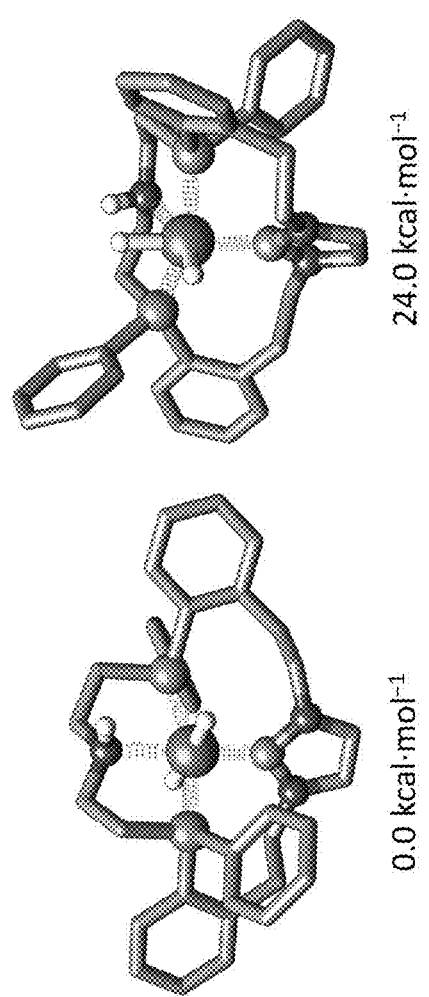
FIG. 1 depicts corresponding geometries of a representative ligand disclosed herein.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Although the steps of some of the disclosed methods are described in a particular, sequential order for convenient presentation, it should be understood that this manner of description encompasses rearrangement, unless a particular ordering is required by specific language set forth below. For example, steps described sequentially may in some cases be rearranged or performed concurrently. Additionally, the description sometimes uses terms like "produce" or "provide" to describe the disclosed methods. These terms are high-level abstractions of the actual steps that are performed. The actual steps that correspond to these terms will vary depending on the particular implementation and are readily discernible by one of ordinary skill in the art.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the donor compound to which it is bound. Also, a dashed bond (i.e., "---") as used in certain formulas described herein indicates an optional bond (that is, a bond that may or may not be present). A person of ordinary skill in the art would recognize that the definitions provided below and the donor compounds and formulas included herein are not intended to include impermissible substitution patterns (e.g., methyl substituted with 5 different groups, and the like). Such impermissible substitution patterns are easily recognized by a person of ordinary skill in the art. In formulas and donor compounds disclosed herein, a hydrogen atom is present and completes any formal valency requirements (but may not necessarily be illustrated) wherever a functional group or other atom is not illustrated. For example, a phenyl ring that is drawn as

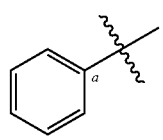 [SMILES: *c1ccccc1]

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Acyl Halide: —C(O)X, wherein X is a halogen, such as Br, F, I, or Cl.

Aldehyde: —C(O)H.

Aliphatic: A hydrocarbon group having at least one carbon atom to 50 carbon atoms ($C_1$-$C_{50}$), such as one to 25 carbon atoms ($C_1$-$C_{25}$), or one to ten carbon atoms ($C_1$-$C_{10}$), and which includes alkanes (or alkyl), alkenes (or alkenyl), alkynes (or alkynyl), including cyclic versions thereof, and further including straight- and branched-chain arrangements, and all stereo and position isomers as well.

Aliphatic-aryl: An aryl group that is or can be coupled to a compound disclosed herein, wherein the aryl group is or becomes coupled through an aliphatic group.

Aliphatic-heteroaryl: A heteroaryl group that is or can be coupled to a compound disclosed herein, wherein the heteroaryl group is or becomes coupled through an aliphatic group.

Alkenyl: An unsaturated monovalent hydrocarbon having at least two carbon atom to 50 carbon atoms ($C_2$-$C_{50}$), such as two to 25 carbon atoms ($C_2$-$C_{25}$), or two to ten carbon atoms ($C_2$-$C_{10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkoxy: —O-aliphatic, with exemplary embodiments including, but not limited to, methoxy, ethoxy, n-propoxy, isopropoxy, n-butoxy, t-butoxy, sec-butoxy, n-pentoxy.

Alkyl: A saturated monovalent hydrocarbon having at least one carbon atom to 50 carbon atoms ($C_1$-$C_{50}$), such as one to 25 carbon atoms ($C_1$-$C_{25}$), or one to ten carbon atoms ($C_1$-$C_{10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkyl-aryl/Alkenyl-aryl/Alkynyl-aryl: An aryl group that is or can be coupled to a compound disclosed herein, wherein the aryl group is or becomes coupled through an alkyl, alkenyl, or alkynyl group, respectively.

Alkynyl: An unsaturated monovalent hydrocarbon having at least two carbon atom to 50 carbon atoms ($C_2$-$C_{50}$), such as two to 25 carbon atoms ($C_2$-$C_{25}$), or two to ten carbon atoms ($C_2$-$C_{10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Ambient Temperature: A temperature ranging from 16° C. to 26° C., such as 19° C. to 25° C., or 20° C. to 25° C.

Amide: —C(O)NR$^a$R$^b$ or —NHCOR$^a$ wherein each of R$^a$ and R$^b$ independently is selected from hydrogen, aliphatic, heteroaliphatic, haloaliphatic, haloheteroaliphatic, aromatic, or any combination thereof.

Amine: —NR$^a$R$^b$, wherein each of R$^a$ and R$^b$ independently is selected from hydrogen, aliphatic, hetero-aliphatic, halo-aliphatic, halo-hetero-aliphatic, aromatic, or any combination thereof.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

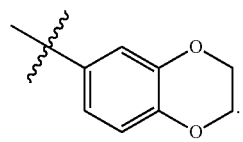 [SMILES: *c1ccc2c(c1)OCCO2]

However, in certain examples, context or express disclosure may indicate that the point of attachment is through a non-aromatic portion of the condensed ring system. For example,

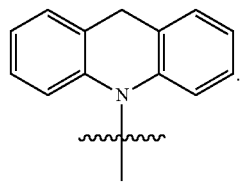 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen, such as aliphatic, hetero-aliphatic, aromatic, other functional groups, or any combination thereof.

Carboxyl: —C(O)OH or an anion thereof.

Catalyst: A compound, usually present in small amounts relative to reactants, capable of catalyzing a synthetic reaction, as would be readily understood by a person of ordinary skill in the art. In some embodiments, catalysts may include transition metal coordination complex.

Coordination complex: A complex comprising a central atom or ion, which is usually a metal cation, and surrounded by an array of bound molecules or ions. The array of bound molecules or ions that bind to transition-metal ions to form these complexes are called ligands or complexing agents. A coordination complex whose central atom is a metal atom is called a metal complex.

Disulfide: —SSR$^a$, wherein R$^a$ is selected from hydrogen, aliphatic, heteroaliphatic, haloaliphatic, haloheteroaliphatic, aromatic, or any combination thereof.

Electron-Donating Group: A functional group capable of donating at least a portion of its electron density into the ring to which it is directly attached, such as by resonance.

Electron-Withdrawing Group: A functional group capable of accepting electron density from the ring to which it is directly attached, such as by inductive electron withdrawal.

Ester: —C(O)OR$^a$ or —OC(O)R$^a$, wherein R$^a$ is selected from aliphatic, hetero-aliphatic, halo-aliphatic, halo-hetero-aliphatic, aromatic, or any combination thereof.

Halo-aliphatic: An aliphatic group wherein one or more hydrogen atoms, such as one to 10 hydrogen atoms, independently is replaced with a halogen atom, such as fluoro, bromo, chloro, or iodo.

Haloaliphatic-aryl: An aryl group that is or can be coupled to a compound disclosed herein, wherein the aryl group is or becomes coupled through a haloaliphatic group.

Haloaliphatic-heteroaryl: A heteroaryl group that is or can be coupled to a compound disclosed herein, wherein the heteroaryl group is or becomes coupled through a haloaliphatic group.

Haloalkyl: An alkyl group wherein one or more hydrogen atoms, such as one to 10 hydrogen atoms, independently is replaced with a halogen atom, such as fluoro, bromo, chloro, or iodo. In an independent embodiment, haloalkyl can be a $CX_3$ group, wherein each X independently can be selected from fluoro, bromo, chloro, or iodo.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroaliphatic-aryl: An aryl group that is or can be coupled to a compound disclosed herein, wherein the aryl group is or becomes coupled through a heteroaliphatic group.

Heteroalkyl/Heteroalkenyl/Heteroalkynyl: An alkyl, alkenyl, or alkynyl group (which can be branched, straight-chain, or cyclic) comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group.

Heteroalkyl-aryl/Heteroalkenyl-aryl/Heteroalkynyl-aryl: An aryl group that is or can be coupled to a compound disclosed herein, wherein the aryl group is or becomes coupled through a heteroalkyl, heteroalkenyl, or heteroalkynyl group, respectively.

Heteroalkyl-heteroaryl/Heteroalkenyl-heteroaryl/Heteroalkynyl-heteroaryl: A heteroaryl group that is or can be coupled to a compound disclosed herein, wherein the aryl group is or becomes coupled through a heteroalkyl, heteroalkenyl, or heteroalkynyl group, respectively.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen, such as aliphatic, heteroaliphatic, aromatic, other functional groups, or any combination thereof.

Heteroatom: An atom other than carbon, such as oxygen, nitrogen, sulfur, silicon, boron, selenium, or phosphorous. In particular disclosed embodiments, such as when valency constraints do not permit, a heteroatom does not include a halogen atom.

Ketone: —C(O)$R^a$, wherein $R^a$ is selected from aliphatic, heteroaliphatic, aromatic, any combination thereof.

Ligand: An ion or molecule that binds to a central metal atom or ion, such as a transition metal atom or a transition metal ion, to form a coordination complex. Ligands can be further characterized as monodentate, bidentate, tridentate, tetradentate, polydentate, etc., depending upon the number of donor atoms of the ion or molecule that bind to the central metal atom or ion. In some embodiments, the ion or the molecule may comprise one or more heteroatoms.

Polydentate ligand: ligand that binds with two or more atoms to a central atom or ion to form a coordination complex.

Silyl Ether: A functional group comprising a silicon atom covalently bound to an alkoxy group.

Sulfonyl/Sulfonate: —SO$_2$R$^a$, wherein R$^a$ is selected from hydrogen, aliphatic, heteroaliphatic, haloaliphatic, haloheteroaliphatic, aromatic, and any combination thereof.

Tetradentate ligand: ligand that binds with four donor atoms to a central atom or ion to form a coordination complex.

Transition metal: any metallic element of Group 3 to Group 12, including the actinides and lanthanides. In some embodiments, the transition metal may be a metal selected from Group 6 to Group 11. Such transition metals include, but are not limited to, Ti, V, Zr, Hf, Cr, Mo, W, Mn, Re, Fe, Ru, Os, Co, Rh, Ir, La, Ni, Pd, Pt, Cu, Ag, Au, Zn, and Sm, and preferably Cr, Co, Cu, Fe, Mn, Mo, Ni, Os, Pd, Rh, Sm, or W, or any subset combination thereof. In some embodiments, the catalysts comprise Fe, Ru, Os, Co, Rh, or Ir, or any subset combination thereof. In other specific embodiments, the catalysts comprise ruthenium.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. Any functional group disclosed herein and/or defined above can be substituted or unsubstituted, unless otherwise indicated therein.

II. Ligands

Disclosed herein are embodiments of novel polydentate macrocyclic ligands. In some embodiments, the ligands can have a structure satisfying the following formulas and can be made according to method embodiments disclosed herein.

In one embodiment, the polydentate macrocyclic ligand can have a structure satisfying Formula 1.

Formula 1

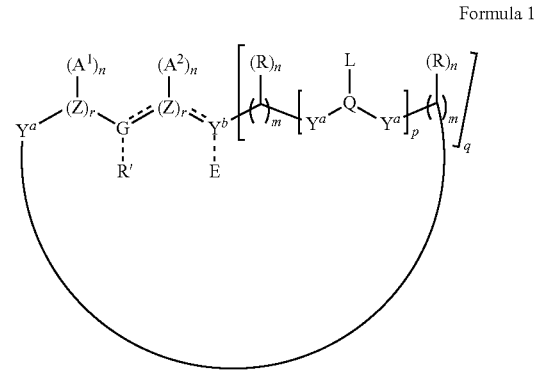

With reference to Formula 1, the following variable recitations can apply in one or more combinations:

each bond indicated with "$===$" is a single bond or a double bond as needed to satisfy valency requirements;

each m, p and q can independently be an integer selected from 0 to 10, such as 0, 1, 2, 3, 4, 5, 6, 7, 8, 9, or 10;

each n and r can independently be 0 or 1;

Z, when present, can be selected from carbon or a heteroatom selected from O, N, S or P;

G can be selected from N, and R', when present, can be hydrogen;

each R, $A^1$ and $A^2$ can independently be selected from hydrogen, halogen, aliphatic, haloaliphatic, haloheteroaliphatic, heteroaliphatic, aromatic, aliphatic-aromatic, heteroaliphatic-aromatic or any combination thereof, and when r is 1, $A^1$ and $A^2$ can form a cyclic ring, such as; heteroaliphatic or heteraryl group (e.g., pyridine, thiophene, etc.);

each $Y^a$ can independently selected from O, S, $C(J^1)_2$, $P(J^1)$ wherein each $J^1$ independently is hydrogen, halogen, aliphatic, haloaliphatic, haloheteroaliphatic, heteroaliphatic, aromatic or any combination thereof;

$Y^b$ can be selected from O, S, $C(J^2)_2$, $P(J^2)$ wherein each $J^2$ independently is hydrogen, halogen, aliphatic, haloaliphatic, haloheteroaliphatic, heteroaliphatic, aromatic or any combination thereof;

E can be selected from hydrogen, halogen, aliphatic, haloaliphatic, haloheteroaliphatic, heteroaliphatic, aromatic or any combination thereof;

each Q can independently be selected from one electron pair donor, such as P, S, N, O or carbene having a formula: $C(J^3)_2$ wherein each $J^3$ independently is hydrogen, halogen, aliphatic, haloaliphatic, haloheteroaliphatic, heteroaliphatic, aromatic or any combination thereof; and each L can independently be selected from electron lone pair, O, S, SO, $C(J^4)_2$, $B(J^4)_3$ wherein each $J^4$ independently is hydrogen, halogen, aliphatic, haloaliphatic, haloheteroaliphatic, heteroaliphatic, aromatic or any combination thereof.

In some embodiments, p can be 1 and q can be 1. In certain embodiments, q is at least 1. In certain embodiments, m is at least 1. In certain embodiments, p is at least 1. In an additional embodiment, p can be 1 and q can be 1 to 10. In yet some embodiments, when r=0 and the bond between G and $Y^b$ is a single bond, then R' is a hydrogen and $Y^b=Y^a$. In additional embodiments, when r=0 and the bond between G and $Y^b$ is a double bond, then R' is absent, and E is present. In additional embodiments, when r=1, $A^1$ and $A^2$ together with E can be heterocyclic group, such as a 4-, 5-, 6- or 7-membered heterocyclic group, which can (but need not) comprise one or more heteroatoms in addition to E.

Still further, in some embodiments, each R, $J^1$, $J^2$, $J^3$, and $J^4$, if present (such as when the corresponding n variable is not 0), independently can be an aliphatic or aromatic ring comprising one or more electron-donating groups, one or more electron-withdrawing groups, or any combination thereof. Exemplary electron-donating groups may include, but are not limited to, alkoxy, amide, amine, thioether, hydroxyl, thiol, nitrile, acyloxy, aliphatic (e.g., alkyl, alkenyl, alkynyl or aryl), silyl, cycloaliphatic, aryl, or any combinations thereof. Exemplary electron-accepting groups may include, but are not limited to, aldehyde, ketone, ester, carboxylic acid, acyl, acyl halide, cyano, halogen, sulfonate, nitro, nitroso, quaternary amine, pyridinyl (or pyridinyl wherein the nitrogen atom is functionalized with an aliphatic or aryl group), alkyl halide, or any combinations thereof.

In some embodiments, each of the $J^1$, $J^2$, $J^3$ and $J^4$, if present, can independently be alkyl, alkenyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkeny-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkynyl-heteroaryl or any combination thereof. In some embodiments, the aryl and/or heteroaryl group can comprise one or more electron-donating groups, one or more electron-withdrawing groups, or any combination thereof.

In an independent embodiment, when G=nitrogen and the corresponding R'=hydrogen (if present), then at least one Q≠nitrogen and the corresponding L≠hydrogen or an electron-withdrawing group. In another independent embodiment, when G=nitrogen and the corresponding R'=hydrogen (if present), then at least one Q≠phosphorus and the corresponding L≠phenyl.

In particular embodiments, the polydentate macrocyclic ligands disclosed in Formula 1 can have a structure satisfying any one of the Formulas 1A, 1B, 1C and 1D below.

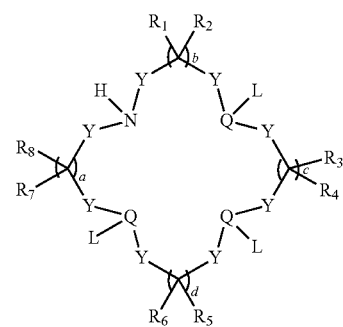

Formula 1A

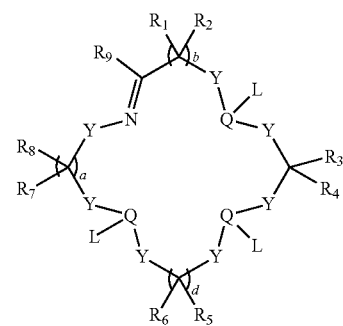

Formula 1B

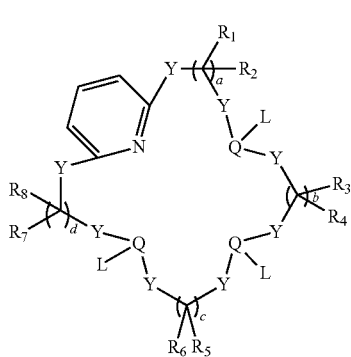

Formula 1C

Formula 1D

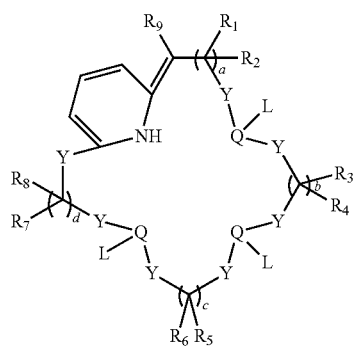

In particular disclosed embodiments of any of the above formulas, each of the $R_1$, $R_2$, $R_3$, $R_4$, $R_5$, $R_6$, $R_7$, $R_8$ and $R_9$, if present, can independently be alkyl, alkenyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkeny-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkynyl-heteroaryl or any combination thereof. In some embodiments, the aryl and/or heteroaryl group can comprise one or more electron-donating groups, one or more electron-withdrawing groups, or any combination thereof. The one or more electron-donating groups and the one or more electron-withdrawing groups can be as described above for Formula 1.

Exemplary ligands satisfying any one or more of Formulas 1, and 1A-1D are provided below.

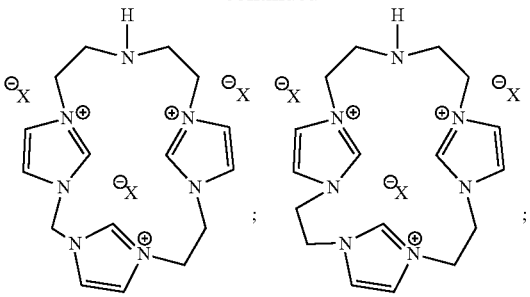

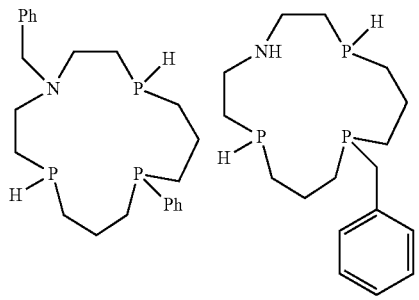

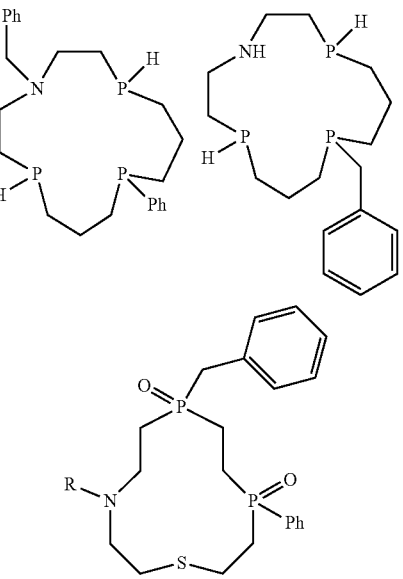

R= H, alkyl, substituted aryl or unsubstituted aryl, O, S, N or P

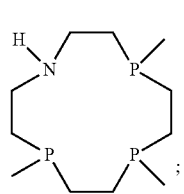

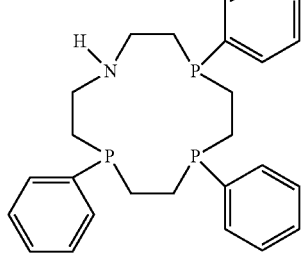

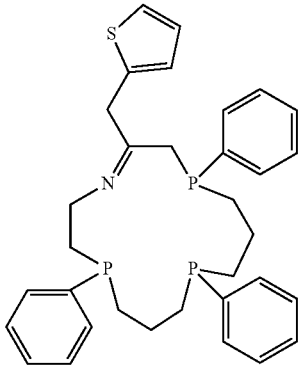

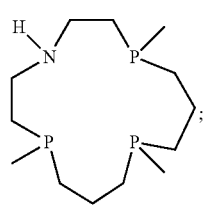

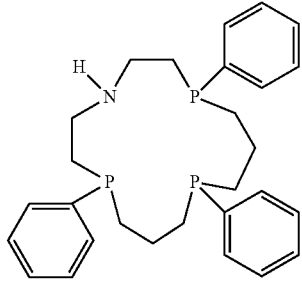

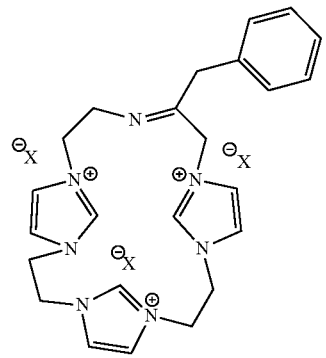

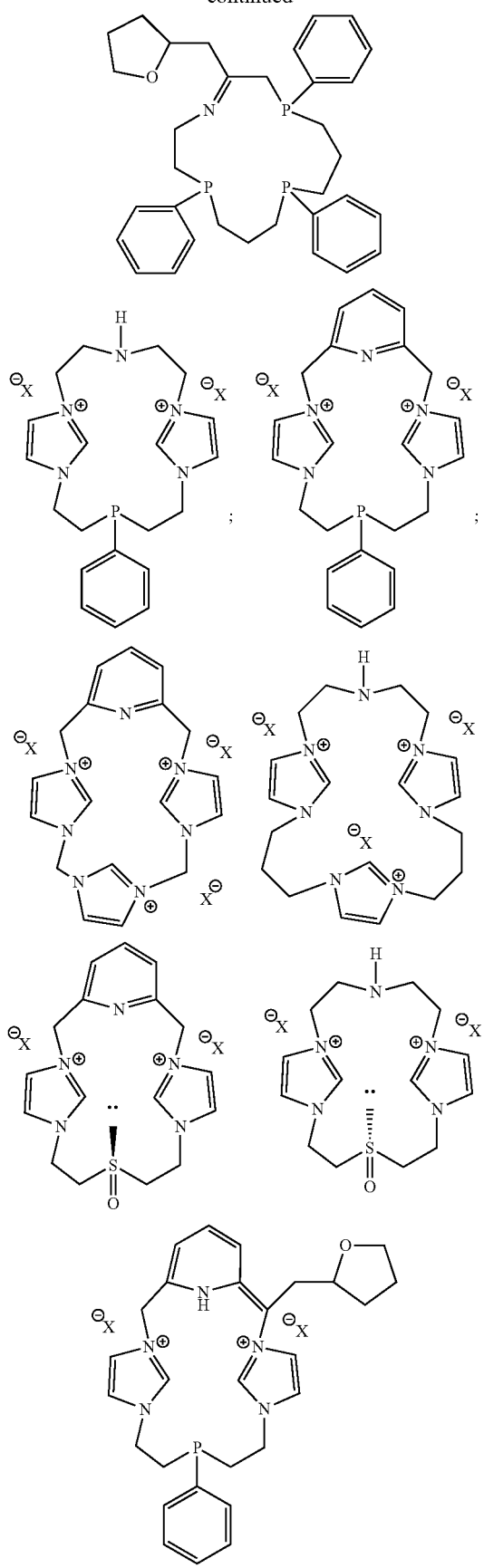
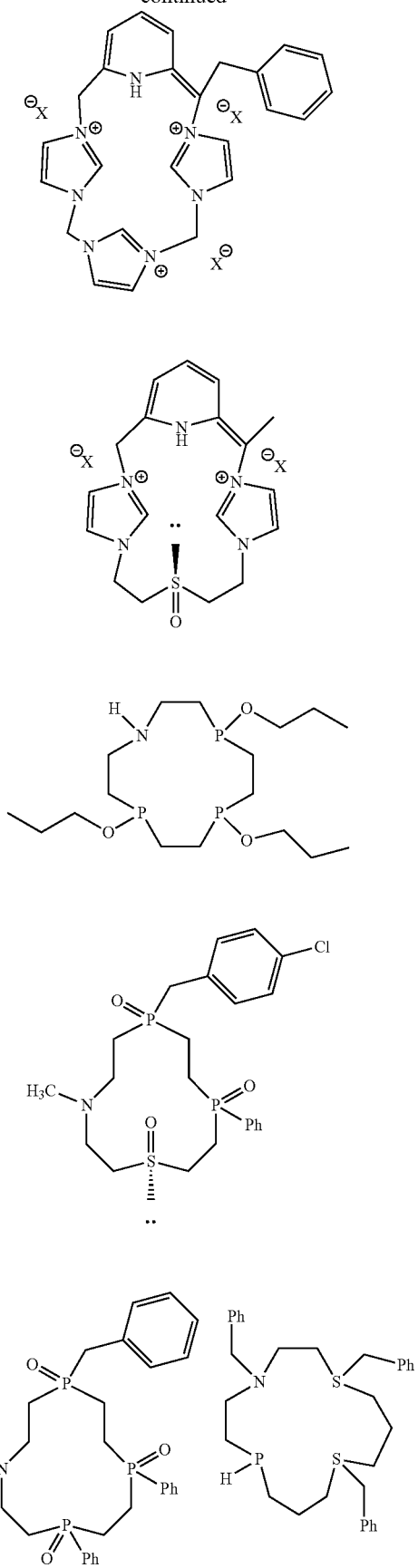

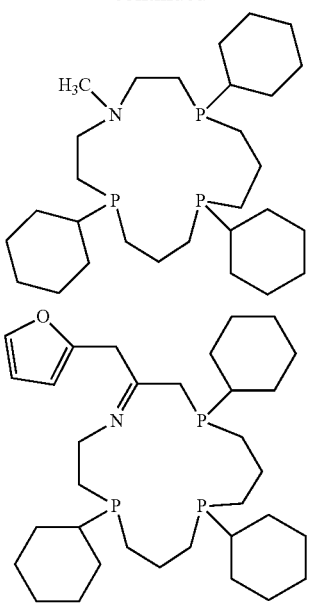

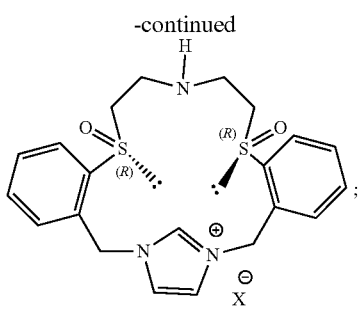

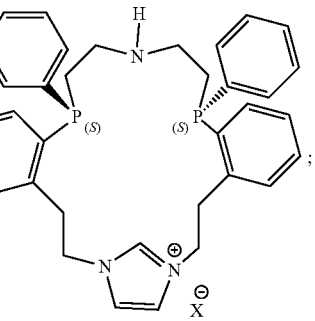

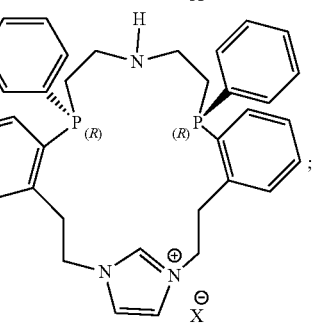

In some embodiments, one or more heteroatoms of the macrocyclic polydentate ligands disclosed herein, such as phosphorus, nitrogen, sulfur or carbon atoms may include one or more chiral groups that provide chirality to the resultant macrocyclic polydentate ligand.

Exemplary P-chirogenic ligands satisfying any one or more of Formulas 1, and 1A-1D are also provided below.

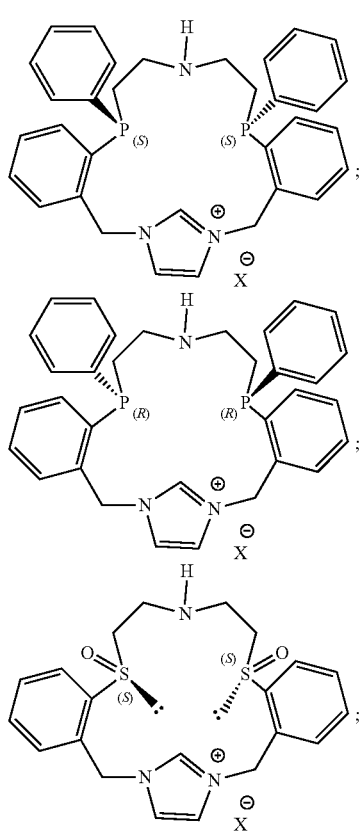

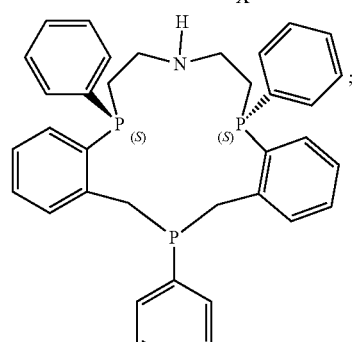

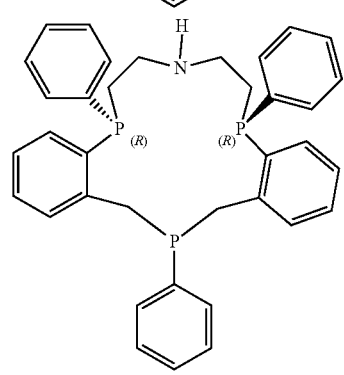

In an independent embodiment, the polydentate macrocyclic ligands satisfying any of the formulas above are not selected from the following compounds, their isomers and various possible derivatives:
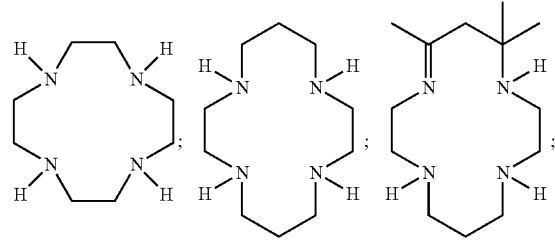
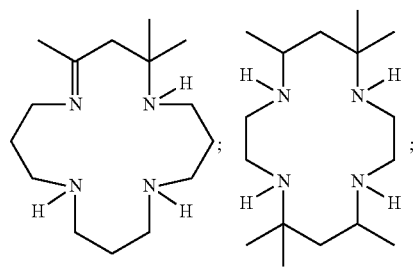
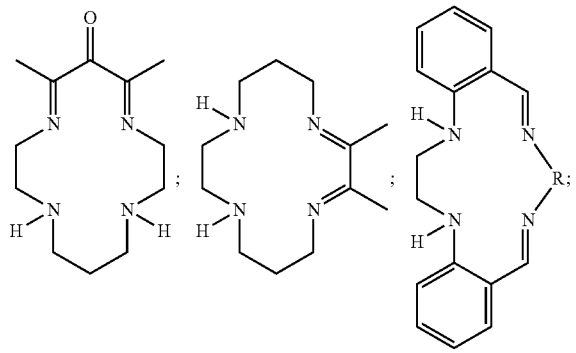
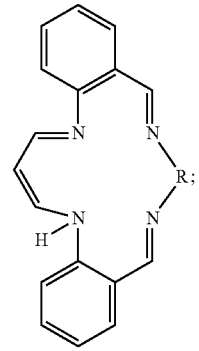
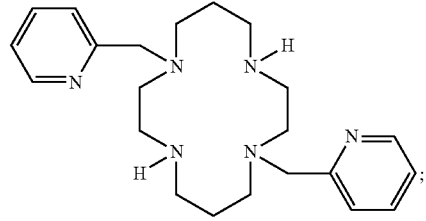
-continued
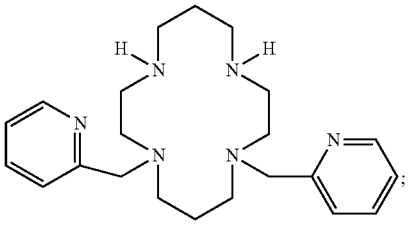
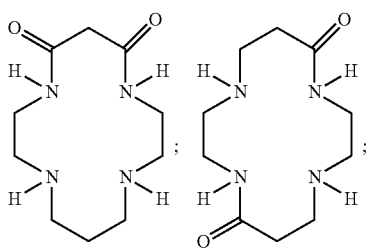
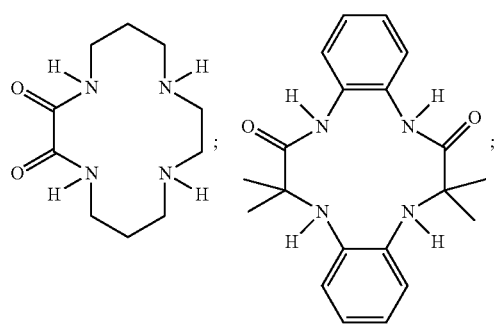
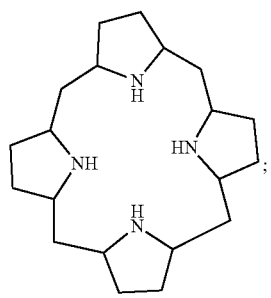
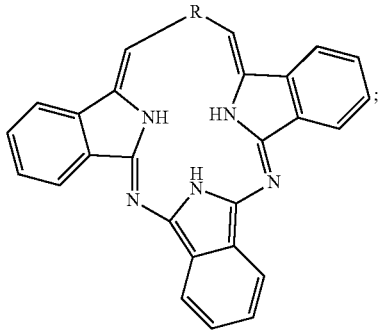

-continued

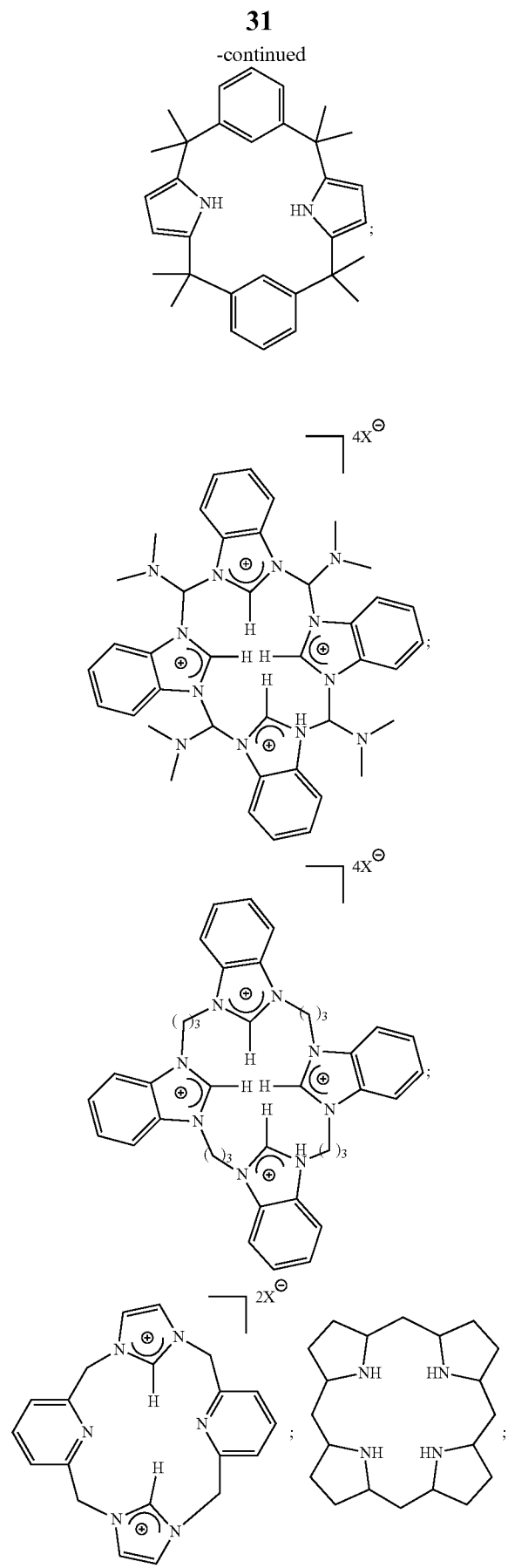

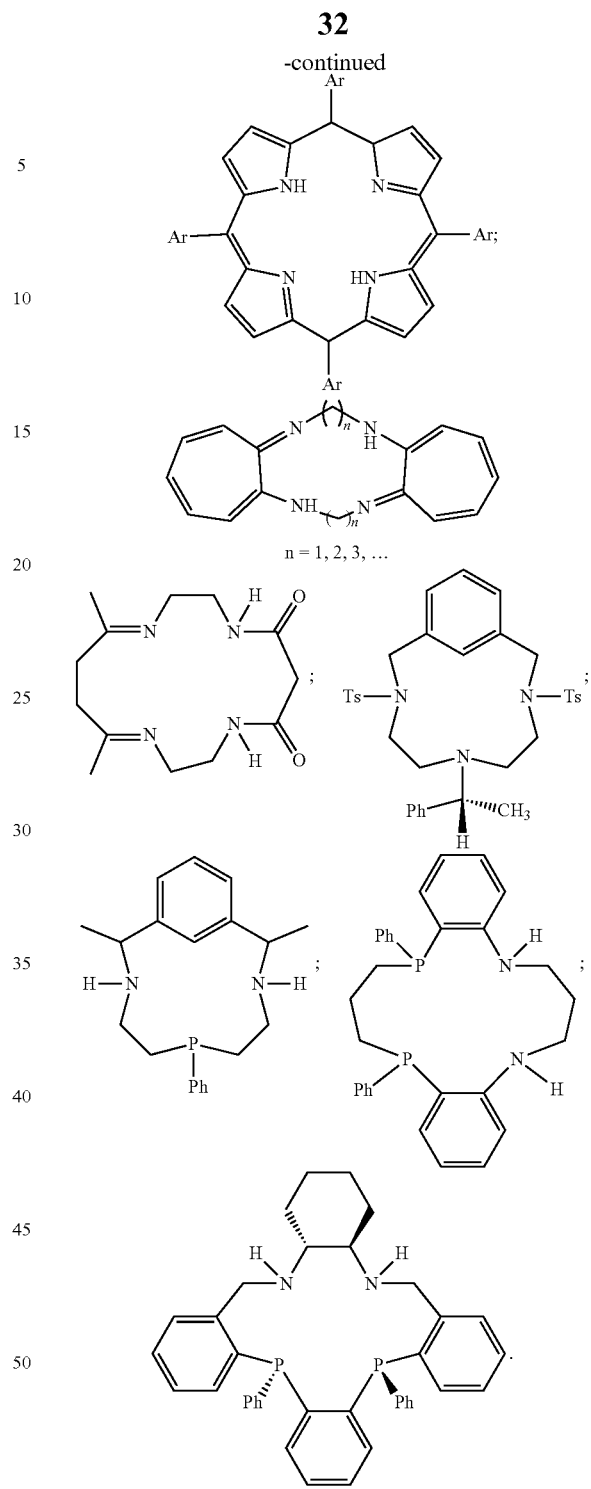

Further, for the ease of understanding, the ligands of Formulas 1 and 1A-1D, may be described in terms of their heteroatom functionality, for example, as NPPP-type, NCCC-type, NCCP-type, NCCS-type ligands, depending on the specific nature of the various variable recitations—Q, L, $Y^a$, $Y^b$, etc.

III. Methods of Making the Ligands

Disclosed herein are method embodiments for making the polydentate macrocyclic ligands disclosed herein. Certain method embodiments disclosed herein concern making nitrogen-based macrocyclic ligands containing one or more heteroatoms, such as phosphorus, sulfur atoms satisfying the formulas described above. In some embodiments, the synthesis of disclosed polydentate macrocyclic ligands utilizes one or more heteroatom-containing linkers as building blocks that are subsequently subjected to cyclization conditions via Michael-type addition reactions, radical-promoted addition reactions or the like.

As illustrated in Scheme 1 below, two heteroatom moieties can be used as precursors for a cyclization step to form the polydentate macrocyclic ligand.

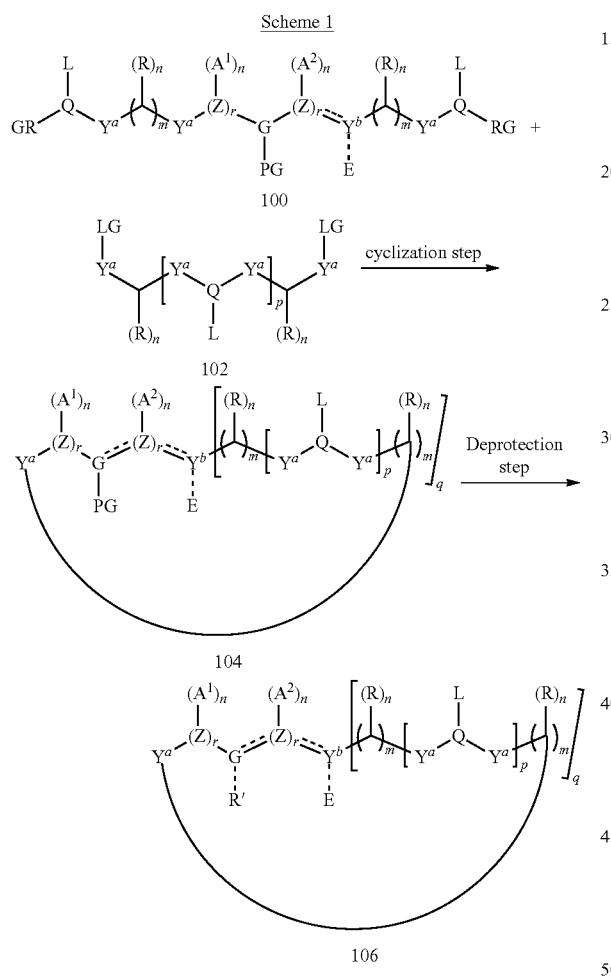

With reference to Scheme 1, each PG can be any suitable protecting group such as, ester group (e.g., Fmoc, Boc, Bn, TPS, or the like) and each RG can independently be any suitable reacting group such as, an ester (e.g., OEt), a halide (e.g., Cl, Br, or the like), an amide or the like, while each LG can be any leaving group such as, halide, phosphate ester or the like. Additionally, a person of ordinary skill in the art will understand, each of the RG and the LG present on the heteroatom moieties can be interchanged. Each of the other variable in Scheme 1 above are as disclosed for the Formula 1 described herein.

Additional method embodiments that can be used to make macrocyclic polydentate ligands are illustrated below in Schemes 2-5. With reference to Schemes 2-5, each of the various variable recitations are as disclosed for the Formulas 1A-1D described herein.

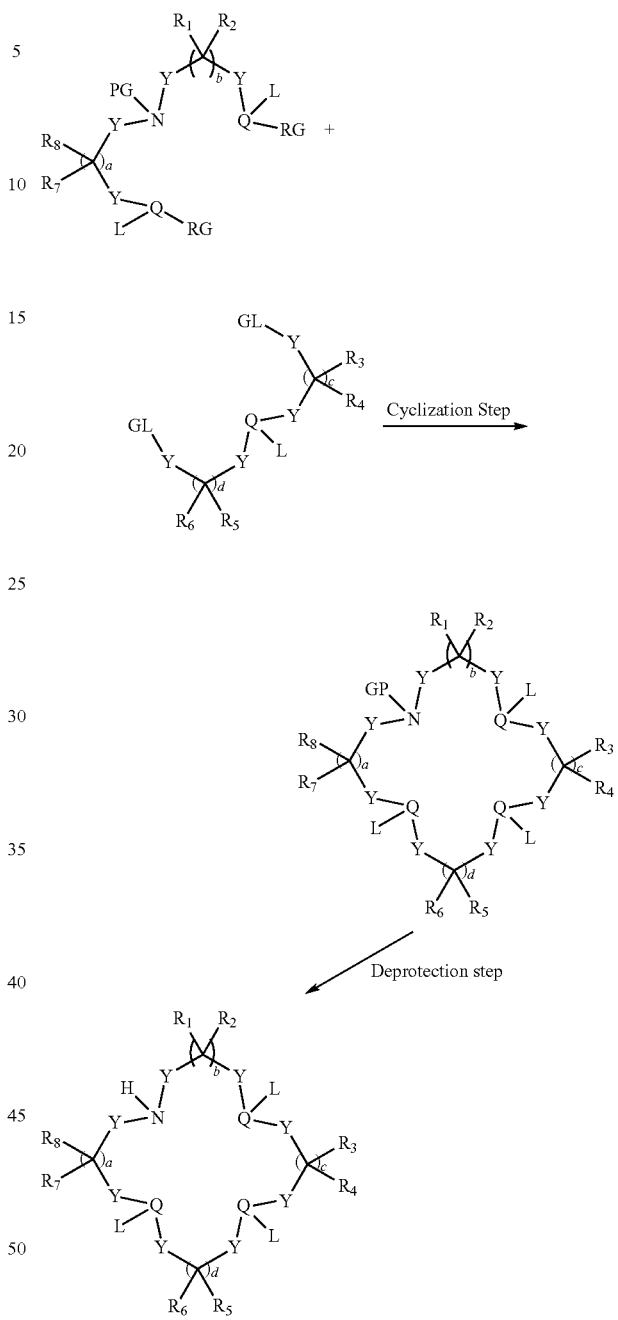

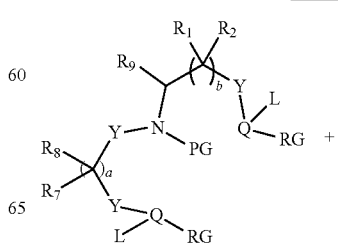

35
-continued
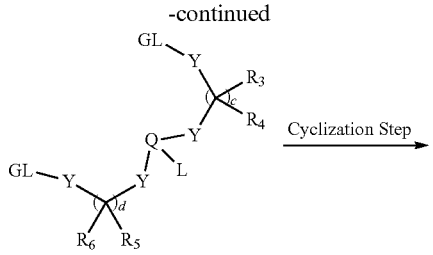
Cyclization Step
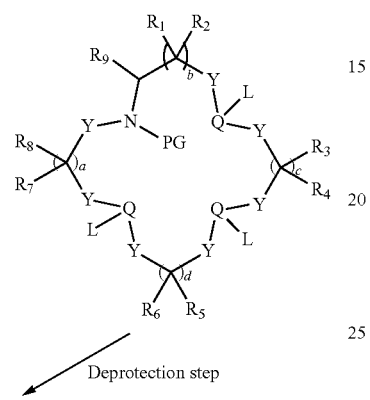
Deprotection step
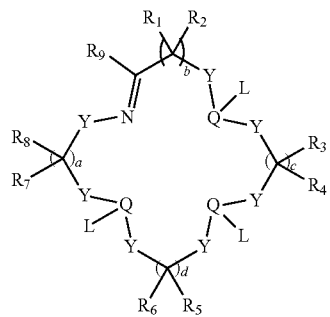
36
-continued
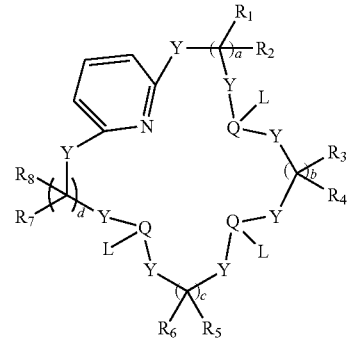
Scheme 5
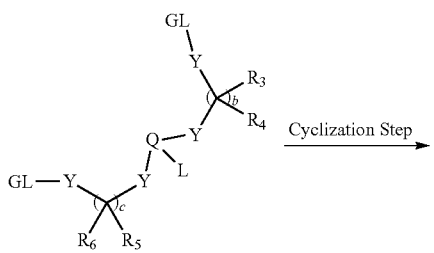
GL—Y
Cyclization Step
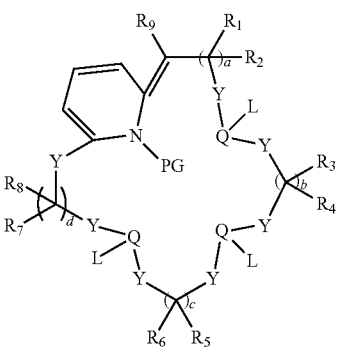
Deprotection step
Scheme 4
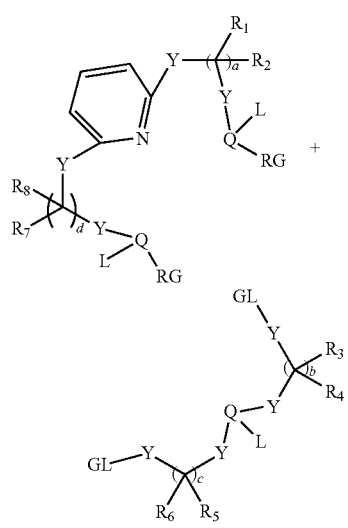

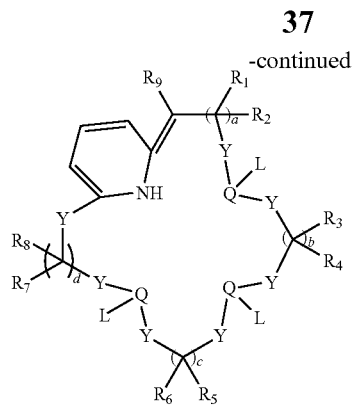
With reference to Schemes 2-5, each PG, RG and LG can independently be recited as disclosed for the Scheme 1 described herein. Exemplary embodiments of the above-described methods depicted in Schemes 1 and 2-5, respectively, are provided below in Schemes 6-9.
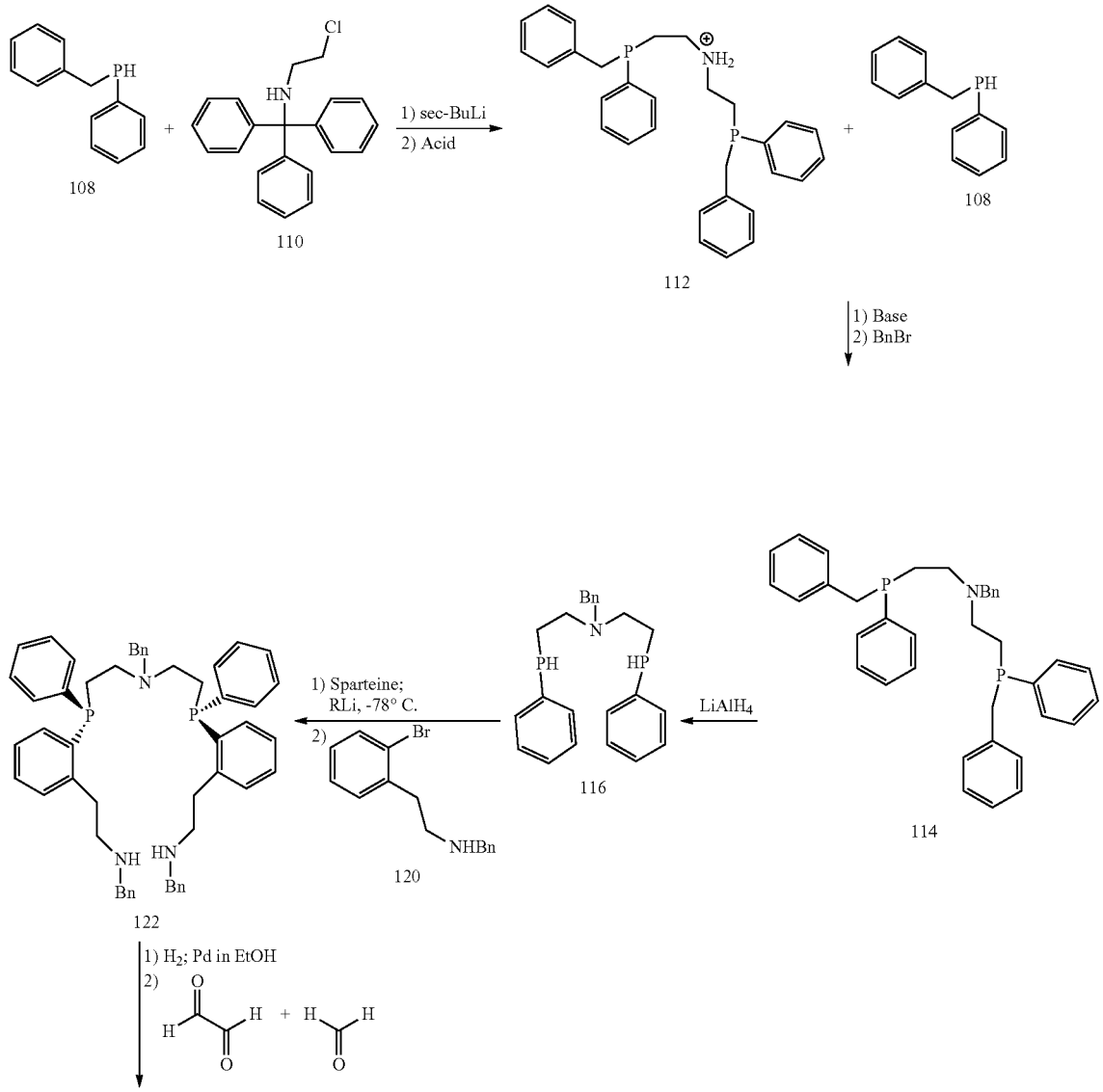
Scheme 6

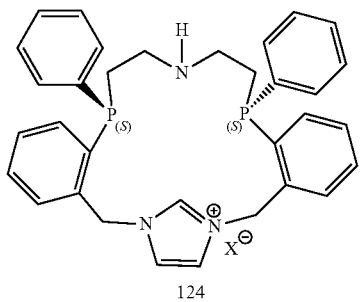
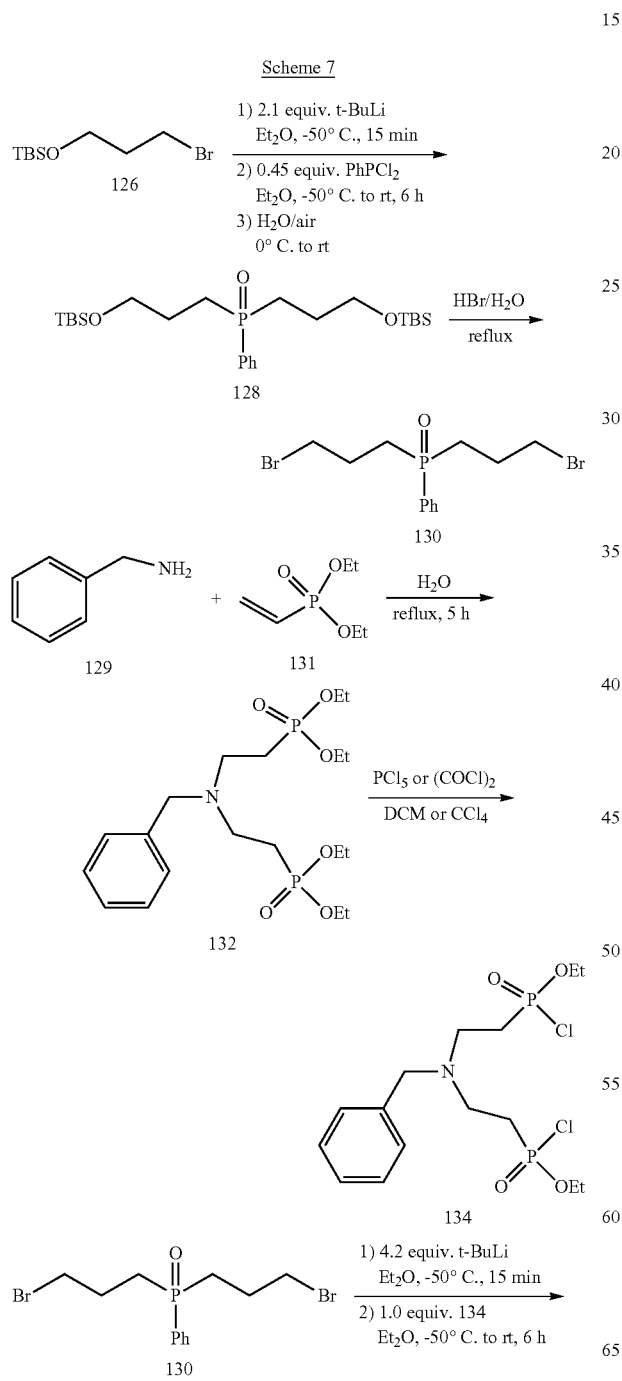
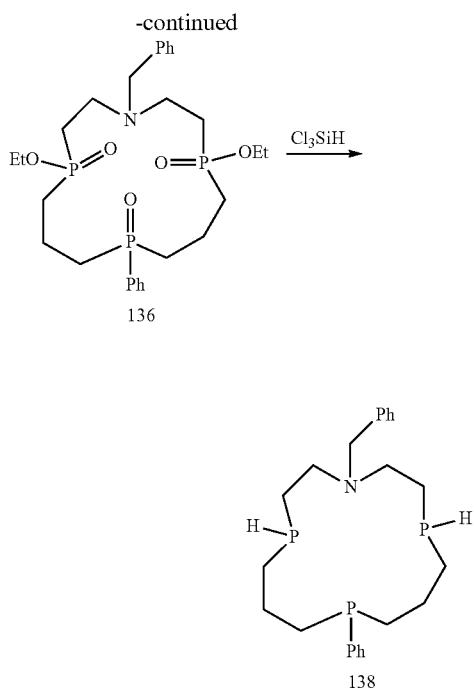

-continued

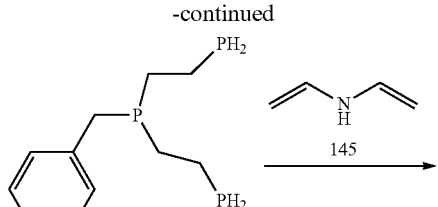

144

145

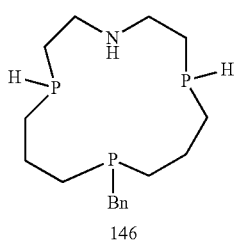

146

Scheme 9

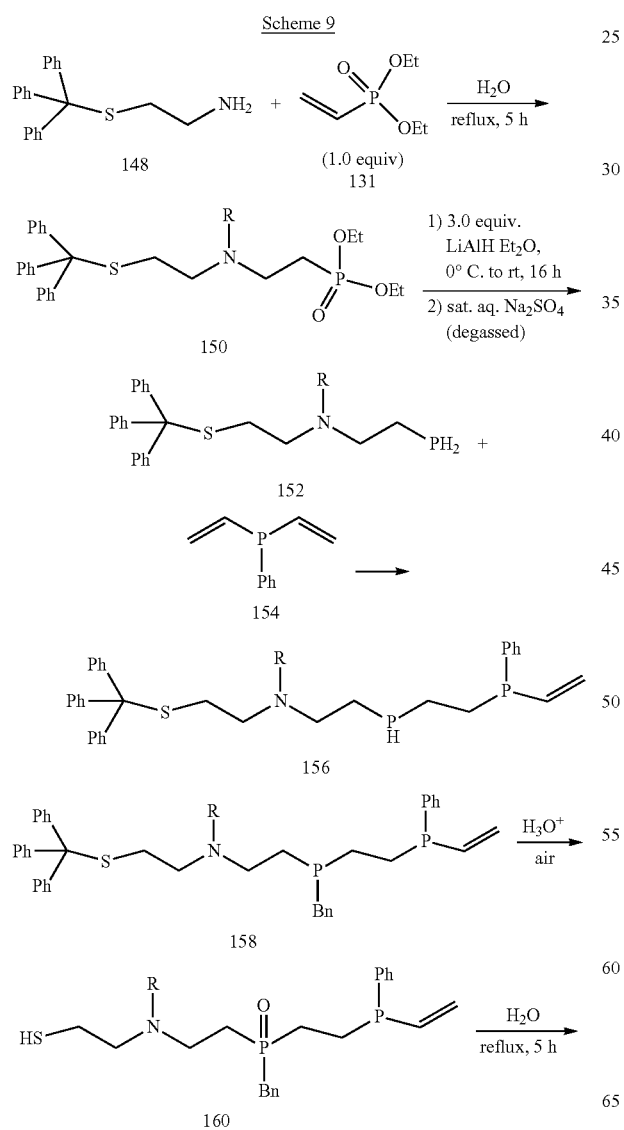

-continued

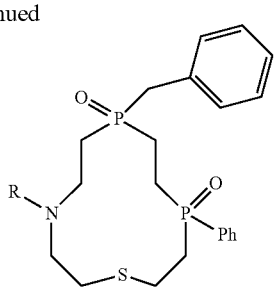

162

R = H, alkyl, unsubstituted aryl or substituted aryl; oxygen, Sulphur, nitrogen, phosphorous Additional representative method embodiments are also provides in the Examples of the present disclosure.

IV. Catalysts

Disclosed herein are embodiments of metal coordination complexes that comprise at least one of the ligands disclosed herein coordinated to at least one transition metal. A person of ordinary skill in the art will understand that the metal coordination complex and catalyst may be used interchangeably and are intended to refer to the organometallic entity. While the complexes are useful as catalysts, the use of the term catalyst should not be interpreted to limit the scope to the complexes to this purpose.

In one embodiment, the metal coordination complex can have a structure satisfying Formula 2.

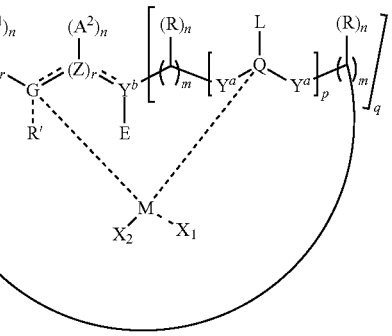

Formula 2

With reference to Formula 2, the following variable recitations can apply in any combination:

each of the $Y^a$, Z, $A^1$, G, R', $A^2$, $Y^b$, E, R, Q and L, as well as the integers m, n, p, q and r can be as recited above;

M can be any transition metal selected from Group 3 to Group 12, including the lanthanides and actinides; and each $X_1$ and $X_2$ independently can be selected from hydrogen, halogen, aliphatic, haloaliphatic, haloheteroaliphatic, heteroaliphatic, aromatic, aliphatic-aromatic, heteroaliphatic-aromatic, or any combination thereof.

In some embodiments, M can be selected from any transition metal of Group 4 to Group 12, and preferably a transition metal from Group 6 to Group 10 of the periodic table. Exemplary transition metals may include, but are not limited to, Ti, V, Zr, Hf, Cr, Mo, W, Mn, Re, Fe, Ru, Os, Co, Rh, Ir, La, Ni, Pd, Pt, Cu, Ag, Au, Zn, Sm or any combination thereof. In particular disclosed embodiments, the transition metals may include, or may be, Cr, Co, Cu, Fe, Mn, Mo, Ni, Os, Pd, Rh, Sm, W, or any subset combination thereof. In yet another particular disclosed embodiment, M of the metal coordination complexes may include, or may be, metals, such as Fe, Ru, Os, Co, Rh, or Ir, or any subset combination thereof. In a specific embodiment, the transition metal may a ruthenium (Ru) metal.

In some embodiments, some of the metal coordination complexes (i.e., catalysts) may be described more specifically in terms of their stoichiometries. For example, in some independent embodiments, the ratio of the ligand to transition metal may be 1 to 1. Further, the catalysts may include one or more transition metals per molecular entity. For example, the ligands may bridge one or more transition metal centers to form polydentate ligands, such as monodentate, bidentate, tridentate, or tetradentate ligands with respect to any individual transition metal center. Additionally, depending on the variable integer m (i.e., m=1, 2, 3 or the like), the metal coordination complexes may be described more specifically in terms of their isomerism. For example, each catalyst may be either have trans- or cis- geometry or both.

Additionally, in some embodiments, depending on the nature of the transition metal M and ligand combination, each of the $X_1$ and $X_2$ that are coordinated to M independently can be selected from one or more ligand substituents, such as anionic ligands, neutral ligands, or cationic ligands. Exemplary anionic ligands may include, but are not limited to, aliphatic or aromatic groups substituted with one or more halides (e.g., F, Cl, Br, I), nitrites, nitrates, sulfates (e.g., sulfato or thiosulfato), sulfites, alkoxy (e.g., methoxy or benzyloxy), aryloxy (e.g., phenoxy), carboxylato (e.g., mono-, di-, or trifluoroacetic acid), hydrides (e.g., oxo, hydroxo), hydroxy, cyanides (e.g., cyano or isocyano), thiocyanides (e.g., thiocyanato, or isothiocyanato), OTf (triflate), OTs (tosylate), $PF_6$, phosphate or borane ($BH_4$). In a particular disclosed embodiment, the anionic ligand is chloro.

Exemplary neutral ligands may include, but are not limited to, aliphatic or aromatic groups substituted with functional groups such as, nitriles (e.g., alkyl or aryl nitriles), amines (e.g., alkyl, aryl or unsubstituted primary, secondary or tertiary amines), pyridinyl (or pyridinyl wherein the nitrogen atom is functionalized with an aliphatic or aryl group), carbonyl (CO), ethers (e.g., alkyl, cycloaliphatic (e.g., tetrahydrofuran) or aryl ethers), nitroso (NO), phosphines, phosphites, phosphine oxides, sulfoxides. Exemplary cationic ligands may include, but are not limited to, nitrosyl ($NO^+$), tropylium ($C_7H_7^+$) or the like.

In particular embodiments, the metal coordination complexes disclosed in Formula 2 can have a structure satisfying any one of the Formulas 2A-2I below.

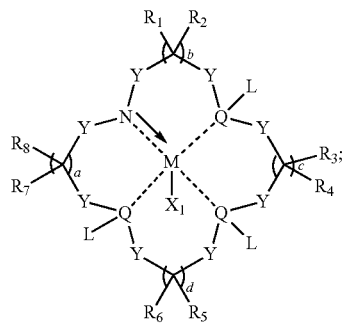

Formula 2B

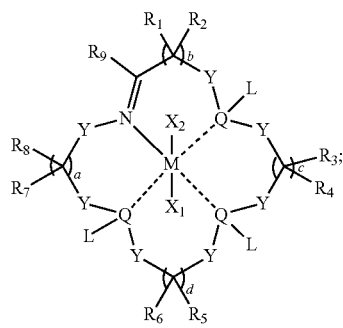

Formula 2C

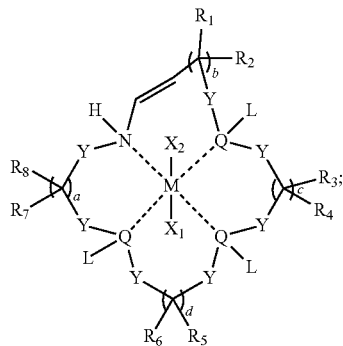

Formula 2D

Formula 2A

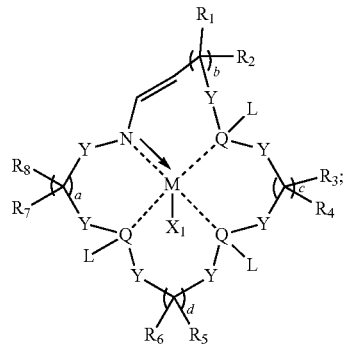

Formula 2E

-continued

Formula 2F
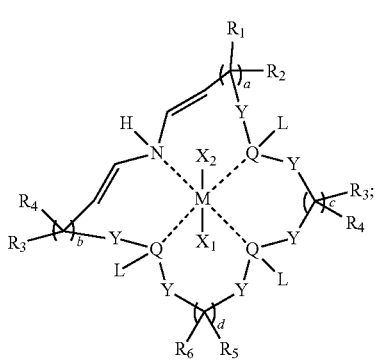

Formula 2G
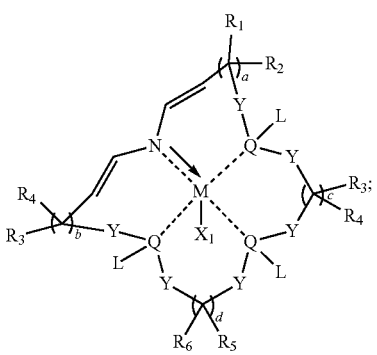

Formula 2H
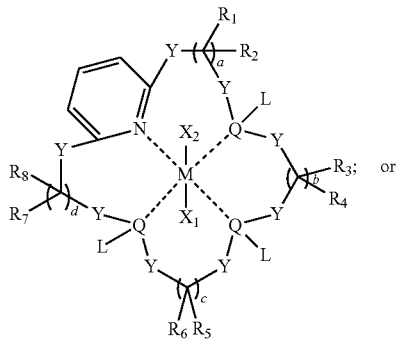

Formula 2I
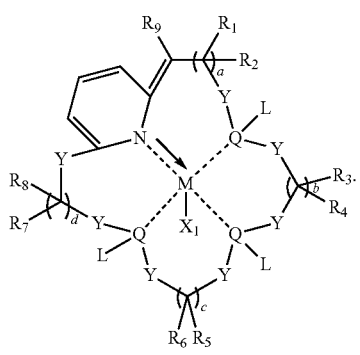

wherein:

Q is selected from one electron pair donor such as phosphorus, sulfur, nitrogen, oxygen, or carbon (carbene);

$X_1$ and $X_2$ independently are an anionic substituent selected from F, Cl, Br, I, H, OTf, OH, OR (R is any alkyl), $BH_4$ or $PF_6$;

L is selected from a lone pair (or its absence), oxygen, $BH_3$ and similar, or substituents from among a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

Y is selected from a functionality containing a heteroatom such as NH, O, S, PR, an optionally substituted $CH_2$ group or its absence, wherein R is selected from hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

a, b, c, and d can independently be an integer selected from 0, 1, 2, 3, 4, 5, 6, 7, 8. 9 or 10;

M can be any transition metal selected from Group 3 to Group 12, including the lanthanides and actinides; and $R_1$, $R_2$, $R_3$, $R_4$, $R_5$, $R_6$, $R_7$, $R_8$, and $R_9$ are independently at each occurrence a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, a substituted or unsubstituted arylalkyl or a combination thereof.

In a specific embodiment, when M is a ruthenium metal, the metal coordination complex can have a structure satisfying one or more of Formulas 3A-3I:

Formula 3A
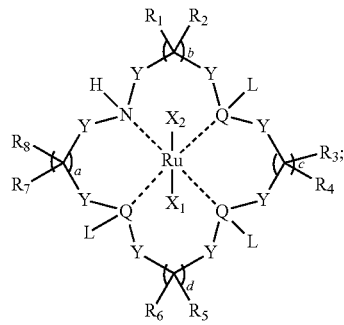

Formula 3B
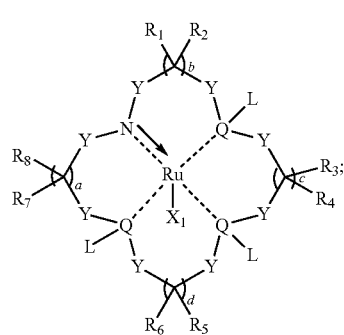

Formula 3C
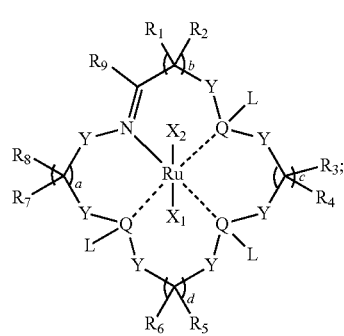

Formula 3D

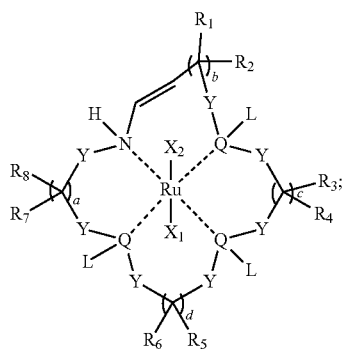

Formula 3E

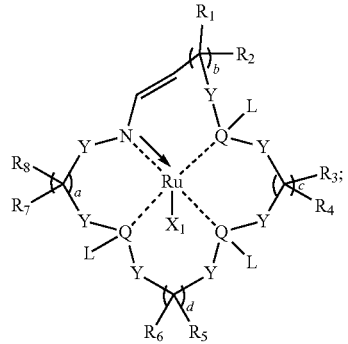

Formula 3F

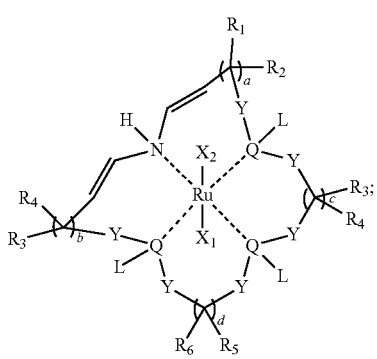

Formula 3G

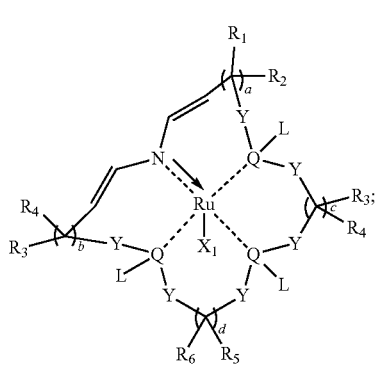

Formula 3H

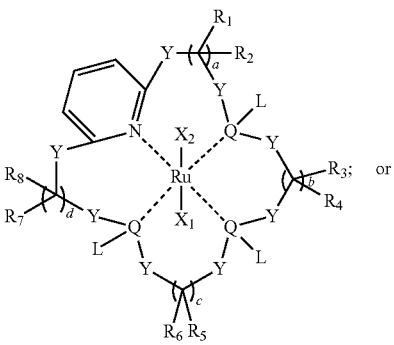

Formula 3I

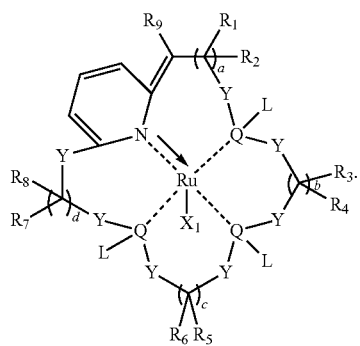

With reference to these formulas, each of the variables above are as disclosed for the Formulas 2 and 2A-2I described herein.

In particular disclosed embodiments of any of the above formulas, and as described above, each of the $R_1$, $R_2$, $R_3$, $R_4$, $R_5$, $R_6$, $R_7$, $R_8$ and $R_9$, if present, can independently be alkyl, alkenyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkeny-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkynyl-heteroaryl or any combination thereof. In some embodiments, the aryl and/or heteroaryl group can comprise one or more electron-donating groups, one or more electron-withdrawing groups, or any combination thereof. The one or more electron-donating groups and the one or more electron-withdrawing groups can be as described above for Formula 1.

In particular disclosed embodiments, the catalysts may comprise ruthenium having an empirical formula Ru(NPPP)$X_1X_2$, Ru(NCCC)$X_1X_2$, Ru(NCCP)$X_1X_2$, wherein NPPP, NCCC, or NCCP is a NPPP-type, NCCC-type, or NCCP-type macrocyclic ligand, respectively; $X_1$ and $X_2$ are independently formally anionic ligands (H, halide, OTf, $BH_4$, $PF_6$, and the like).

Exemplary metal coordination complexes meeting Formulas 2, 2A-2I and 3A-3I, respectively, are provided below:

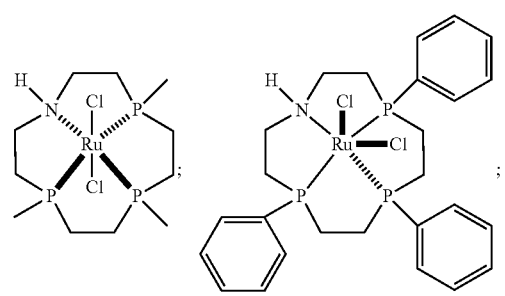
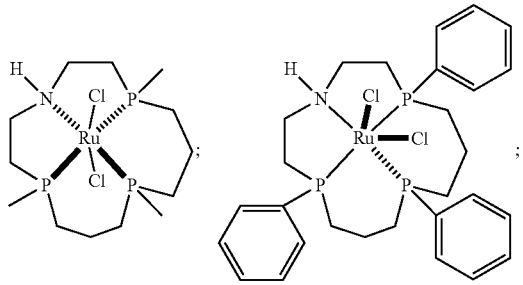
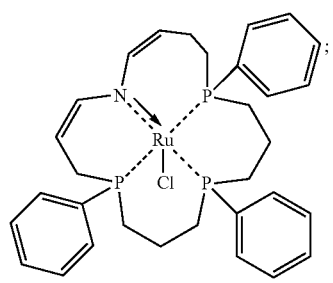
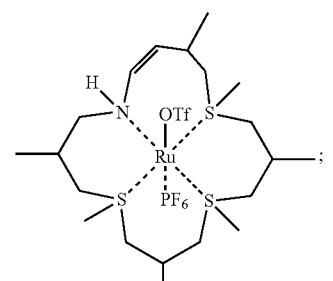
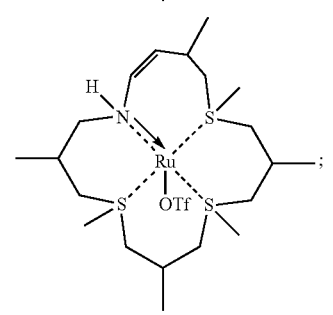
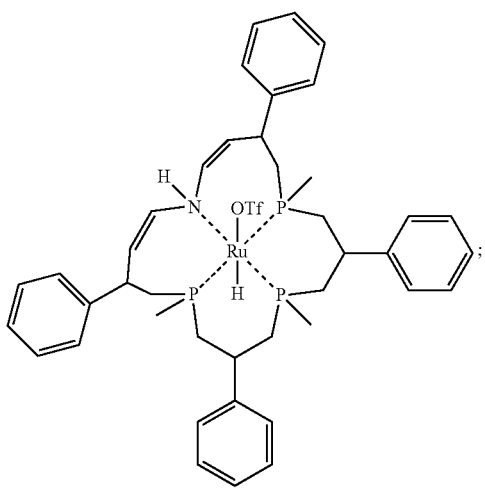
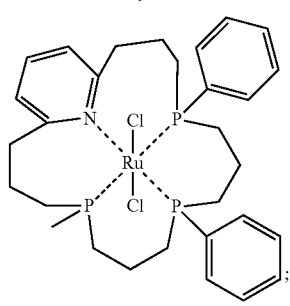

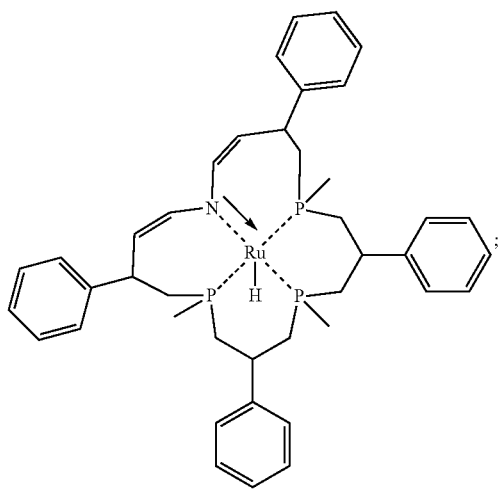
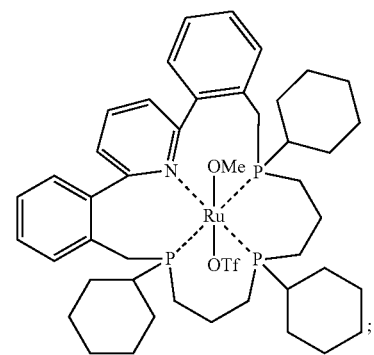
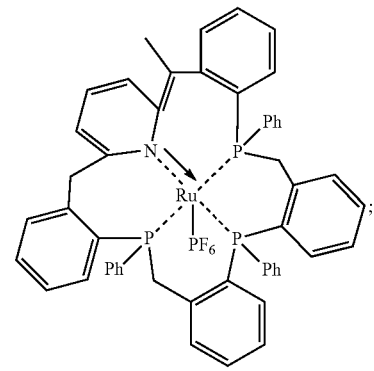
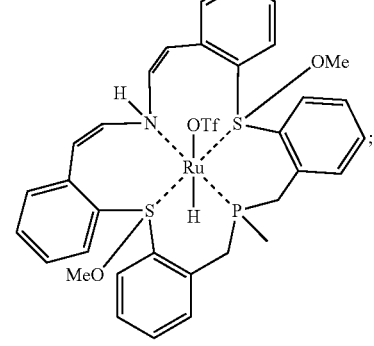
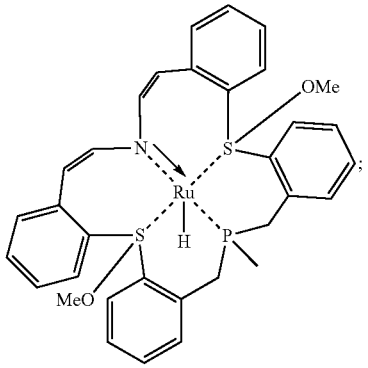
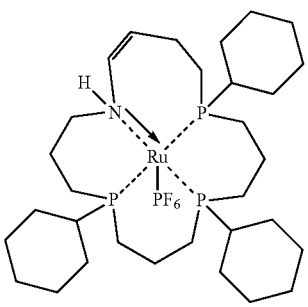
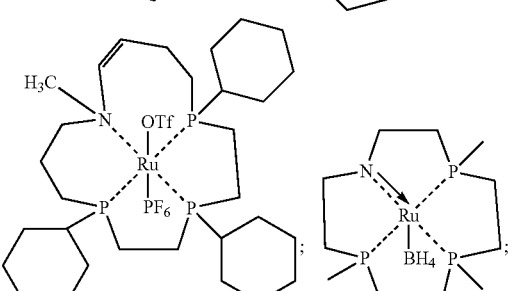
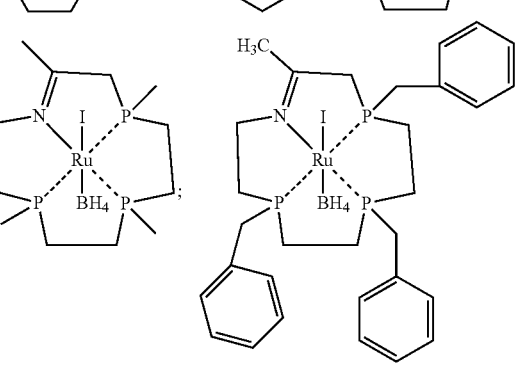
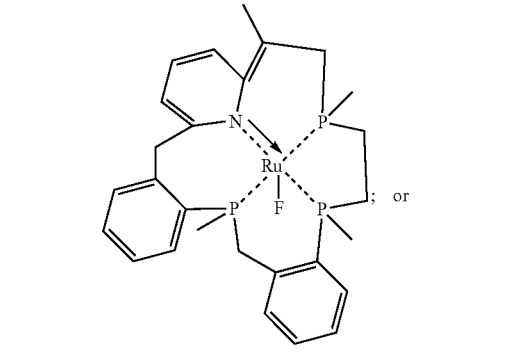

-continued

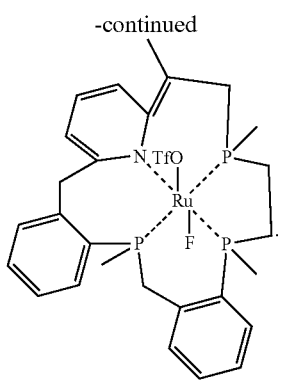

V. Methods of Making the Catalysts

Methods of making the catalysts are disclosed herein. Representative methods of making the catalysts disclosed herein are illustrated in the following schemes. In some embodiments, the method comprises reacting the ligand with a metal-containing precursor to provide metal coordination complex, as illustrated in Scheme 10. In one example, the ligand and the metal-containing precursor may be refluxed together in the presence of a solvent. In another example, the ligand may also be reacted with the metal-containing precursor in a solvent at a room temperature. Exemplary metal-containing precursors may include, but are not limited to, [RuCl$_2$(PPh$_3$)$_3$], [RuCl$_2$(DMSO)$_4$], [RuCl$_2$($\eta^4$-COD)]$_n$/L, [IrCl($\eta^2$-COE)$_2$]$_2$ and the like, depending on the desired metal of the metal coordination complex. Exemplary solvents may include, but are not limited to, dichloromethane, chloroform, 1,2-dichloroethane, THF, benzene, toluene, acetonitrile, dioxane, methanol, ethanol, or the like. In yet another additional embodiment, the metal coordination complex can be obtained in an in-situ reaction without isolating the ligand.

Scheme 10

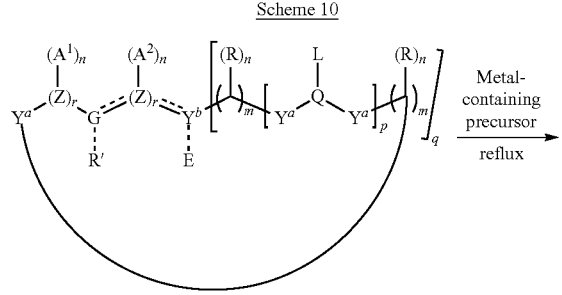

164

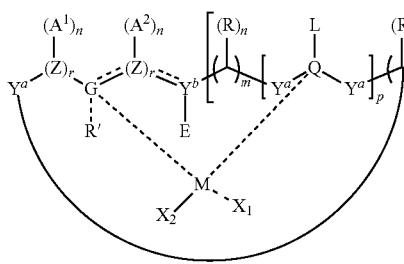

166

Additional method embodiments that can be used to make the metal coordination complexes are illustrated below in Schemes 11-14. In particular embodiments disclosed herein, each of the macrocyclic ligands, upon reacting with the metal-containing precursor, results in one or more isomers. With reference to Schemes 11-14, each of the illustrated variables can be recited as described above for the metal coordination complex formulas disclosed herein.

Scheme 11

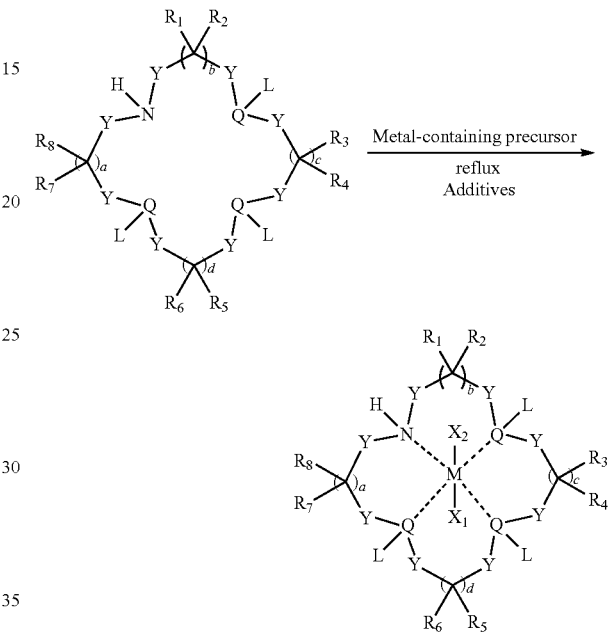

Scheme 12

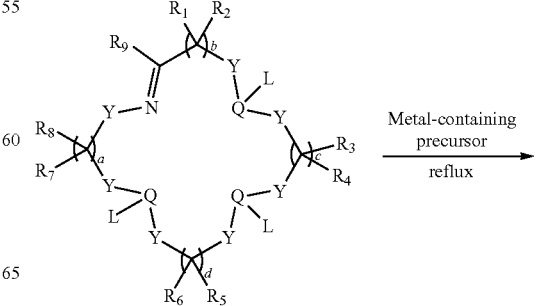

-continued
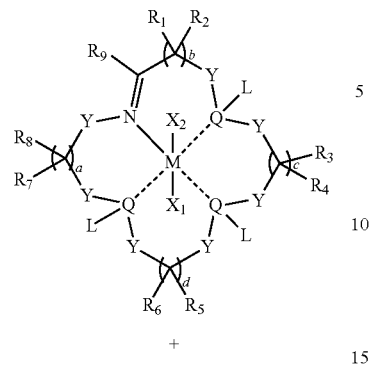
+
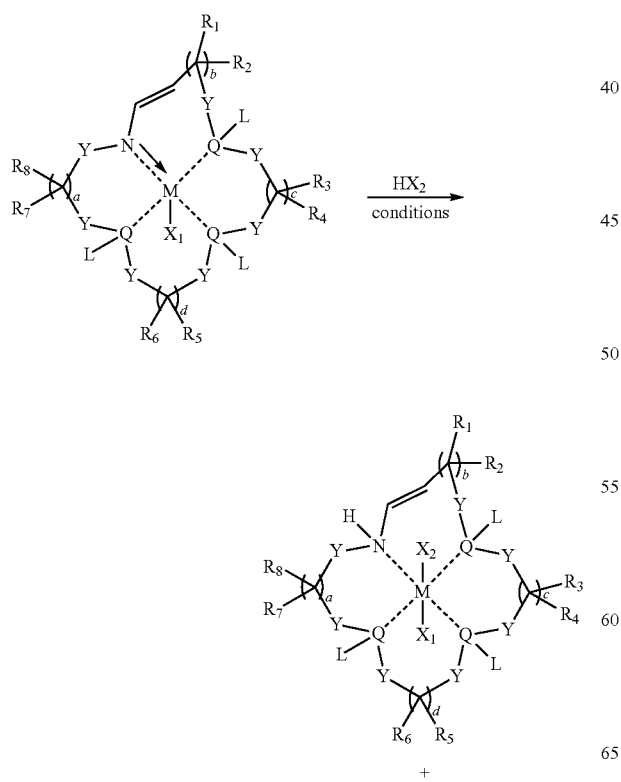
-continued
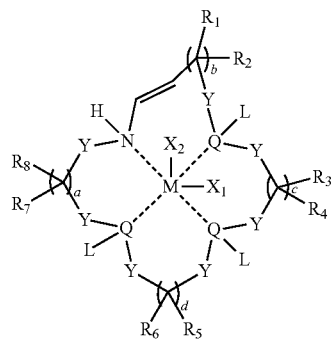
Scheme 14
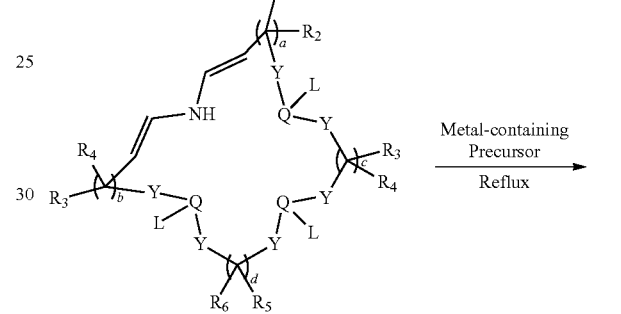
Exemplary embodiments of the above-described methods depicted in Schemes 10 and 11-14 are provided below in Schemes 15-19.

Scheme 15
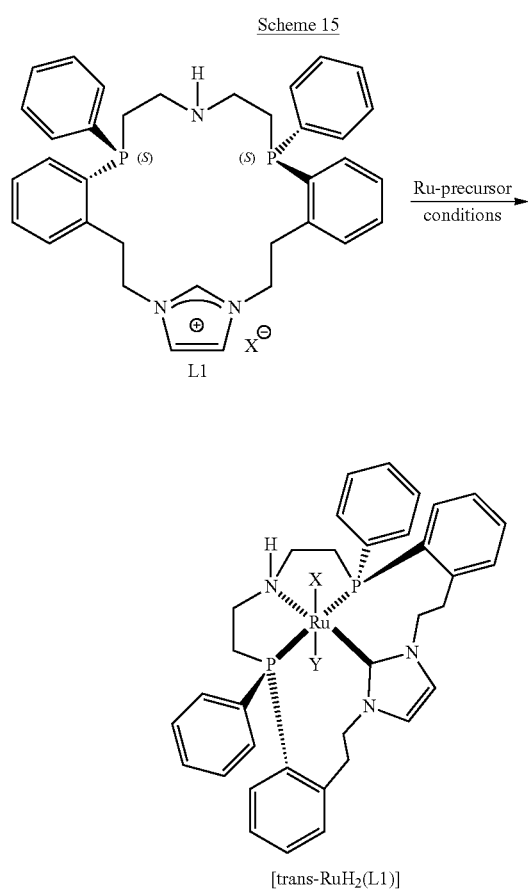
[trans-RuH₂(L1)]
[cis-RuH₂(L1)]
Scheme 16
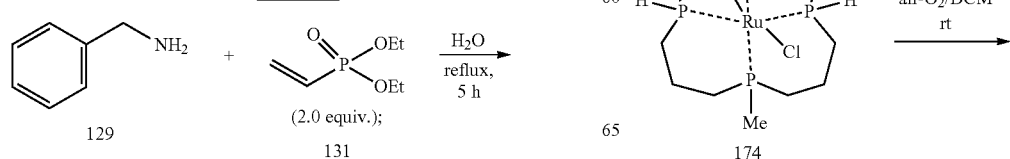
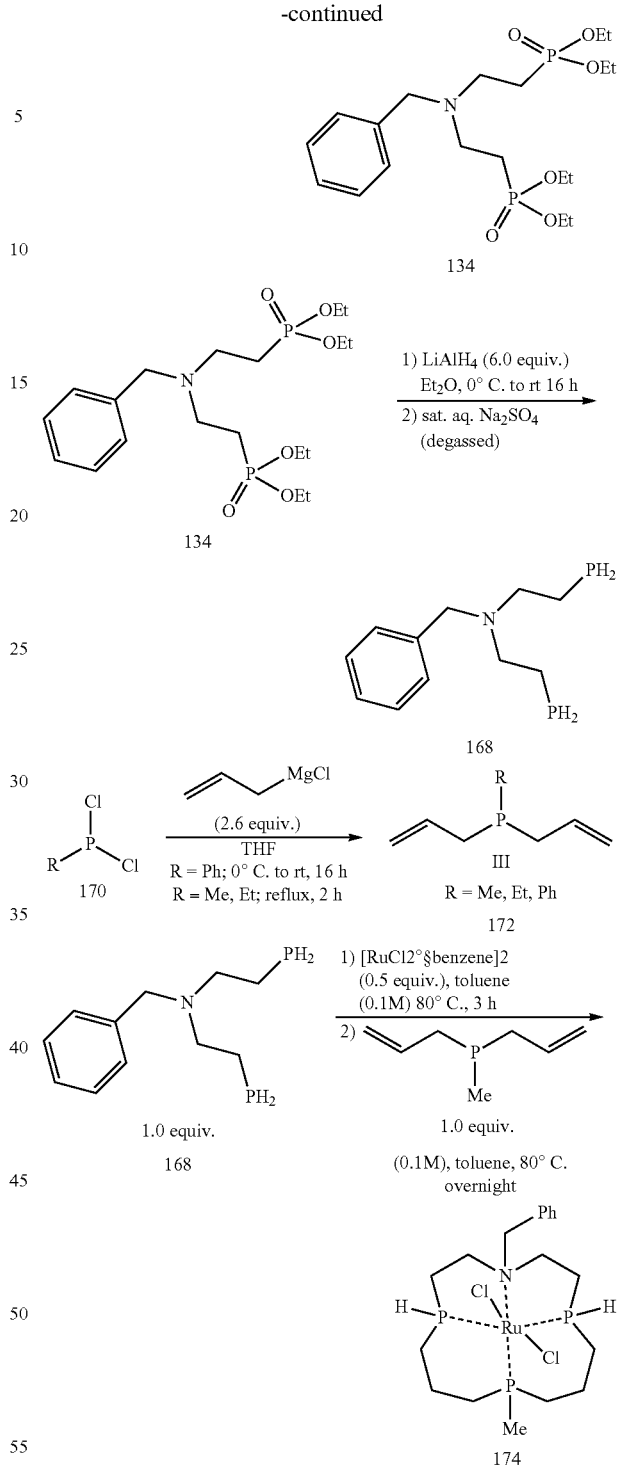

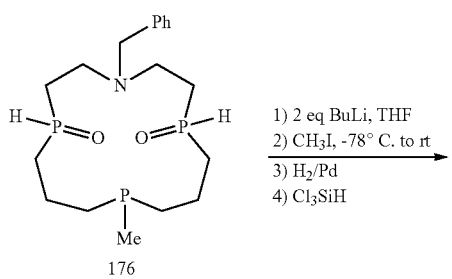

176

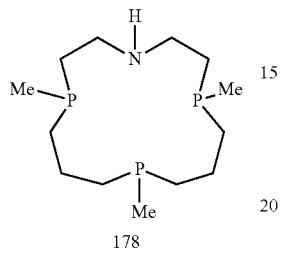

178

Scheme 17

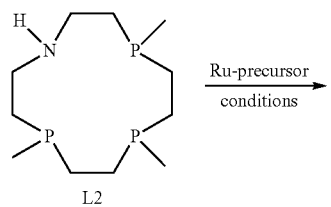

L2

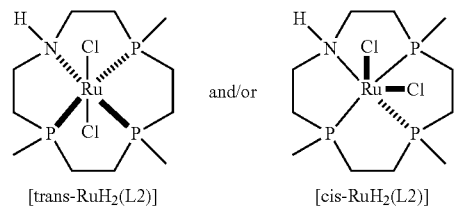

[trans-RuH₂(L2)]   [cis-RuH₂(L2)]

Scheme 18

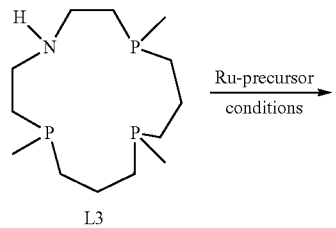

L3

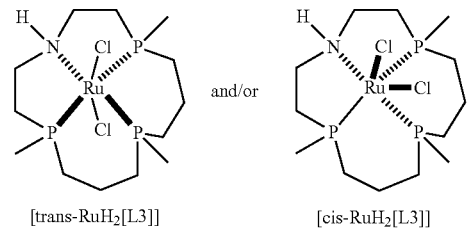

[trans-RuH₂[L3]]   [cis-RuH₂[L3]]

Scheme 19

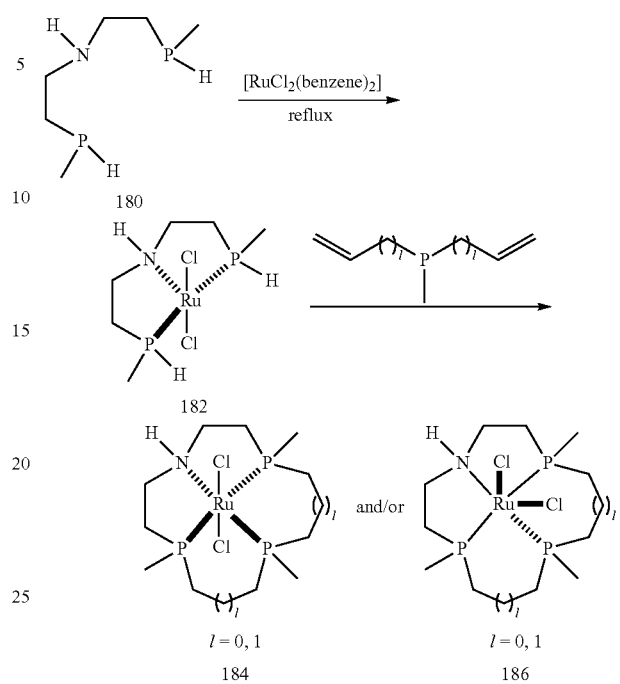

180

182

$l = 0, 1$   $l = 0, 1$
184          186

VI. Catalytic Reactions

Disclosed herein are the embodiments of the using the metal coordination complexes disclosed herein. In some embodiments, the metal coordination complexes may be utilized for modifying one or more functional groups of a reactant (referred to herein as a substrate). For example, a substrate having one or more functional groups is reacted with a reactant in the presence of the metal coordination complexes described herein to modify one or more functional groups of the substrate. In some embodiments, such modifications may include, but are not limited to, hydrogenation reactions; transfer hydrogenation of organic compounds containing unsaturated functionalities (C=O, C=N, C=C, and the like); reduction of $CO_2$; dehydrogenation of alcohols, carboxylic acids, boranes and other compounds; various dehydrogenative couplings; C—C bond forming reactions; alkylation of amines; hydration or the like.

In particular disclosed embodiment, the reactant in the hydrogenation reactions may include hydrogen gas or other sources of hydrogen (e.g., a secondary alcohol, formic acid, or a combination thereof) to accomplish these transformations, and the catalyst may be present in the corresponding reaction mixture either as delivered to the reaction or as derived in situ from the presence of catalyst complex under the reaction conditions.

In certain embodiments, the methods comprise reacting a substrate (e.g., an organic substrate) having an unsaturated bond with a reactant, such as, hydrogen gas (e.g., dihydrogen, a secondary alcohol, formic acid, or a combination thereof) in the presence of the catalysts disclosed herein, under reaction conditions sufficient to hydrogenate the unsaturated bond. The unsaturated bond of the organic substrate can independently be at least one of a >C=C< (alkenyl), —C≡C— (alkynyl), >C=O, >C=N—, —C≡N, —N=O, or —N=N— (azo) bond. In such cases, the organic substrate having the unsaturated C=C, C=O, or C=N bond comprises an aldehyde, ketone, an imine, an imide, a carboxylic acid, an acid anhydride, an ester, an amide (carboxamide), a carbonic anhydride ester (carbonate), a carbamic acid ester (carbamate), a urea or the like. In particular disclosed embodiments, organic substrates having carbonyl or imine double bonds are particularly susceptible for one or more transformations in the presence of these catalysts. The unsaturated bonds of the substrates may be functionalized or non-functionalized, conjugated or non-conjugated. Other bifunctional catalysts have been shown to exhibit exceptionally high C=O/C=C chemoselectivity, and similar selectivity can reasonably be expected with the catalysts described herein.

In additional disclosed embodiments, and especially but not exclusively those in which the catalysts are bifunctional (i.e., the ones bearing ligand NH functionalities), the catalysts disclosed herein can independently catalyze the hydrogenation of ketones (i.e., the carbonyl groups of the ketones) and imines. Further, in additional disclosed embodiments, the metal coordination complexes (i.e., catalysts) containing chiral ligands can be utilized for the hydrogenation of an asymmetric ketone (i.e., carbonyl groups of the ketones) as well as stereoselective catalytic C—N and C—C bond-forming reactions (e.g., aziridination of alkenes). In additional embodiments, the catalysts described herein can be utilized for one or more reactions, such as the asymmetric transfer hydrogenation of ketones (i.e., carbonyl groups of the ketones) and imines, asymmetric hydrogenation of polar functionalities, asymmetric Michael reactions of 1,3-dicarbonyl compounds with cyclic enones and nitroalkenes, aerobic oxidative kinetic resolution of racemic secondary alcohols, asymmetric hydration of nitriles or the like. Additionally, the catalysts described herein may also be used for hydrogenation of $CO_2$. In an exemplary embodiment, carbon dioxide can react with hydrogen in the presence of the catalysts disclosed herein under reaction conditions sufficient to hydrogenate the unsaturated bond resulting in a corresponding primary alcohol (e.g., methanol). In additional embodiments, the catalysts disclosed herein can also be utilized in one or more transformations, such as carbonate and ester hydrogenation, and various acceptor less dehydrogenations. Under certain well-understood conditions, the catalysts disclosed herein may act as precatalysts in $CO_2$ hydrogenation and electroreduction, ester hydrogenation, ketone transfer hydrogenations, the solvolysis of ammonia borane, and the amination of aliphatic alcohols.

Although not critical to the invention, a person of ordinary skill in the art will understand that these reactions may be conveniently conducted in polar or non-polar solvents in the presence of inorganic base which can function as co-catalysts. Exemplary solvents that can be employed in these transformations may include, but are not limited to, aromatic hydrocarbons (such as, aryl (e.g., benzene) or heteroaryl solvents (e.g., pyridine)), alcohols, nitriles, ethers, or even water. The solvents can be chosen in order to provide a system wherein at least a portion, and preferably all, of the catalyst, the co-catalyst, reactant (e.g., hydrogen), and the substrate dissolve to form a solution capable of affecting the desired transformation. The reactions may be conducted in such solvents at even mild temperatures and moderate pressures. Exemplary operable temperature ranges including those ranges from about 10° C. to about 15° C., from about 15° C. to about 20° C., from about 20° C. to about 25° C., from about 25° C. to about 30° C., from about 30° C. to about 35° C., from about 35° C. to about 40° C., from about 40° C. to about 45° C., from about 45° C. to about 50° C., from about 50° C. to about 55° C., from about 55° C. to about 60° C., from about 60° C. to about 65° C., from about 65° C. to about 70° C., from about 70° C. to about 75° C., from about 75° C. to about 80° C., from about 80° C. to about 85° C., from about 85° C. to about 90° C., from about 90° C. to about 95° C., from about 95° C. to about 100° C., from about 100° C. to about 120° C., from about 120° C. to about 140° C., from about 140° C. to about 160° C., from about 160° C. to about 180° C., from about 180° C. to about 200° C., or any combination of these ranges, for example, from about 20° C. to about 100° C., from about 25° C. to about 60° C., or from about 35° C. to about 50° C. Exemplary pressure ranges include those ranges from about 1 bar to about 2 bar, from about 2 bar to about 3 bar, from about 3 bar to about 4 bar, from about 4 bar to about 5 bar, from about 5 bar to about 10 bar, from about 10 bar to about 15 bar, from about 15 bar to about 20 bar, from about 20 bar to about 25 bar, from about 25 bar to about 30 bar, from about 30 bar to about 40 bar, from about 40 bar to about 50 bar, or any combination of these ranges, for example, from about 2 bar to about 50 bar, or from about 5 bar to about 25 bar, where "bar" refers to absolute pressure. In the case of hydrogen, these conditions provide sufficient dissolution of hydrogen in most solvents to provide a reaction mixture having convenient turnover rates.

An inorganic basic co-catalyst may be useful in imparting catalytic activity, especially with the bifunctional complexes. Exemplary inorganic base catalysts may include, but are not limited to, alkoxide bases, such as sodium methoxide, potassium tert-butoxide, aluminum isopropoxide or the like. Without intending to be bound by the correctness or incorrectness of any particular theory, it may be that the alkoxide activates the transition metal catalyst by displacing other anionic ligands.

VII. Examples

General Experimental Section—

Chemicals and solvents were purchased from VWR, Oakwood Chemicals, and Sigma-Aldrich, and used directly without further purification unless otherwise stated. All reactions dealing with air- or moisture-sensitive compounds were carried out in a dry reaction vessel under nitrogen. Anhydrous toluene was obtained by passing the solvent (HPLC grade) through an activated alumina column on a PureSolv MD 5 solvent drying system.

$^1$H and $^{13}$C NMR spectra were recorded on Varian 400 MHz or Varian 500 MHz NMR Spectrometers. Spectra were recorded in deuterated chloroform ($CDCl_3$). Tetramethylsilane (TMS, set to 0 ppm) was used as internal standard for chemical shifts. Solvent peaks were referenced as 7.26 ppm for $^1$H and 77.16 ppm for $^{13}$C NMR, respectively. Chemical shifts (δ) are reported in parts per million (ppm) from low to high frequency and referenced to the residual solvent resonance. Coupling constants (J) are reported in Hz. The multiplicity of $^1$H signals are indicated as: s=singlet, d=doublet, t=triplet, dd=double doublet, m=multiplet, br=broad.

High resolution ESI mass spectrometry was recorded using an Agilent 6230 TOF MS, and trifluoro acetic acid (TFA) was added to samples to promote ionization.

MALDI-TOF mass spectra were recorded on a Bruker microflex MALDI-TOF spectrometer.

TLC information was recorded on Silica gel 60 F254 glass plates. Purification of reaction products was carried out by flash chromatography using Silica Gel 60 (230-400 mesh).

UV/vis spectrum of PDAPP was obtained on a Perkin-Elmer Lambda 750 UV/vis spectrophotometer.

General Synthetic Schemes

Phosphine Based Macrocycle Synthesis:

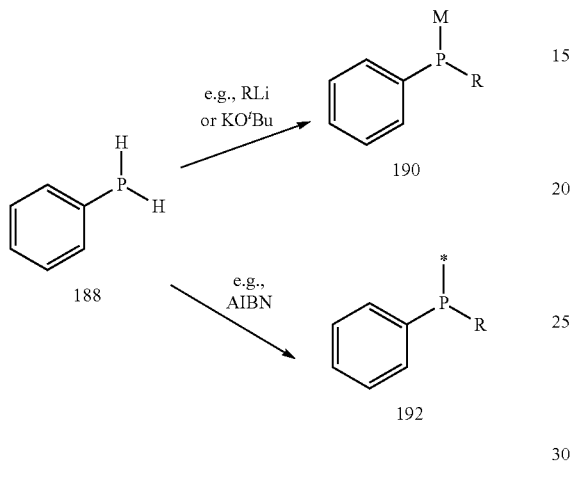

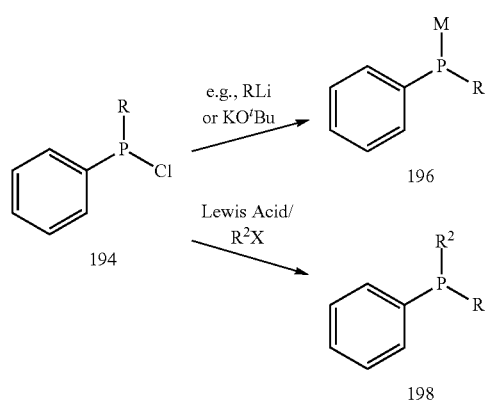

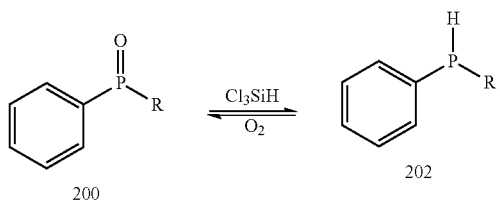

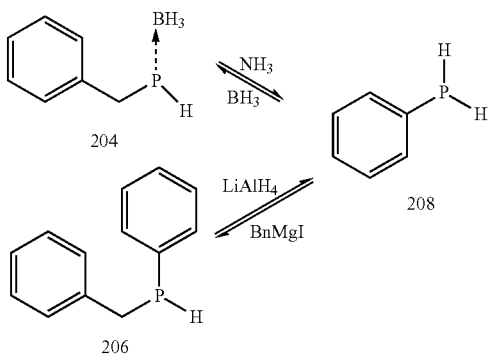

Phosphines are readily oxidized. The syntheses steps disclosed herein therefore utilize intermediates (i.e., phosphine or phosphine chloride) that reduce the potential for oxidation. Additionally, the phosphine oxides disclosed herein allow simplifying the reactions, purification and/or identification of products. Phosphine oxides, borohydride adducts and benzyl-phosphines are used as suitable substitutes that can control the product oxidation state and can also be readily converted into the desired final products (e.g., phosphine) (Schemes 22-23). These alternative intermediates are therefore implicit in all examples. These alternative synthons are then reacted to the corresponding phosphines as exemplified in Schemes 22-23. It is further possible to use phosphine and phosphine halogenides as suitable starting materials in the syntheses outlined below:

Reductions of Phosphines:

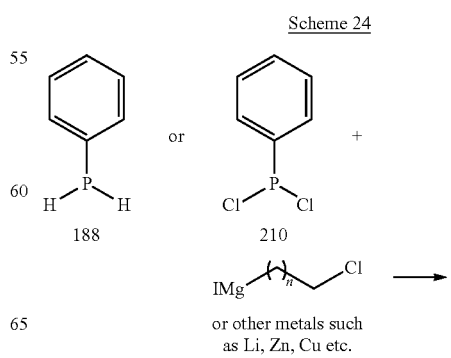

As described in Schemes 20 and 21, syntheses of phosphine-based linkages, such as P—C, P—N, P—S and other linkages disclosed herein can be accomplished, for instance, via radical initiation at a phosphine center, metalation at a phosphine (e.g., Scheme 20) or phosphine chloride (e.g., Scheme 21), metal exchanges of metalated phosphines, Lewis acid activated addition to halogen-alkane, Michael additions to phosphine alkenes or the like. In this work, these different methodologies can be used depending, for example, on the convenience of the chemical steps, overall yields and the availability of intermediates. Reactions outlined herein are mere examples and are not meant to be limiting as common reactions are often interchangeable to those that are experts in phosphorus chemistry.

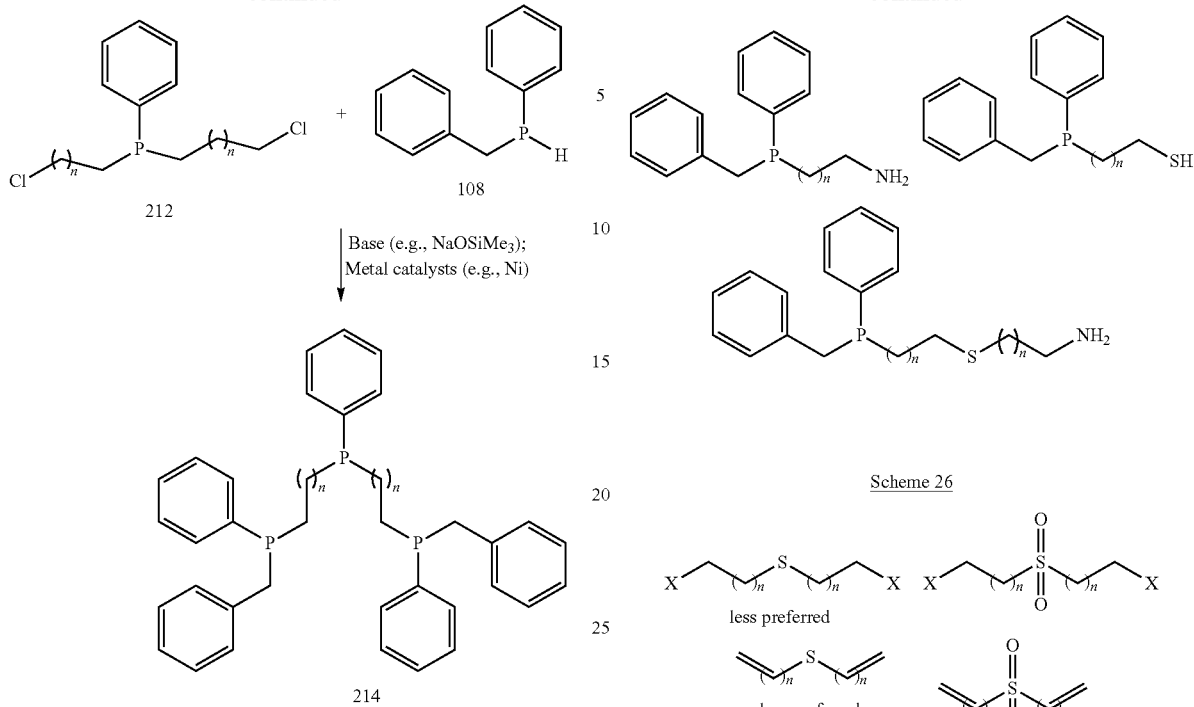

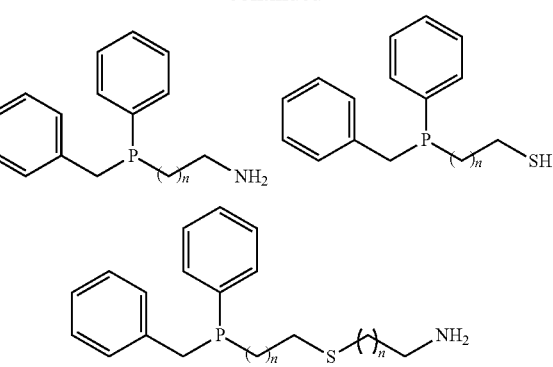

Scheme 24 illustrates a synthetic method that begins either with a phosphine or phosphine chloride. Metalation of the phosphine is then followed by an addition of a haloalkane or haloalakane derivative. Alternatively, a Grignard reagent of the bridging linker can be added to either the phosphine or phosphine halogenide. Such reactions can be achieved by classic Grignard conditions, lithiation with a RLi and/or transmetallation.

If the starting material for the alkane halogenide is either a non-symmetrical bishalogenide or a suitably protected alcohol based precursor, the phosphine can then be reacted under harsher conditions with a second equivalent of a phosphine halogenide to form the tris-phosphine intermediate.

Reaction conditions can be chosen to allow symmetrical double additions or the use of different phosphine reagents in the consequent steps. These intermediates can be then converted to a reactive phosphine for further macrocycle syntheses by removing the benzyl groups upon reduction with LAH.

Scheme 25

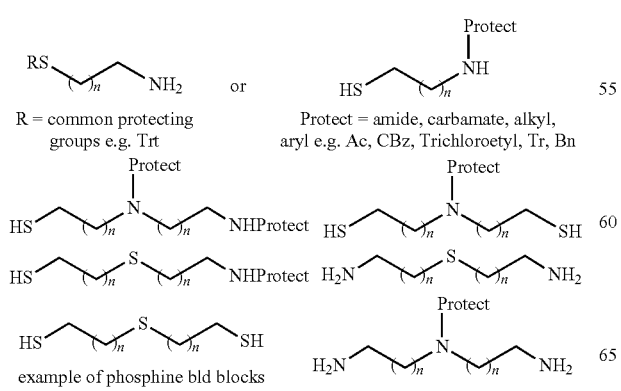

Scheme 26

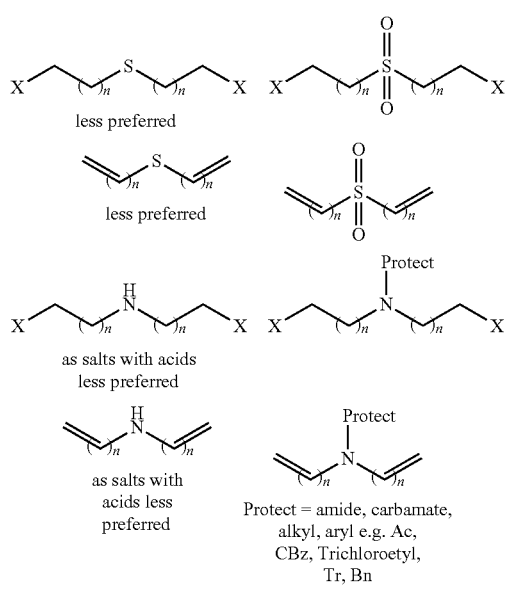

Scheme 27

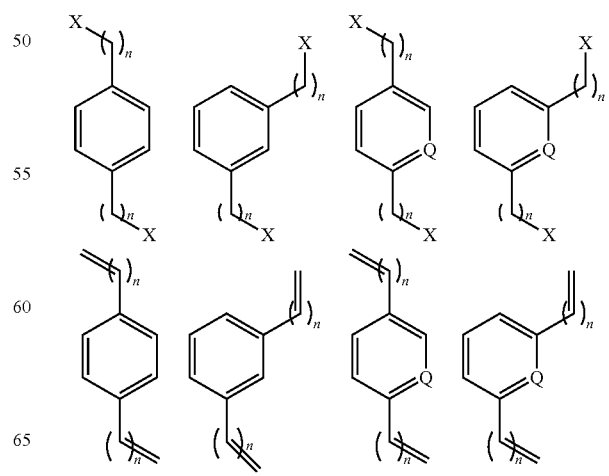

-continued

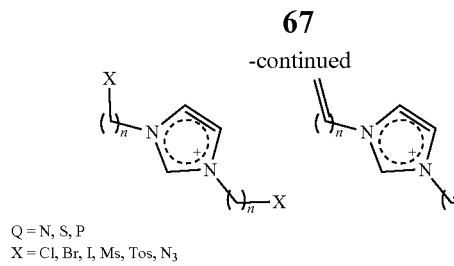

Q = N, S, P
X = Cl, Br, I, Ms, Tos, N₃

This reaction is not limited to alkanes, and can be extended to aryl dihalogenides, heteroatom containing linkers and carbene precurors. Some of which are exemplified in Schemes 25-27. Scheme 25 depicts exemplary illustrative representations of linking moieties attached through Michael type additions, while Scheme 26 depicts exemplary illustrative representations of linking moieties for a) halogen and metal organic reaction with phosphines and b) attached via Michael type additions to vinyl and allyl groups. Scheme 27 depicts exemplary illustrative representations of aryl and heterocycle moieties used as linkers.

It is important to note that one or more heteroatom linkages, such as between two adjacent phosphines, phosphine-nitrogen, phosphine-sulfur, or phosphine-carbon, can also contain chiral groups that impart overall chirality to the final product.

Further modification of the linkages include those necessary to modify the physicochemical characteristics of the product. For example, we may include ethyleneglycol derived links, modifications of a bridging chain, aryl and the like at any position to improve the solubility of the macrocyclic products. Such modifications may further include reactive side chains, or reactive sites to allow immobilization of the macrocycle onto a solid support, or bioconjugation onto a surface, protein or enzyme.

Scheme 28 illustrates the syntheses of triphosphine precursors using Michael additions (in the absence of radical initiator) or radical promoted addition (shown is AIBN). As previously described, these radical reactions are equally applicable to halogen alkane phosphines and can be achieved by a wide range of radical initiators.

Scheme 28

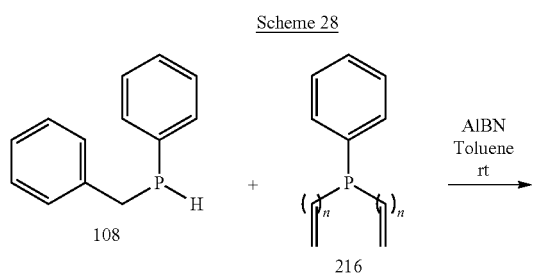

-continued

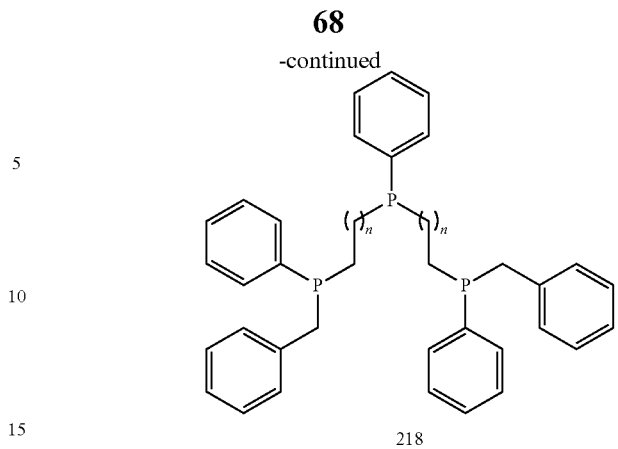

218

Michael additions to vinyl- or allyl phosphines are further suitable for reaction with one or more nucleophiles, such as amines, thiols and other nucleophiles to obtain substituted phosphines, such as amino, thiol alkane, alkene, and aryl linked phosphines disclosed herein.

Scheme 29

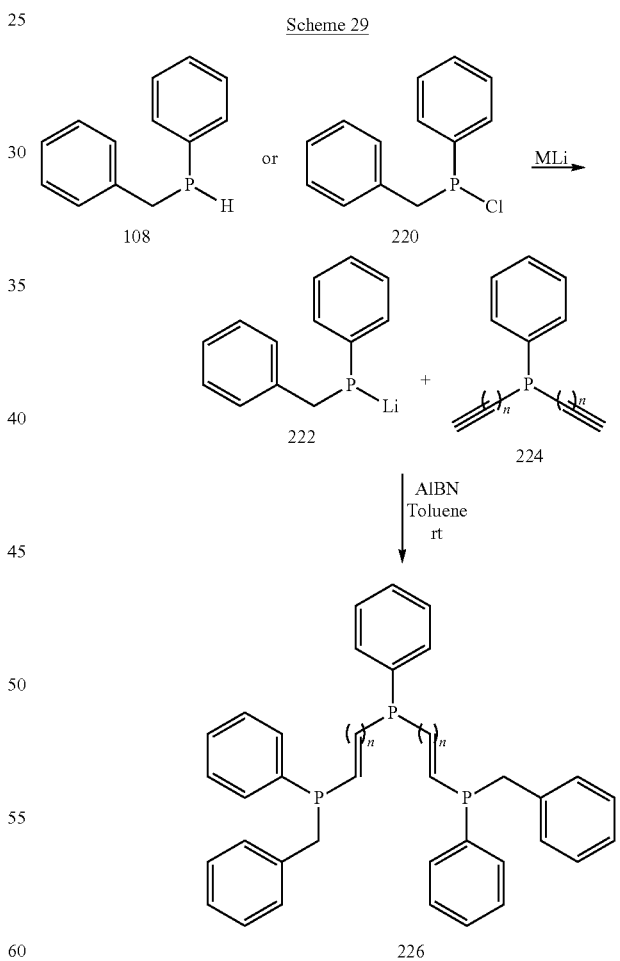

Similar reactions with alkynes, and arylalkynes lead to the formation of intermediates, such as alkene linked phosphine intermediates that restrict conformational isotopomer formation of the final metallorganic species as depicted in Scheme 29. Additionally, analogous reactions are also applicable to aromatic systems as a bridging link between phosphine, nitrogen, sulfur and oxygen moieties contained within the macrocycle.

Examples of suitable precursors for these reactions also include imidazoles and triazoles as shown in Scheme 27.

These reagents include a wide range of carbene forming entities such as imidazole or imidazolide salts (such as mesylates) to form novel phosphine/carbene based tetradentate ligands disclosed herein.

Reactions to form precursors and cyclized carbene-phosphine macrocycles are performed under high dilution or by metal assisted templating (such as Fe salt addition) to facilitate the desired reaction and prevent undesired by-product formation.

Cyclization Reactions:

The heteroatom precursor moieties disclosed herein can be subjected to one or more cycliation reactions to afford the macrocyclic polydentate ligands disclosed herein. The one or more cyclization reactions may be performed, for instance, via Michael type additions to double bonds, Michael type additions to nitrogen or sulfur, metallation and reaction with halogen alkanes and radical induced reactions of phosphines with halogen alkanes, double or triple bonds and heteroatoms. Exemplary cyclization reaction is provided below in Scheme 30.

Scheme 30 illustrates reaction of a phosphine alkene with an amine, followed by reduction of the benzyl group to provide an amino derivative. The resultant amino derivative is reacted with an excess of vinylsulfone, and the resulting product is subjected to a final ring closure to afford a HNSPP based macrocycle. This reaction is performed under high dilution of starting materials with slow addition of the sulfone, to avoid polymer formation. Final reduction of the intermediate with LAH affords the thioalkane linked-bis-phosphine ligand.

Scheme 31

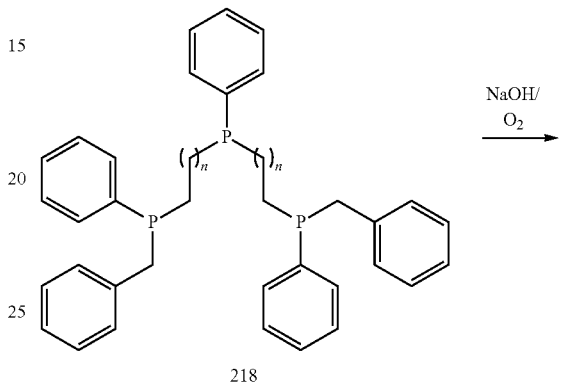

Scheme 30

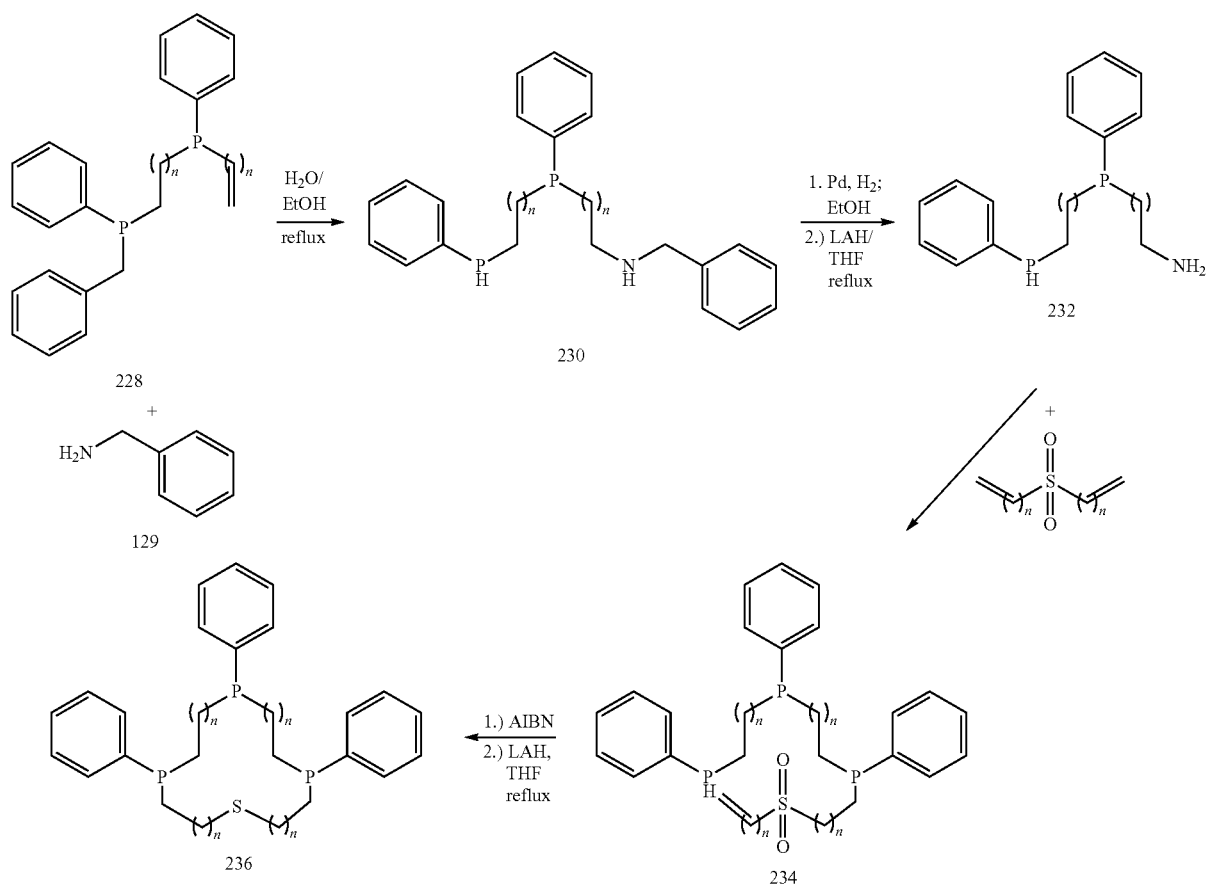

-continued

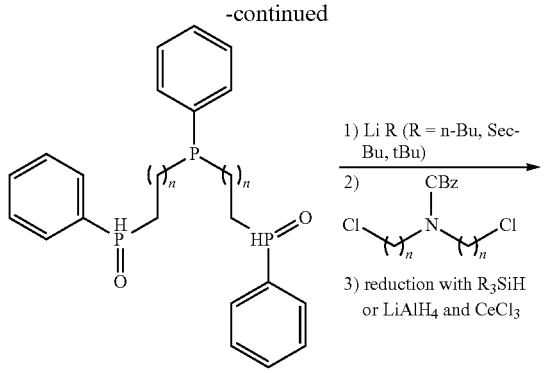

238

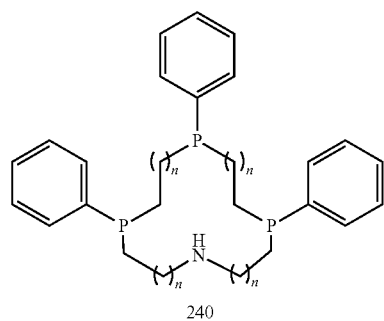

240

Scheme 31 depicts a reaction of a tris-phosphine precursor obtained from the removal of the benzyl groups from the phosphorus containing precursor by heating in sodium hydroxide solution, affording a bis-phosphine oxide intermediate. The phosphine oxide is then reacted with an allyl lithium reagent or used directly with a metal catalyst such as Pd or Ni, followed by, for example, by addition of a suitably protected nitrogen mustard.

High dilution of the reagents and slow addition of the nitrogen mustard favors ring formation over polymeric side-products. Deprotection and final reduction of the phosphine oxide with LAH affords the nitrogen tris-phosphine based macrocyclic ligand.

Synthesis of Phosphorus Macrocycles

An alternative approach to using cyclization reactions in dilute solutions is to use metal templating. As understood, metal templating permits reactions to be carried out under higher concentrations, favors ring closures and reduces polymer formation. Metals are preferably chosen such that their removal before final assembly of the macrocylic ligand based catalyst is accomplished.

Scheme 32

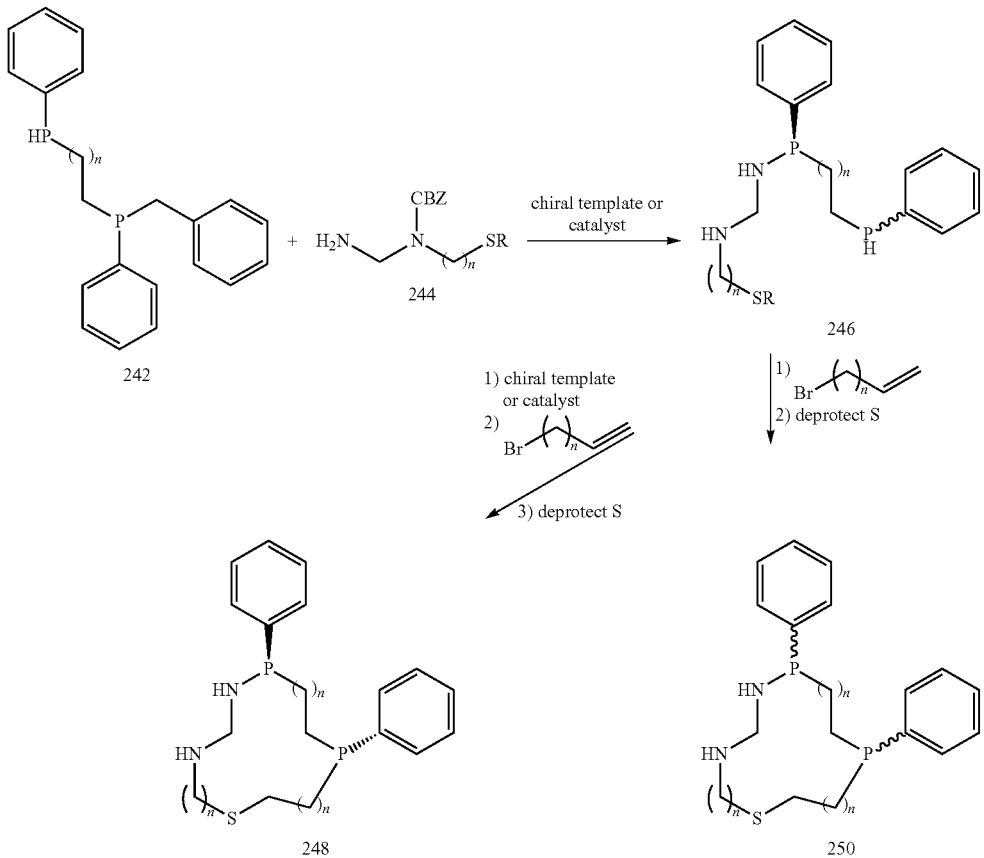

Scheme 32 illustrates an exemplary cyclization reaction accomplished using chiral metal complexes or, alternatively, in the presence of chiral co-ligands. For example, as depicted in scheme 32, chiral metal ligand templates lead to stereoselective reactions at the phosphorus atom to afford chiral macrocyclic polydentate ligands. Alternatively, chiral bridging moieties between P, N, and S atoms within the macrocyclic links can also be derived, for example, from a naturally occurring precursor, such as amino acid alcohols.

from chiral phosphine:

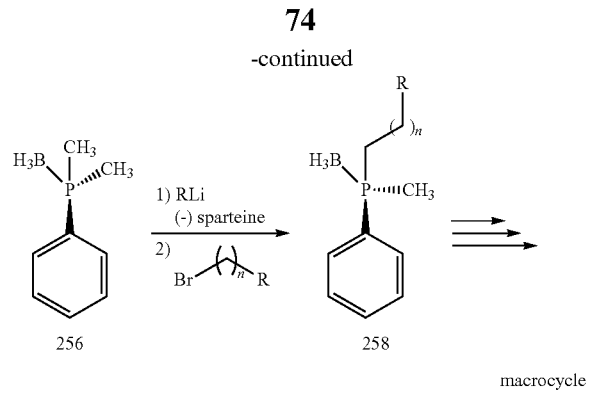

Scheme 33

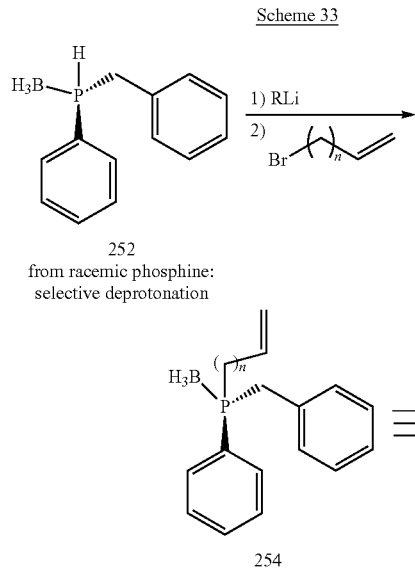

As depicted in Scheme 33, chiral phosphine precursors can also be employed as starting materials and such phosphines are readily available from the resolution of racemic precursors.

Other methods incorporate stereoselective deprotonation/metalation of phosphine boranes in the presence of, for example, sparteine. These can then be stereoselectively added to form intermediates or upon closure of the macrocycle. These reactions are easily incorporated in the syntheses of macrocycles and/or precursors to yield enantiomerically pure stereoisomers suited as ligands for stereoselective catalysis.

Synthesis of Macrocyclic Ligand L1:

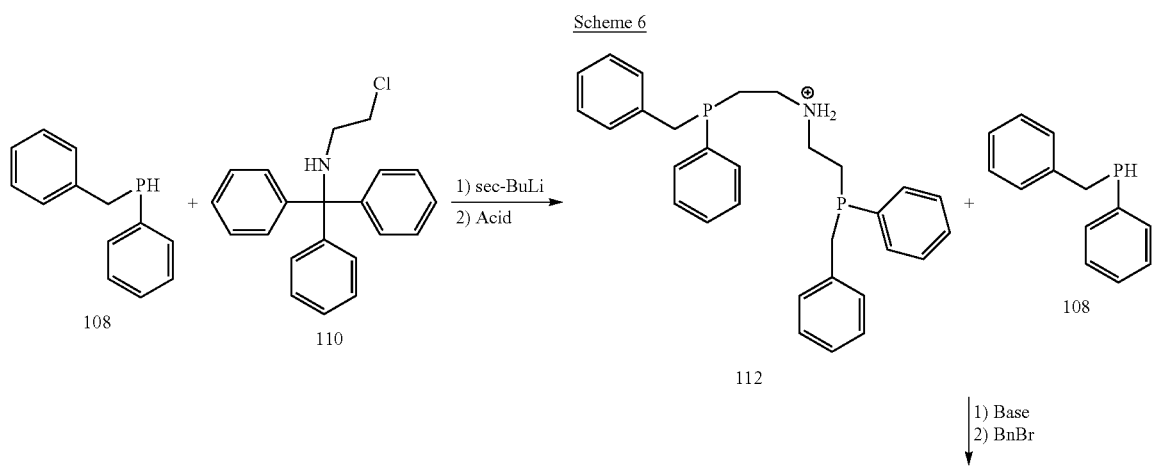

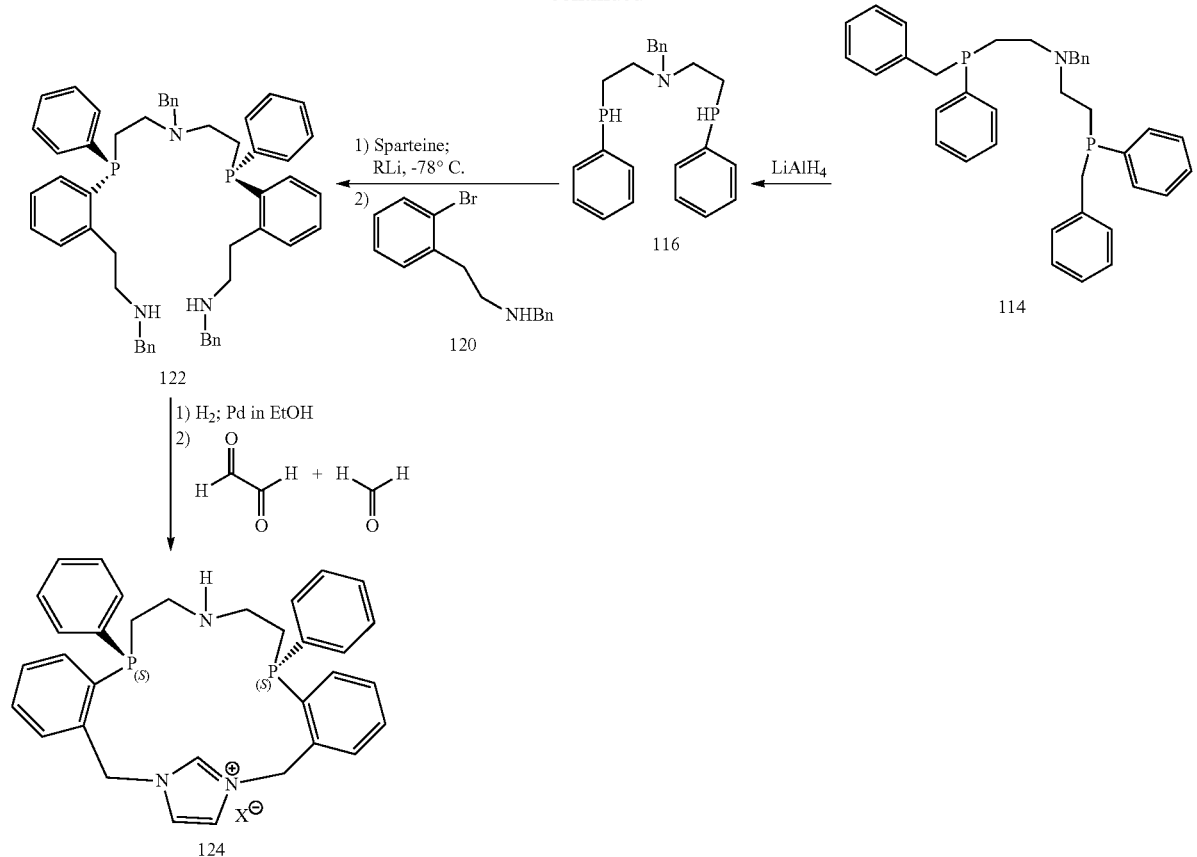

Scheme 6 depicts a synthetic route for making the macrocyclic ligand L1. As depicted in scheme 6, a phenylbenzylphosphine 108 is condensed using the addition of a base with tritylamine 110. The resulting amine is then converted to the primary amine, in situ, under acidic hydrolysis conditions. Triethylamine is added to the solution and the amine 112 reacted with a second equivalent of the phenylbenzylphosphine 108. This stepwise approach prevents not only side-product formation, due to steric hinderance afforded by the trityl group, but also allows the first phosphine and the consequent phosphine addition to use different phosphine as starting materials. After protection of the secondary amine with functional groups such as, Bn-, Trt, or the like, benzylphosphine derivative 114 is reduced with Lithium aluminum hydride in THF. The resulting phosphine 116 is then stereoselectively lithiated in the presence of sparteine with butyl lithium in THF at low temperature. Addition of a protected bromoarylethylamine 120 leads to the formation of one stereoisomer 122 of the ligand scaffold. Hydrogenation removes the protecting groups and the adjacent primary amines are reacted with a bis-ketone and formaldehyde using acid catalysis, or templated by Lewis acids to form the imidazole and close the macrocycle LI 124.

Synthesis of Ligand 138:

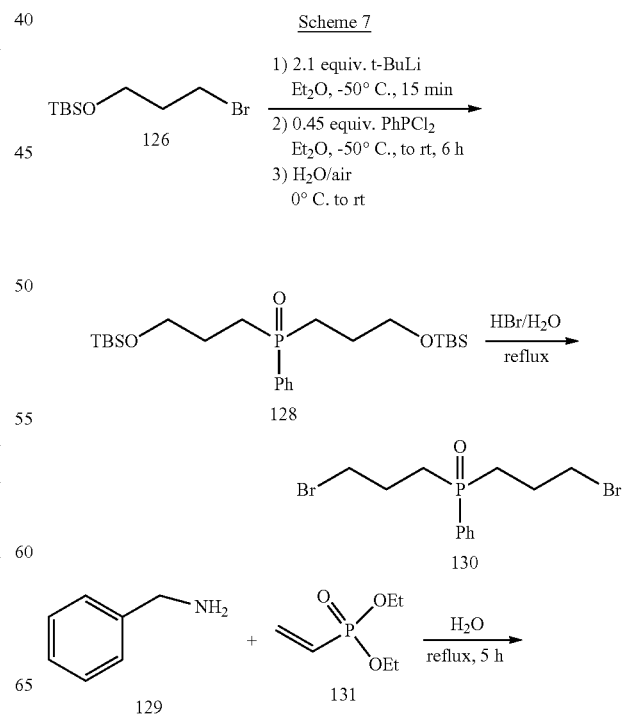

Synthesis of Ligand 146:

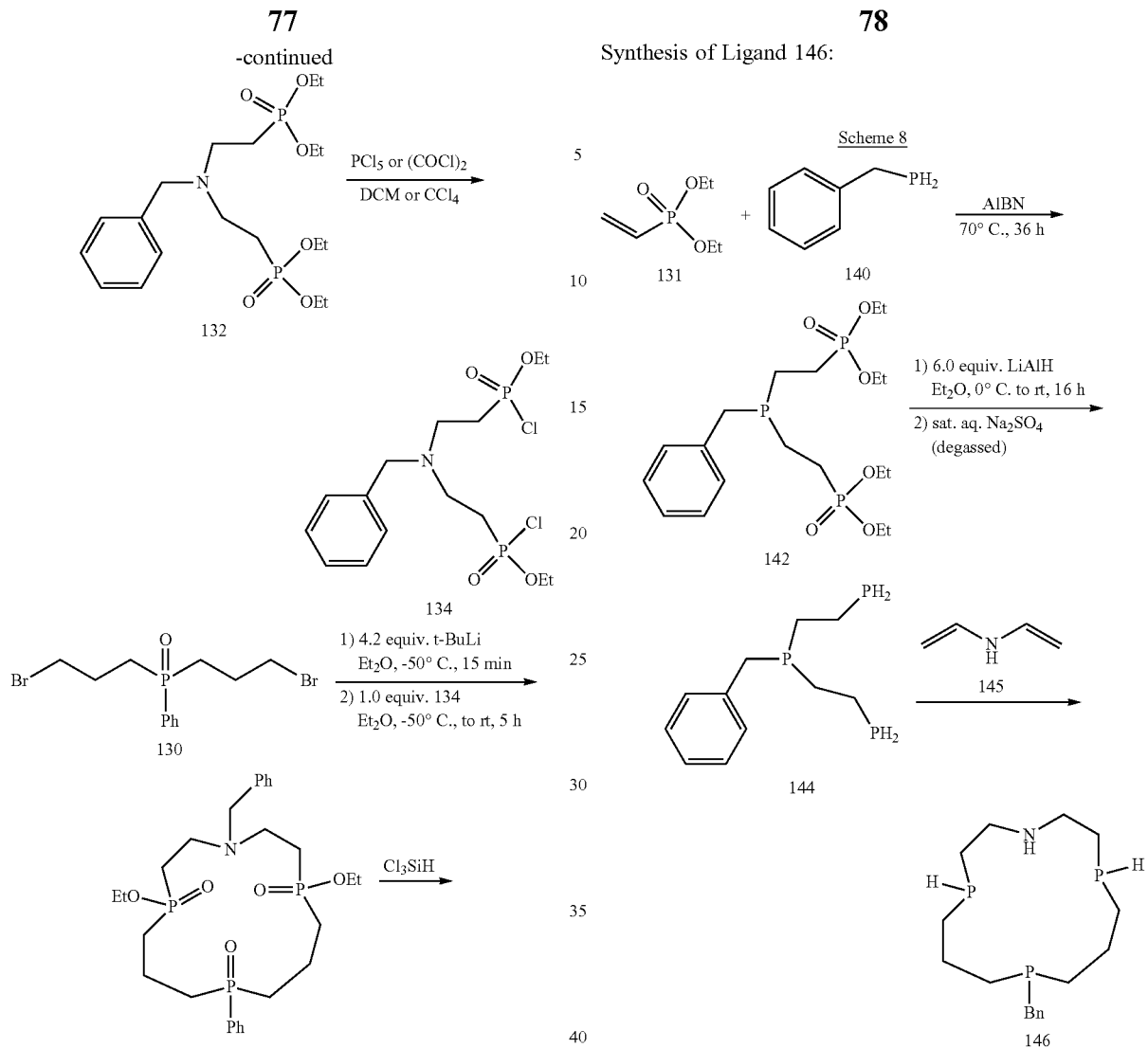

As depicted in Scheme 7, a bis bromoalkylphosphine 130 has been obtained in high reaction yields. An aminobisphosphonate 132 has been converted to a corresponding bis chloride derivative 134 in high yields following standard reaction conditions described in the literature. Lithiation of the bis bromide 130 with tert. Butyllithium followed by slow addition of the benzylamino-(chloro bisphosphonate) 134 closes the macrocycle 136 under high dilution conditions, which can then be reduced to the phosphine 138 with trichlorosilane.

As depicted in Scheme 8, a vinylphosphonate ester 131 is reacted under radical induced conditions (AIBN) with the benzylphosphine 140 to afford the P,P,P fragment 142 in high yields, which upon reduction with lithium aluminum hydride produces the corresponding bisphosphine derivative 144. Commercially available bisvinylamine 144 is then added in Michael type reactions in high dilution or templated to yield the macrocycle P,P,P,N 146. In another example, commercially available bisvinylsulfur synthon may also be added to the bisphosphine derivative 144 in a Michael-type addition to yield a corresponding P, P, P, S macrocycle (not shown).

Synthesis of Ligand 162:

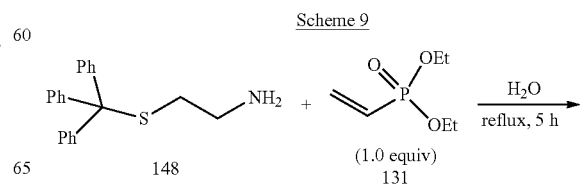

-continued
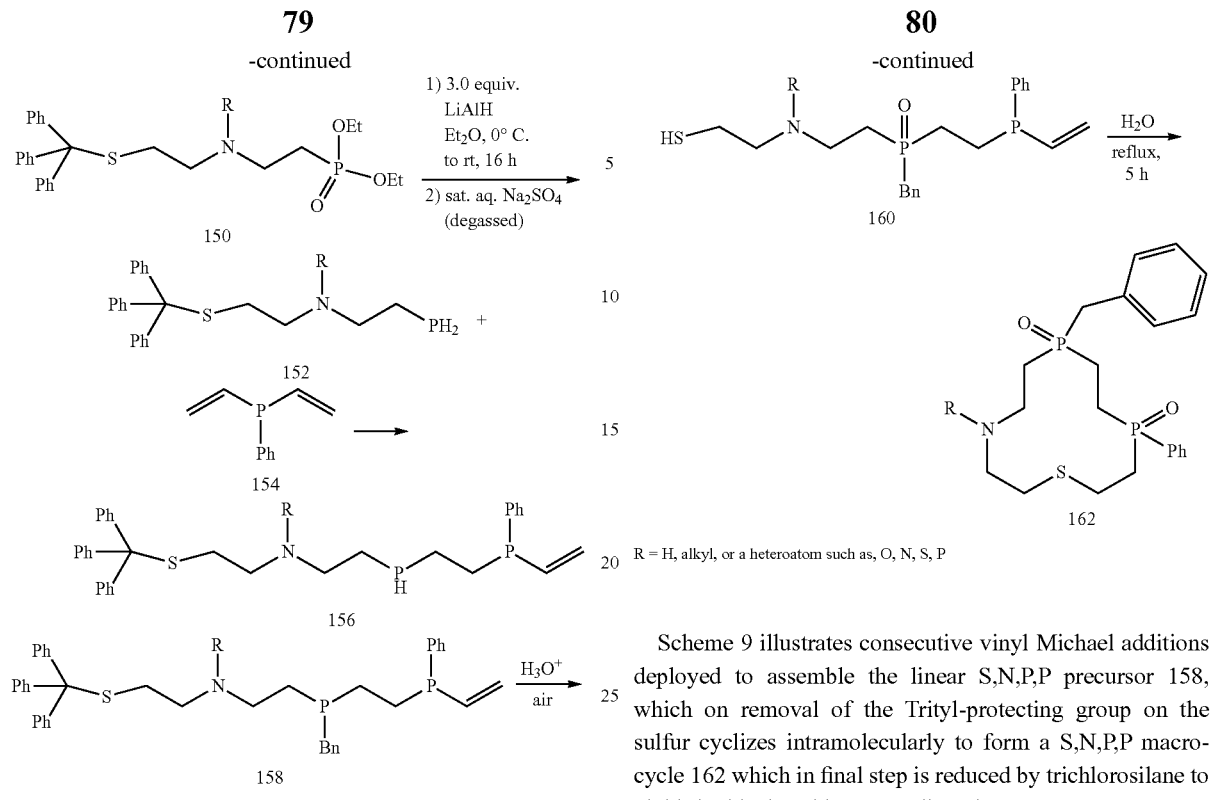
Scheme 9 illustrates consecutive vinyl Michael additions deployed to assemble the linear S,N,P,P precursor 158, which on removal of the Trityl-protecting group on the sulfur cyclizes intramolecularly to form a S,N,P,P macrocycle 162 which in final step is reduced by trichlorosilane to yield the bisphosphine, N, S-ligand.
Scheme 34
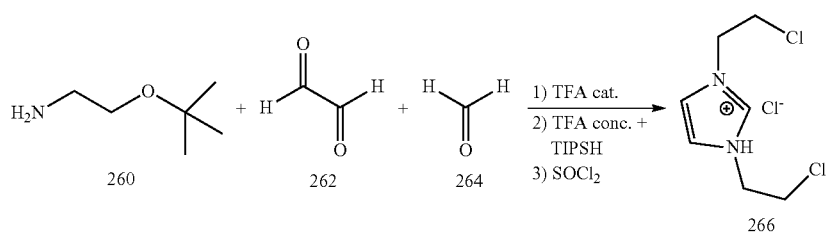
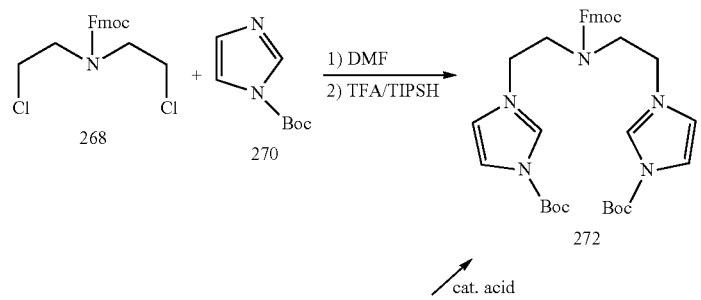
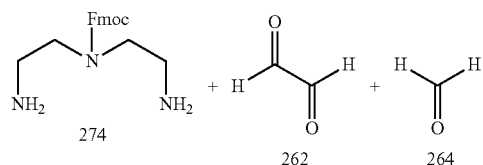

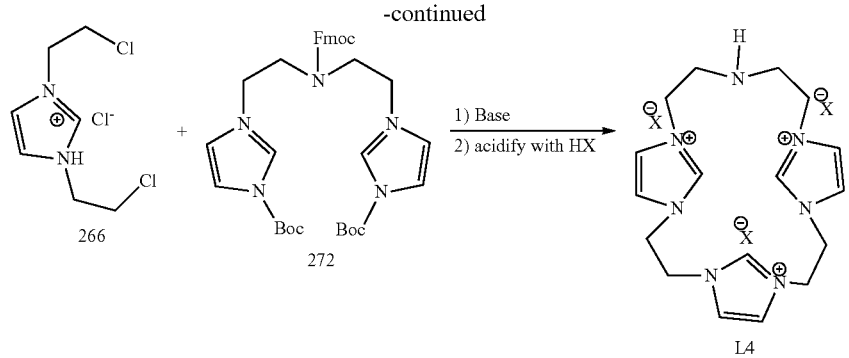

A suitably protected primary amino alcohol is reacted with a vicinal bis-ketone and formaldehyde to yield a carbene precursor. Upon deprotection, the alcohol is converted into a leaving group (e.g., Cl as shown). The second part of the macrocycle is constructed by reaction of a protected nitrogen mustard with an imidazole or triazole. Alternatively, the aminoalkane linked imidazole can be obtained by the condensation of the bis-ketone and formaldehyde with a protected tris-amine. Final cyclization is achieved under high dilution using basic conditions or templated with a metal (e.g. Fe). Metal templates are preferable in order to stabilize the carbene ligands.

In-Situ Synthesis of Metal Coordination Complex:

Scheme 16

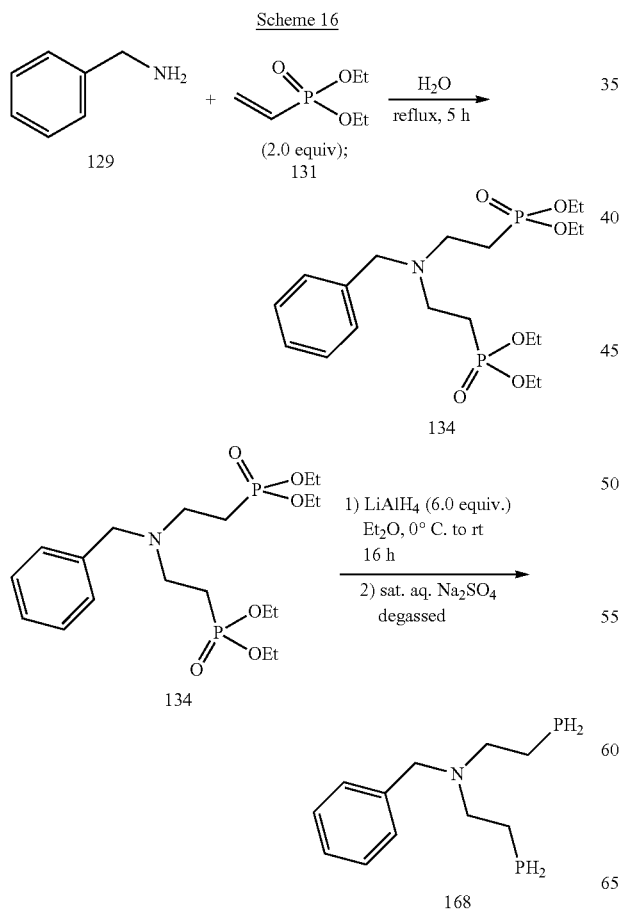

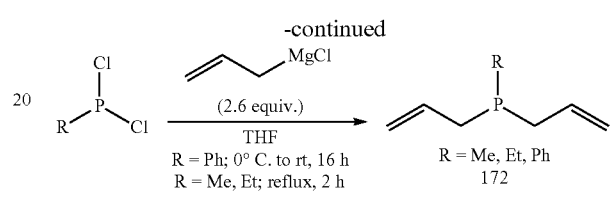

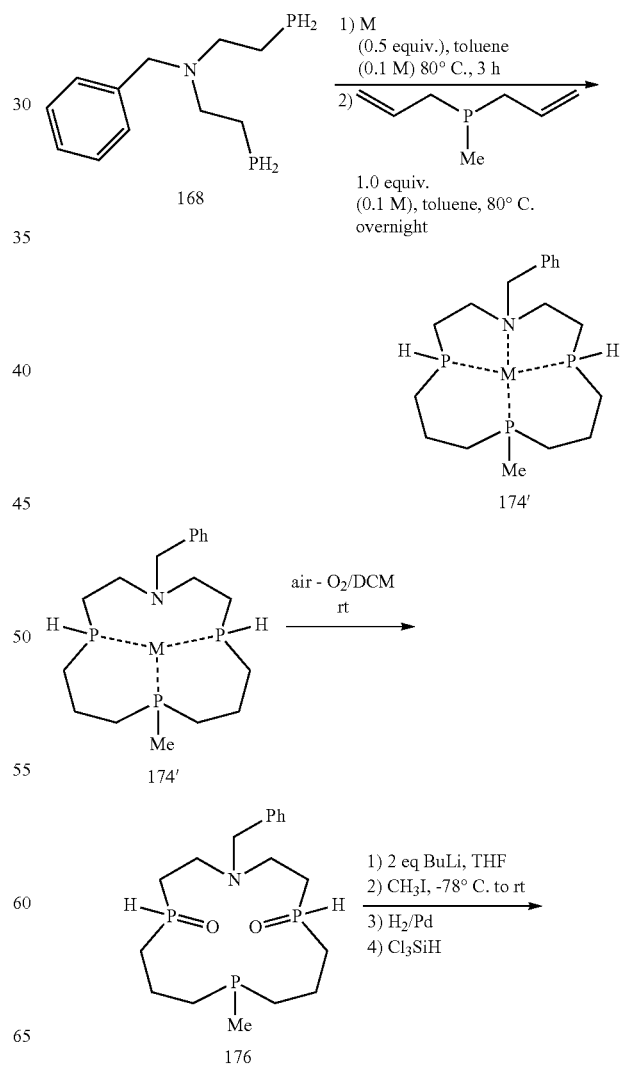

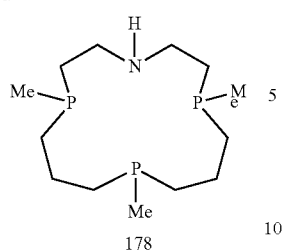

178

An example of the total synthesis of a PPNP macrocyle is represented in Scheme 16. Starting from commercially available vinylphosphonic ester 131 and benzylamine 129, a Michael addition leads cleanly and in high yields (97%) to the PNP bis phosphonate precursor 134 of the macrocycle. Reduction with Lithiumaluminum hydride affords the phosphine 168 in moderate yields (55%). Bis-vinylphosphines 172 (or phosphine oxide respectively) are obtained in moderate yields from an addition of the vinyl-Grignard reagent to the dichlorophosphine. The cyclization proceeds under e.g. Ruthenium template assisted conditions at elevated temperature to close the macrocycle 174' in low to moderate yields. Air oxidation converts 174' to the phosphine oxide 176 in excellent yields. Alkylation of the phosphines (shown is methyladdition), is followed by deprotection of the Nitrogen protecting group (shown is hydrogenation of N-benzyl) is followed by trichlorosilane reduction to yield the final macrocycle assembly 178.

Computational Analysis of Influence of Ligand Nature on a Trans- or Cis-Isomerism of a Ru Catalyst Complex.

In a prophetic example, P-chirogenic ligand precursor L1 can react with a suitable Ru-precursor to afford trans- and/or cis-isomer of the corresponding Ru-(pre)catalyst complex as shown below in Scheme 15:

Scheme 15

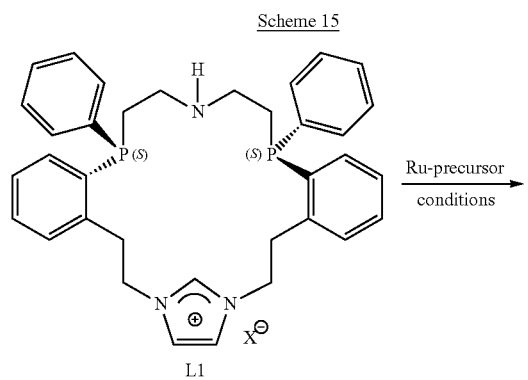

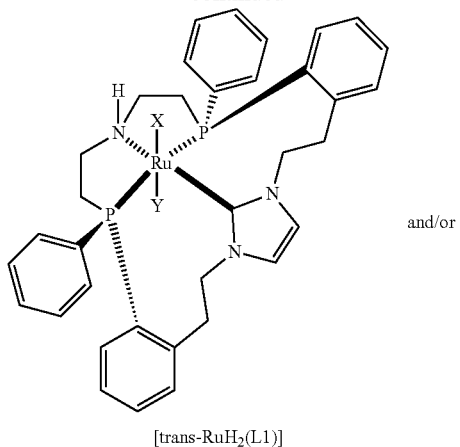

[trans-RuH₂(L1)]

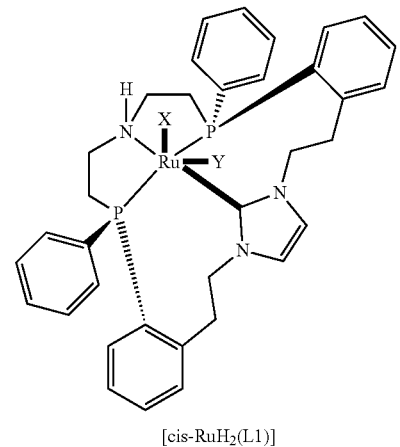

[cis-RuH₂(L1)]

FIG. 1 shows corresponding geometries optimized under M06L/SDD(Ru)/6-31G*(all others) level of theory and their relative energies for the case when X=Y=H.

An initial estimation for the geometry optimization for the trans-isomer was constructed from an available X-Ray structure of the similar Ru-complex composed of a tridentate PNP ligand containing an N—H functionality and a carbene auxiliary (see WO2015163440A1; Ogata, O., Nakayama, Y., Nara, H., Fujiwhara, M. & Kayaki, Y. Atmospheric Hydrogenation of Esters Catalyzed by PNP-Ruthenium Complexes with an N-Heterocyclic Carbene Ligand. Org. Lett. 18, 3894-3897, (2016)). As further depicted in FIG. 1, an initial estimation for the cis-isomer was constructed from the optimized geometry of the trans-isomer, by placing two hydride atoms in a cis-position following geometry optimization. Preliminary computational analysis suggests that in the reaction between L1, composed of two 5-membered and two 8-membered ruthenacycles, and a suitable Ru precursor, [trans-RuXY(L1)] should be the exclusive product in this reaction.

Scheme 17

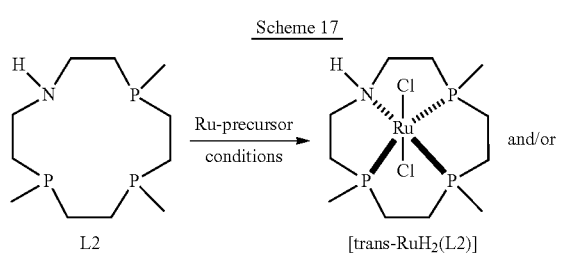

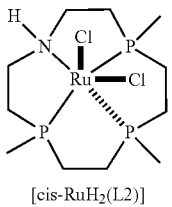

Scheme 18

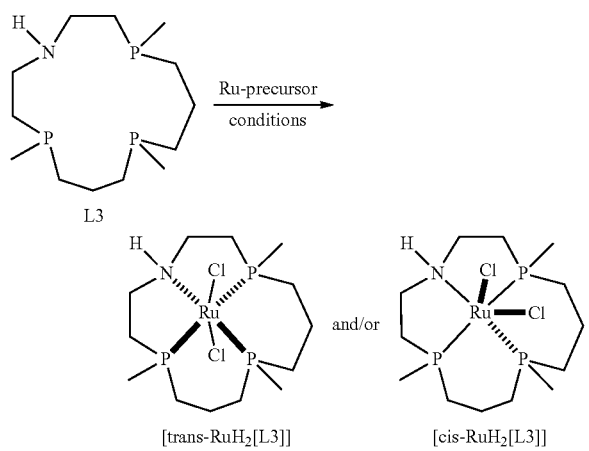

Similarly, NPPP ligands L2 and L3 are also expected to react with a suitable Ru-precursor to afford trans- and/or cis-isomer of the corresponding Ru-(pre)catalyst complex as shown in Schemes 17 and 18.

The same (pre)catalysts complexes could be obtained by using different procedure without direct isolation of L2 and L3 as shown below in Scheme 19:

Scheme 19

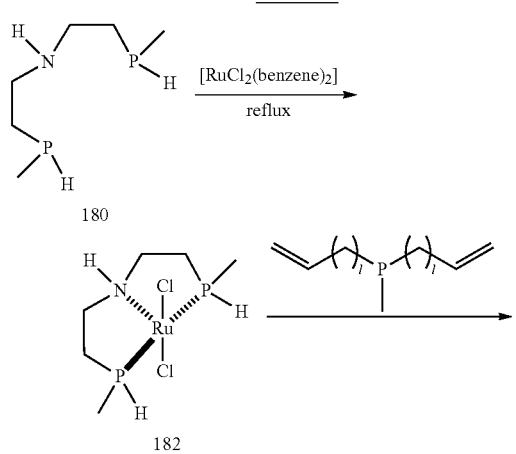

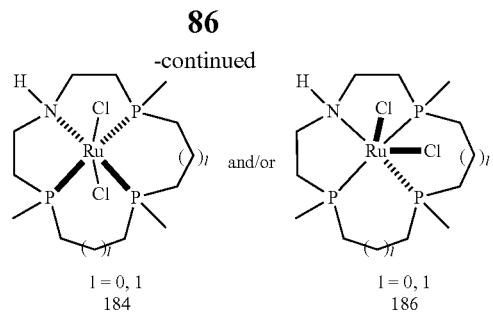

Figure 2:
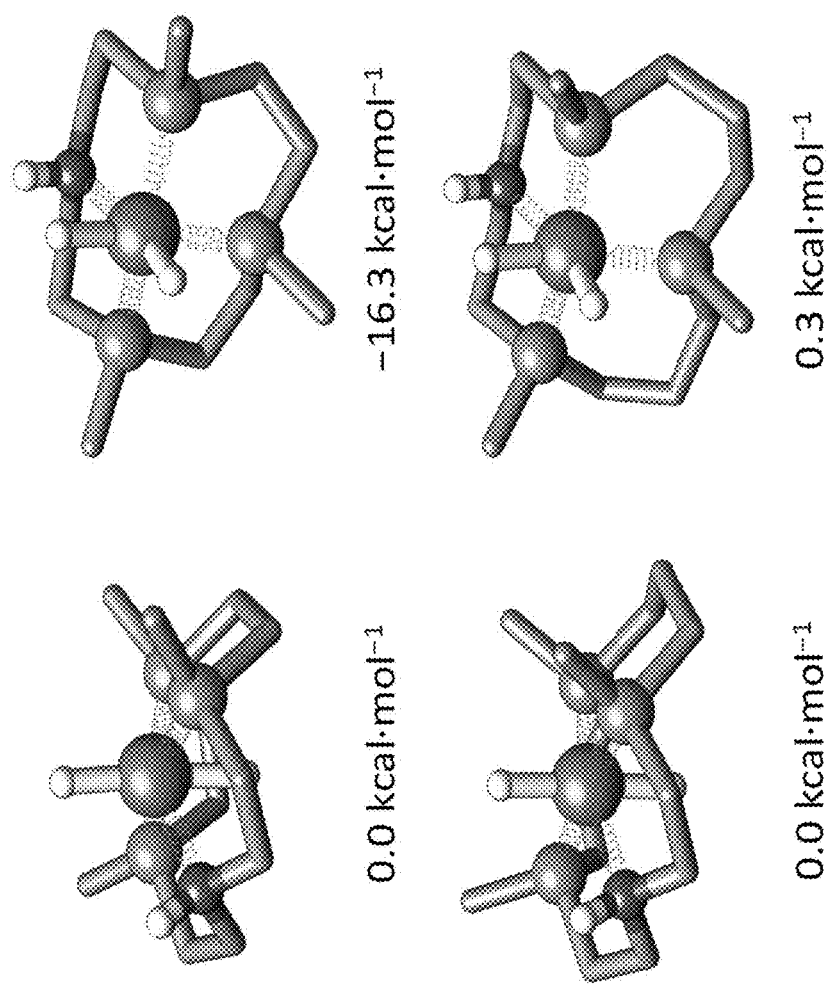
FIG. 2 depicts corresponding geometries of a representative ligand disclosed herein.

Preliminary conformational analysis for [RuH$_2$(L2)] and [RuH$_2$(L3)] complexes reveals the most stable isomers corresponding to trans- and cis-arrangements as shown in FIG. 2. For [RuH$_2$(L$_2$)] composed of four 5-membered ruthenacycles, the most stable isomer has a cis-arrangement. In contrast, for [RuH$_2$(L$_3$)] composed of two 5-membered and two 6-membered ruthenacycles, both trans- and cis-isomers are isoenergetic. The results demonstrate that tuning of the ligand nature (i.e., nature of heteroatom used, chain length between heteroatoms) could favor formation of either trans- or cis-isomers or both of the corresponding [RuXY(ligand)] (pre)catalyst complex as explicitly shown in Schemes 17 and 18.

Scheme 17

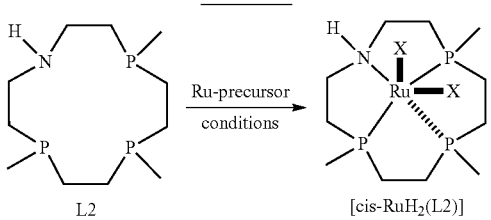

Scheme 18

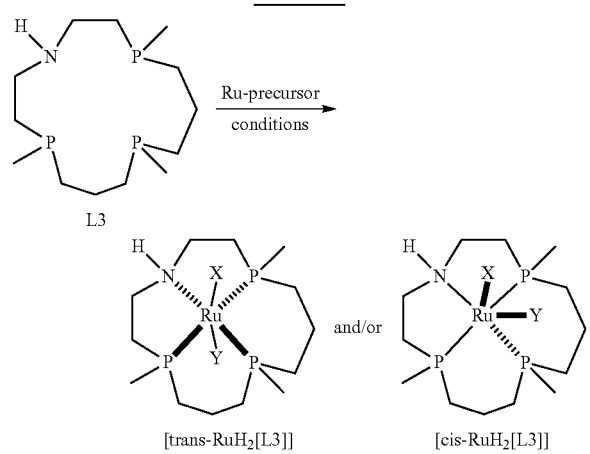

Catalytic Hydrogenation of Methyl Acetate into Ethanol:

Two highly efficient Ru (pre) catalysts bearing PNP ligand were previously developed for the hydrogenation of simple and chiral esters (see U.S. Pat. No. 9,000,212B2; US20140163257A1; WO2011048727A1; Kuriyama, W. et al. Catalytic hydrogenation of esters. development of an efficient catalyst and processes for synthesising (R)-1,2-propanediol and 2-(1-menthoxy)ethanol. Org. Process Res. Dev. 16, 166-171, (2012); Ogata, O., Nakayama, Y., Nara, H., Fujiwhara, M. & Kayaki, Y. Atmospheric Hydrogenation of Esters Catalyzed by PNP-Ruthenium Complexes with an N-Heterocyclic Carbene Ligand. Org. Lett. 18, 3894-3897, (2016); WO2015163440A1). In particular, the Ru-MACHO catalyst catalyzes the hydrogenation of chiral methyl (R)-lactate into (R)-1,2-propanediol with almost no loss in optical purity as shown below in Scheme 35.

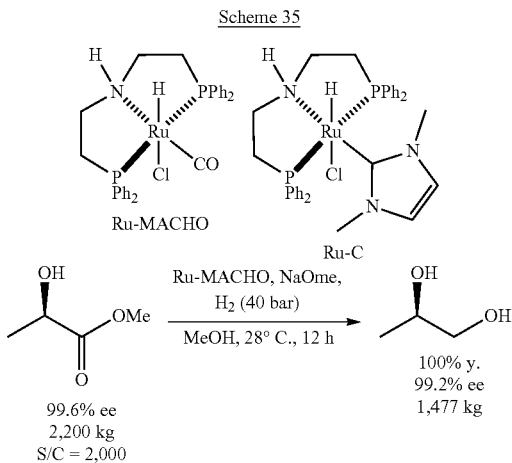

Figure 3:
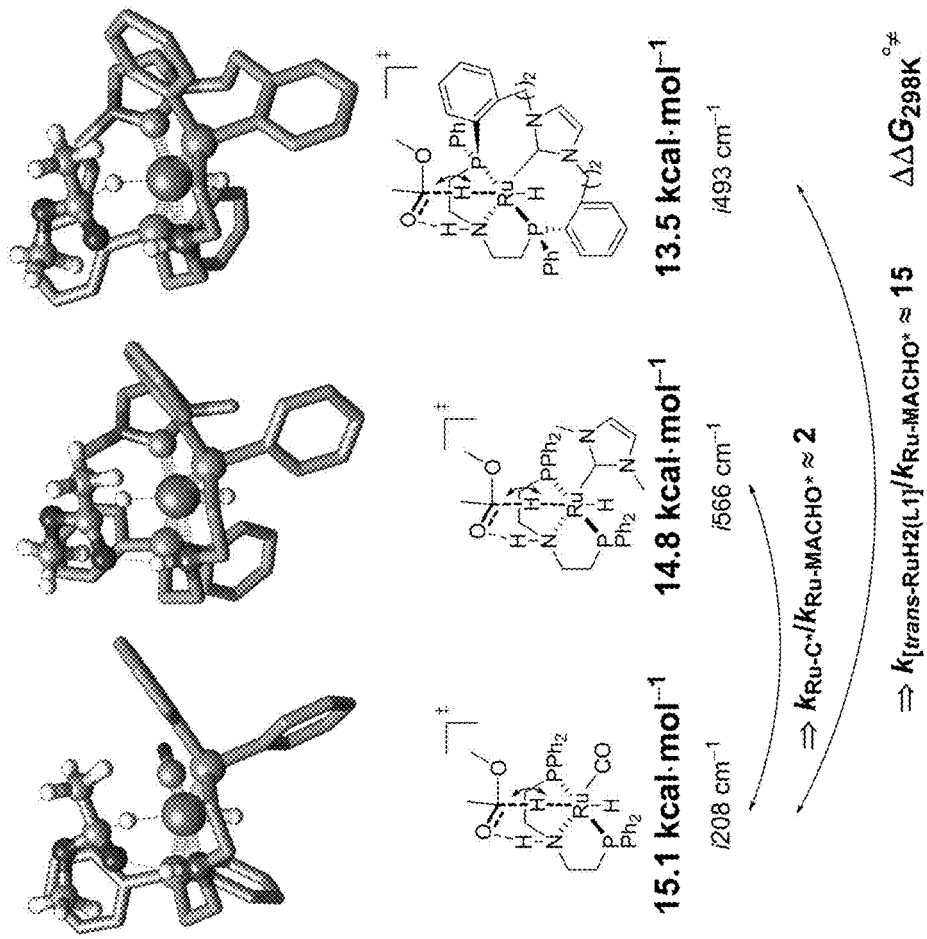
FIG. 3 depicts computed relative rate of hydride transfer from trans-$RuH_2$ complexes disclosed herein to methyl acetate.

FIG. 3 shows activation barriers and geometries of the transition states corresponding to the rate-determining hydride transfer from active intermediates of the catalytic cycle in these reactions with the catalysts:

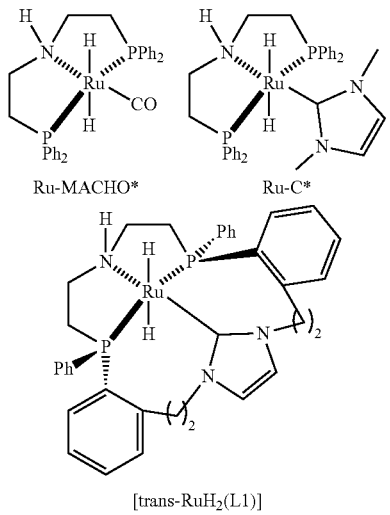

to methyl acetate ester optimized under M06L/SDD(Ru)/6-31G*(all others) level of theory.

The computational analysis suggests almost isoenergetic activation barriers for both Ru-MACHO* and Ru—C* catalysts and a slightly lower activation barrier for the [trans-RuH$_2$(L1)] catalyst disclosed herein, confirming that all three catalysts are versatile catalysts for ester hydrogenation. Providing that [trans-RuH$_2$(L1)] could be more stable catalyst than both Ru-MACHO* and Ru—C*, higher turnover numbers with this particular catalyst may actually be achieved.

Catalytic Hydrogenation of $CO_2$ into Methanol:

Recently, $CO_2$ including from air into methanol were converted into methanol using Takasago's Ru-Macho (pre) catalyst as shown below in Scheme 36 (Kothandaraman, J.; Goeppert, A.; Czaun, M.; Olah, G. A.; Prakash, G. K. S. J. Am. Chem. Soc. 2016, 138, 778).

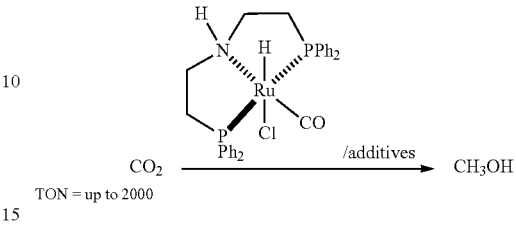

This reaction is remarkably efficient, providing turnover numbers (TONs) up to 2000. It is likely that the first step of this multi-step catalytic reaction is the outer-sphere hydride transfer from a trans-Ru—H$_2$ complex to $CO_2$ (Dub, P. A.; Scott, B. L.; Gordon, J. C. J. Am. Chem. Soc. 2017, 139, 1245).

Figure 4:
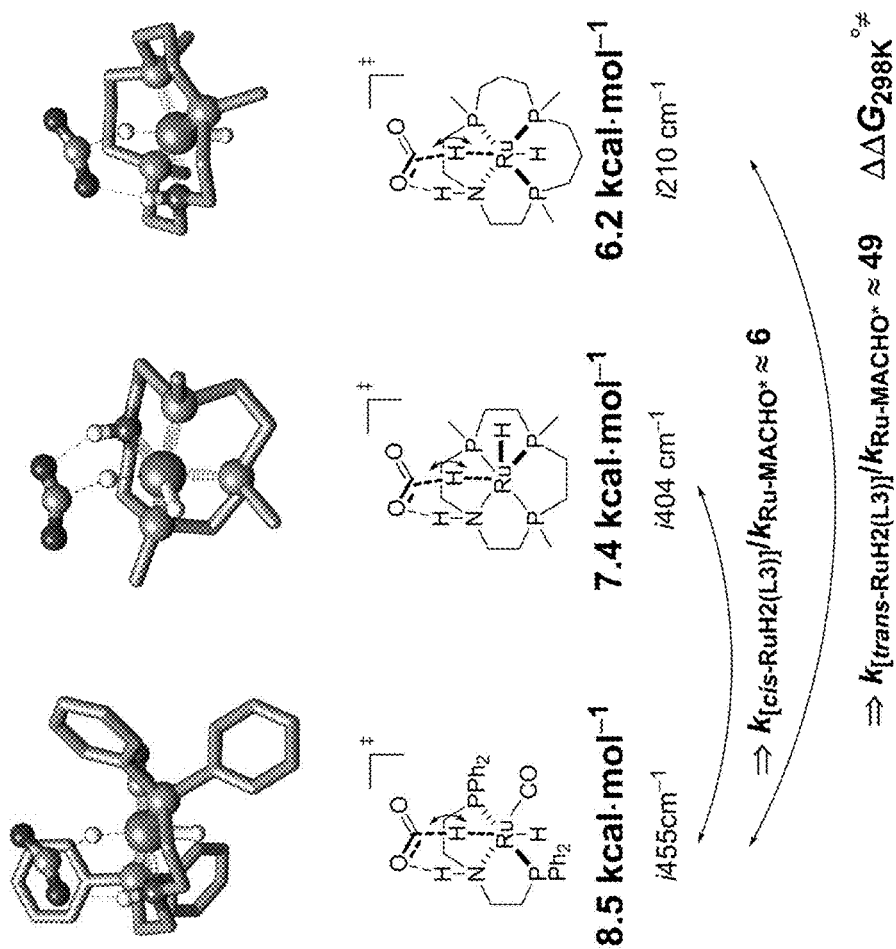
FIG. 4 depicts computed relative rate of hydride transfer from [cis-$RuH_2(L2)$] and [trans-$RuH_2(L3)$] catalysts disclosed herein to carbon dioxide.

FIG. 4 demonstrates the computed activation barriers for the outer-sphere hydride transfer to $CO_2$ (optimized at the M06L/SDD(Ru)/6-31G*(all others) level of theory) by four active Ru—H$_2$ intermediates within the catalytic cycle of their corresponding (pre-catalysts):

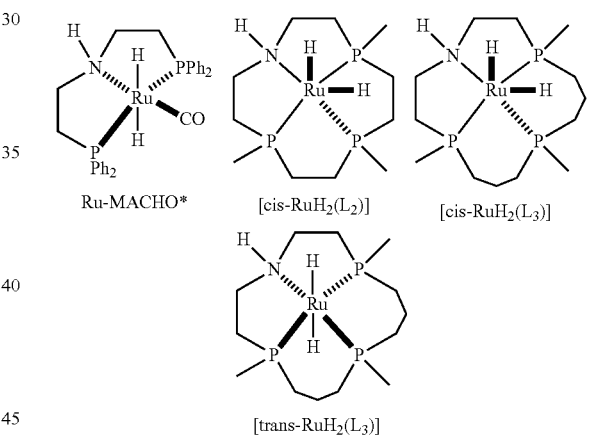

to $CO_2$ optimized under M06L/SDD(Ru)/6-31G*(all others) level of theory.

For ligand L2, the corresponding Ru catalyst exists exclusively in the form of [cis-RuH$_2$(L2)] according to computational analysis described herein. This catalyst transfers the hydride moiety to $CO_2$ six times faster than the conventional Ru-MACHO* catalyst. For ligand L3, the corresponding Ru catalyst exists almost in 1:1 mixture of [cis-RuH$_2$(L3)] and [trans-RuH$_2$(L3)] according to computational analysis described above. However, outer-sphere hydride transfer to $CO_2$ takes place more effectively in [trans-RuH$_2$(L3)], by ~2 kcal·mol$^{-1}$ as verified by separate computations. In general, [trans-RuH$_2$(L3)] transfers a hydride fragment to $CO_2$ ~49 times faster than the Ru-MACHO* catalyst. Assuming that the rate of hydride transfer is equivalent to the rate of the overall catalytic reaction), the TON in for $CO_2$ conversion into methanol can be increased from the reported value of 2000 to 100 000. [trans-RuH$_2$(L3)] being comprised of a macrocyclic tetradentate ligand, exhibits higher stability, thereby resulting in an even better turnover number.

In view of the many possible embodiments to which the principles of the disclosed invention may be applied, it should be recognized that the illustrated embodiments are only preferred examples of the invention and should not be taken as limiting the scope of the invention.

What is claimed is:

1. A macrocyclic ligand of Formula 1A, 1B, 1C or 1D:

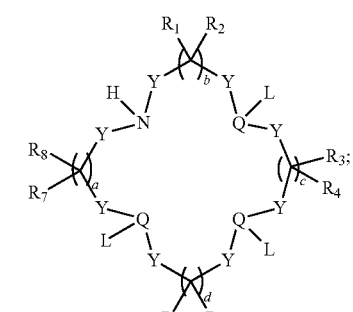

Formula 1A

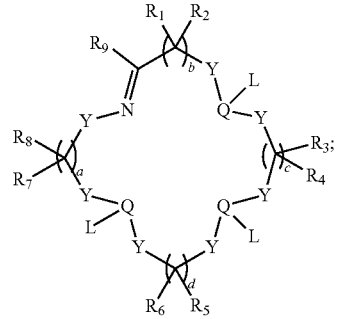

Formula 1B

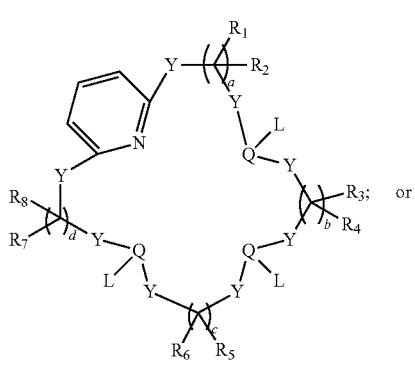

Formula 1C

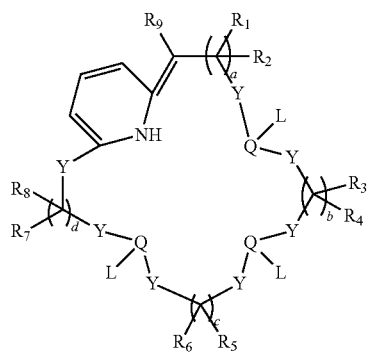

Formula 1D wherein:

Q is phosphorus;

each L is independently selected from a lone pair (or its absence), oxygen, $BH_3$, a hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

each Y is independently selected from a functionality containing a heteroatom selected from NH, O, S, PR, or an optionally substituted $CH_2$ group or its absence, wherein R is selected from hydrogen, a substituted or unsubstituted $C_{1-6}$ alkyl, a substituted or unsubstituted $C_{3-6}$ cycloalkyl, a substituted or unsubstituted aryl, a substituted or unsubstituted heteroaryl, or a substituted or unsubstituted arylalkyl;

a, b, c, and d can independently be an integer selected from 0, 1, 2, 3, 4, 5, 6, 7, 8, 9 or 10; and $R_1$, $R_2$, $R_3$, $R_4$, $R_5$, $R_6$, $R_7$, $R_8$ and $R_9$ are independently at each occurrence H, a substituted or unsubstituted $C_{1-6}$ alkyl, a substituted or unsubstituted $C_{3-6}$ cycloalkyl, a substituted or unsubstituted aryl, a substituted or unsubstituted heteroaryl, a substituted or unsubstituted arylalkyl, or a combination thereof.

2. The macrocyclic ligand of claim 1, wherein each of the $R_1$, $R_2$, $R_3$, $R_4$, $R_5$, $R_6$, $R_7$, $R_8$ and $R_9$ can independently be alkyl, alkenyl, heteroalkyl, heteroalkenyl, heteroalkynyl, haloalkyl, haloalkenyl, haloalkynyl, haloheteroalkyl, haloheteroalkenyl, haloheteroalkynyl, aryl, heteroaryl, alkyl-aryl/alkeny-aryl/alkynyl-aryl, alkyl-heteroaryl/alkenyl-heteroaryl/alkynyl-heteroaryl, heteroalkyl-aryl/heteroalkenyl-aryl/heteroalkynyl-aryl, heteroalkyl-heteroaryl/heteroalkenyl-heteroaryl/heteroalkynyl-heteroaryl or any combination thereof.

3. The macrocyclic ligand of claim 1, wherein the ligand is selected from:

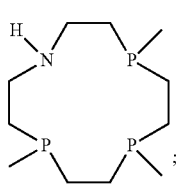 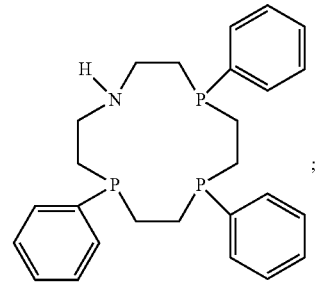

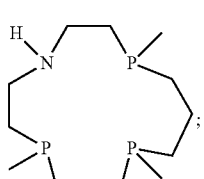 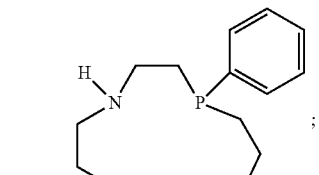

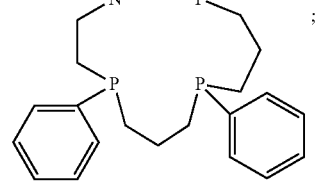

91
-continued

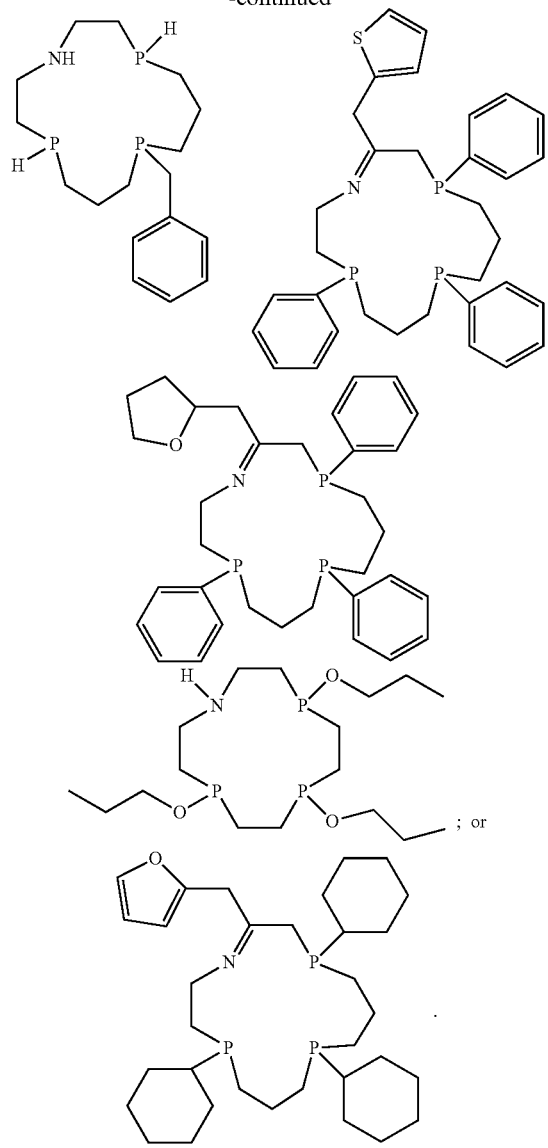

4. The macrocyclic ligand of claim 1, wherein the ligand is selected from:

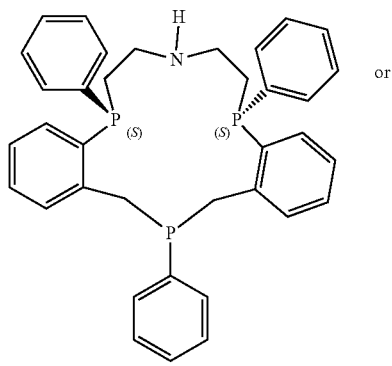

92
-continued

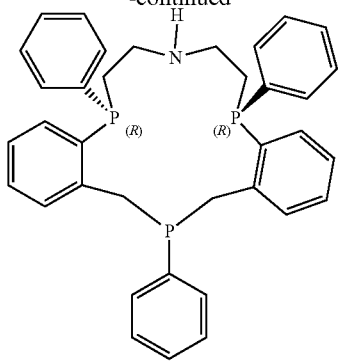

5. The macrocyclic ligand of claim 1, wherein the ligand is:

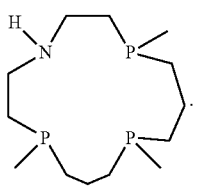

6. The macrocyclic ligand of claim 1, wherein each L is a substituted or unsubstituted $C_{1-6}$ alkyl.

7. The macrocyclic ligand of claim 1, wherein at least one L is a substituted or unsubstituted $C_{1-6}$ alkyl.

8. The macrocyclic ligand of claim 1, wherein at least one L is a substituted or unsubstituted $C_{3-6}$ cycloalkyl.

9. The macrocyclic ligand of claim 1, wherein at least one L is a substituted or unsubstituted aryl.

10. The macrocyclic ligand of claim 1, wherein each Y is —$CH_2$—.

11. The macrocyclic ligand of claim 1, wherein a, b, c, and are each independently 0 or 1.

12. The macrocyclic ligand of claim 1, wherein the macrocyclic ligand is of Formula 1A.

13. The macrocyclic ligand of claim 1, wherein each of $R_1$, $R_2$, $R_3$, $R_4$, $R_5$, $R_6$, $R_7$, $R_8$, and $R_9$ is a hydrogen.

14. The macrocyclic ligand of claim 1, wherein each L is a methyl.

15. The macrocyclic ligand of claim 1, wherein each L is a phenyl.

16. The macrocyclic ligand of claim 10, wherein a, b, c, and are each independently 0 or 1, and each of $R_1$, $R_2$, $R_3$, $R_4$, $R_5$, $R_6$, $R_7$, $R_8$, and $R_9$ is a hydrogen.

* * * * *